United States Patent
Niwa et al.

(10) Patent No.: US 10,761,087 B2
(45) Date of Patent: Sep. 1, 2020

(54) CHOROIDAL NEOVASCULARIZATION SUPPRESSOR OR DRUSEN FORMATION SUPPRESSOR, AND METHOD FOR ASSESSING OR SCREENING FOR SAME

(71) Applicants: Link Genomics, Inc., Tokyo (JP); ROHTO Pharmaceutical Co., Ltd., Osaka (JP)

(72) Inventors: Shinichiro Niwa, Tokyo (JP); Dai Ogura, Tokyo (JP); Hidemi Mizunuma, Tokyo (JP); Yoko Arai, Tokyo (JP); Takahiro Kurose, Osaka (JP); Yoshihiro Takai, Osaka (JP); Yoko Mitsuguchi, Osaka (JP); Mariyo Moriya, Osaka (JP)

(73) Assignees: LINK GENOMICS, INC., Tokyo (JP); ROHTO Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 16/063,047

(22) PCT Filed: Dec. 16, 2016

(86) PCT No.: PCT/JP2016/087647
§ 371 (c)(1),
(2) Date: Jun. 15, 2018

(87) PCT Pub. No.: WO2017/104833
PCT Pub. Date: Jun. 22, 2017

(65) Prior Publication Data
US 2018/0364216 A1    Dec. 20, 2018

(30) Foreign Application Priority Data

Dec. 17, 2015  (JP) ................................ 2015-246742
Jul. 5, 2016   (JP) ................................ 2016-133753

(51) Int. Cl.
| | |
|---|---|
| G01N 33/50 | (2006.01) |
| A61K 31/436 | (2006.01) |
| A61K 31/192 | (2006.01) |
| A61K 31/38 | (2006.01) |
| A61K 31/404 | (2006.01) |
| A61K 31/421 | (2006.01) |
| A61K 31/426 | (2006.01) |
| A61K 31/47 | (2006.01) |
| A61K 31/41 | (2006.01) |
| A61K 45/00 | (2006.01) |
| A61P 27/02 | (2006.01) |
| A61K 45/06 | (2006.01) |

(52) U.S. Cl.
CPC ....... *G01N 33/5023* (2013.01); *A61K 31/192* (2013.01); *A61K 31/38* (2013.01); *A61K 31/404* (2013.01); *A61K 31/41* (2013.01); *A61K 31/421* (2013.01); *A61K 31/426* (2013.01); *A61K 31/436* (2013.01); *A61K 31/47* (2013.01); *A61K 45/00* (2013.01); *A61P 27/02* (2018.01); *A61K 45/06* (2013.01); *A61K 2300/00* (2013.01)

(58) Field of Classification Search
None
See application file for complete search history.

(56) References Cited

U.S. PATENT DOCUMENTS

| | | | | |
|---|---|---|---|---|
| 9,326,960 B2 * | 5/2016 | Kim | ................... | A61K 36/8962 |
| 2007/0196350 A1 * | 8/2007 | Bartels | ................ | A61K 9/0048 |
| | | | | 424/94.4 |
| 2015/0231100 A1 * | 8/2015 | Kim | .................... | A61K 31/195 |
| | | | | 514/562 |

FOREIGN PATENT DOCUMENTS

WO    WO-2014027865 A1 *  2/2014    ......... A61K 36/8962

OTHER PUBLICATIONS

Hirasawa et al. Molecular Vision, 2011, vol. 17, p. 1222-1230.*
English Translation of the International Preliminary Report on Patentability (Chapter I) for International Application No. PCT/JP2016/087647, dated Jun. 28, 2018.
English Translation of Hirayama, M. et al. (2011) "Anti-VEGF therapy in exudative age-related macular degeneration (Sinshutugata karei ohan hensei ni okeru ko-VEGF tiryo)," Igaku No Ayumi 236:1165-1167.
English Translation of Ishida, S. et al. (2010) "Aging and AMD (Karei to AMD)," Pharma Medica 28(12):9-12.
English Translation of Iwata, E. et al. (2011) "Age-related macular degeneration (Karei ohan hensei)," The Current Medicine 59(1):133-138.
English Translation of Takahashi, E. et al. (2016) "The Regulation of Epithelial Mesenchymal Transition in Ocular Disorders," Journal of Japanese Ophthalmological Society 120(11):783-790.
English Translation of Takahashi, K. et al. (2015) "Diagnostic criteria of atrophic age-related macular degeneration (Ishukusei karei ohan hensei no sindan kijun)," Nichigankaishi 119:671-677.

(Continued)

*Primary Examiner* — Jeffrey S Lundgren
*Assistant Examiner* — Michael J Schmitt
(74) *Attorney, Agent, or Firm* — Foley & Lardner LLP

(57) ABSTRACT

The existent therapeutic drugs for CNV are merely pharmaceuticals for a symptomatic therapy, and therapeutic drugs for radical cure are strongly demanded. Also, a therapeutic drug for Dry AMD does not exist, and therapeutic drugs for radical cure are strongly demanded. The present invention provides a prophylactic and/or therapeutic agent for choroidal neovascularization, containing a compound having an activity of suppressing epithelial-mesenchymal transition in retinal pigment epithelial cells, as an active ingredient. Also, the present invention provides a drusen suppressor comprising a compound having an activity of suppressing epithelial-mesenchymal transition in retinal pigment epithelial cells, as an active ingredient.

6 Claims, 36 Drawing Sheets

(56) References Cited

OTHER PUBLICATIONS

English Translation of Yasukawa, T. (2011) "Seminar 5. Precursor lesions of agerelated macular degeneration (AMD) and symptoms thereof (Karei ohan hensei (AMD) no zenku byohen to sono syojo)," GeriatricMedicine 49(4):409-412.

Hirasawa, M. et al. (2011) "Transcriptional factors associated with epithelial-mesenchymal transition in choroidal neovascularization," Molecular Vision 17:1222-1230.

Hirayama, M. et al. (2011) "Anti-VEGF therapy in exudative age-related macular degeneration (Sinshutugata karei ohan hensei ni okeru ko-VEGF tiryo)," Igaku No Ayumi 236:1165-1167.

Hwang, K.E. et al. (2015) "Down-regulated SIRT1 by Nonsteroidal Antiinflammatory Drugs is to Inhibit TGF-1 induced Epithelial-Mesenchymal Transition and to Suppress Migration and Invasion in Lung Cancer," Chest 148(4): Meeting Abstract, 548A.

Ishida, S. et al. (2010) "Aging and AMD (Karei to AMD)," Pharma Medica 28(12):9-12.

Iwata, E. et al. (2011) "Age-related macular degeneration (Karei ohan hensei)," The Current Medicine 59(1):133-138.

Sakamoto, T. et al. (2010) "Non-steroidal anti-inflammatory drug(NSAID) in exudative AMD," Journal of Japanese Ophthalmological Society. 114 (special extra issue):127, Abstract.

Sur, A. et al. (2014) "Pharmacological protection of retinal pigmented epithelial cells by sulindac involves PPAR-α," Proc Natl Acad Sci USA. 111(47):16754-16759.

Suzuki, M. et al. (2012) "Cyclooxygenase inhibitor improved an exudative lesion of choroidal neovascularization in age-related macular degeneration," European Journal of Ophthalmology 22(3):495-498.

Takahashi, E. et al. (2010) Tumor Necrosis Factor-α Regulates Transforming Growth Factor-β-dependent Epithelial-Mesenchyamal Transition by Promoting Hyaluronan-CD44-Moesin Interaction, The Journal of Biological Chemistry 285(6):4060-4073.

Takahashi, E. et al. (2016) "The Regulation of Epithelial Mesenchymal Transition in Ocular Disorders," Journal of Japanese Ophthalmological Society 120(11):783-790.

Takahashi, K. et al. (2015) "Diagnostic criteria of atrophic age-related macular degeneration (Ishukusei karei ohan hensei no sindan kijun)," Nichigankaishi 119:671-677.

Yasukawa, T. (2011) "Seminar 5. Precursor lesions of agerelated macular degeneration (AMD) and symptoms thereof (Karei ohan hensei (AMD) no zenku byohen to sono syojo)," Geriatric Medicine 49(4):409-412.

Zhou, X. et al. (2015) "Sulindac has strong antifibrotic effects by suppressing STAT3-related miR-21," J. Cell. Mol. Med. 19(5):1103-1113.

International Search Report (ISA/JP) for International Application No. PCT/JP2016/087647, dated Feb. 21, 2017.

Extended European Search Report issued in EP Application No. 16875807.6 dated Mar. 18, 2019, 18 pages.

* cited by examiner

CHOROIDAL NEOVASCULARIZATION SUPPRESSOR OR DRUSEN FORMATION SUPPRESSOR, AND METHOD FOR ASSESSING OR SCREENING FOR SAME

CROSS-REFERENCE TO RELATED APPLICATIONS

This application is a national stage entry under 35 U.S.C. § 371 of International Patent Application No. PCT/JP2016/087647, filed Dec. 16, 2016, which in turn claims priority to Japanese Patent Application No. 2015-246742, filed Dec. 17, 2015, and Japanese Patent Application No. 2016-133753, filed Jul. 5, 2016, the entire content of each of which is hereby incorporated by reference.

TECHNICAL FIELD

The present invention relates to pharmaceuticals for preventing or treating choroidal neovascularization.

Also, the present invention relates to a drusen suppressor, or a method for assessing or screening for such a drug.

BACKGROUND ART

Choroidal neovascularization (CNV) is a disease in which new blood vessels develop from the choroid in the macula of the ocular fundus, and appears in angioid streaks of retina, pathological myopia, ophthalmic histoplasmosis, posttraumatic choroidal rupture and the like, besides in age-related macular degeneration (AMD).

Since new choroidal blood vessels are fragile, the blood components exude, to cause retinal edema and accumulation of subretinal fluid. Further, as a result of hemorrhage due to rupture of fragile new blood vessels, the failure that influences on decline in visual acuity progresses acceleratively (Non-patent document 1).

For example, for choroidal neovascularization in age-related macular degeneration, angiogenesis inhibitors such as an anti-VEGF drug that inhibit neovascularization have been used (Non-patent document 2).

AMD is a disease in which the macula of the retina becomes damaged by a factor such as aging, to result in visual loss. In advanced AMD, objects or linear objects appear distorted (metamorphopsia), and color cannot be recognized, and patients with advanced AMD can become sensitive to light, and become largely influenced in their Quality of Life. More advanced AMD can result in partial defect of visual field (central scotoma, etc.), and can lead to blindness (Non-patent document 3).

AMD is roughly classified into Wet AMD (exudative AMD), and Dry AMD (atrophic AMD) according to the characteristic clinical state. Wet AMD is a type characterized by abnormal neovascularization and rupture thereof. In Wet AMD, blood vessels newly develop from the choroid under retinal pigment epithelium (RPE cells), and blood components exude from these fragile blood vessels to cause retinal edema and accumulation of subretinal fluid. Further, as a result of hemorrhage due to rupture of fragile blood vessels, the failure that influences on decline in visual acuity progresses acceleratively (Non-patent document 1).

As a therapeutic method of AMD, angiogenesis inhibitors such as an anti-VEGF (vascular endothelial growth factor) drug that inhibit neovascularization have been used for Wet AMD (Non-patent document 2).

On the other hand, Dry AMD is a disease that is diagnosed based on the criteria for visual acuity, funduscopic findings, image findings, exception, severity classification and the like (Non-patent document 4). Irregularity in visual cells caused by a structure called drusen is considered as one causal factor (Non-patent document 5). There is a report that some Dry AMD transit to Wet AMD.

PRIOR ART DOCUMENTS

Non-Patent Documents

Non-patent Document 1: Eiji IWATA et al. (2011). "Age-related macular degeneration (Karei ohan hensei)", The Current Medicine, Vol. 59, No. 1, 133 to 138

Non-patent Document 2: Mariko HIRAYAMA et al. (2011). "Anti-VEGF therapy in exudative age-related macular degeneration (Sinshutugata karei ohan hensei ni okeru ko-VEGF tiryo)", IGAKU NO AYUMI, Vol. 236 1165 to 1167

Non-patent Document 3: Susumu ISHIDA et al. (2010). "Aging and AMD (Karei to AMD)" Pharma Medica Vol. 28, No. 12, 9-12

Non-patent Document 4: Kanji TAKAHASHI et al. (2015). "Diagnostic criteria of atrophic age-related macular degeneration (Ishukusei karei ohan hensei no sindan kijun)", Nichigankaishi, 119, 671-677

Non-patent Document 5: Tsutomu YASUKAWA (2011). Seminar 5. "Precursor lesions of age-related macular degeneration (AMD) and symptoms thereof (Karei ohan hensei (AMD) no zenku byohen to sono syojo)", Geriatric Medicine Vol. 49, No. 4 409 to 412

SUMMARY OF THE INVENTION

Problems to be Solved by the Invention

It is an object of the present invention to provide a prophylactic and/or therapeutic agent for CNV.

It is also an object of the present invention to provide a drusen suppressor.

Means for Solving the Problems

Inhibition of neovascularization using an antibody or the like that targets for VEGF is a symptomatic therapy, and does not suppresses or improves the action of the cells themselves that produce VEGF. Further, biological preparations such as antibodies require high medical expenses as the treatment period is prolonged. Further, pharmaceuticals that require intraocular injection are highly invasive, and put a great burden on patients. Therefore, therapeutic drugs that are lowly invasive, and economic for radical therapy of CNV are strongly demanded.

As a result of diligent studies for solving the aforementioned problems, the present inventors found that by suppressing epithelial-mesenchymal transition (EMT) in retinal pigment epithelial cells (RPE cells) by specific nonsteroidal anti-inflammatory drugs (NSAIDs), aldose reductase inhibitors, leukotriene receptor antagonists, chemical mediator release suppressors, and thromboxane A2 receptor antagonists, expression of VEGF in RPE cells is suppressed, and choroidal neovascularization can be prevented and/or treated, and finally accomplished the preset invention.

That is, the present invention relates to:

[1] A prophylactic and/or therapeutic agent for choroidal neovascularization, containing at least one selected from the group consisting of zaltoprofen, oxaprozin, tiaprofenic acid, flufenamic acid, mefenamic acid, sulindac, epalrestat, zafirlukast, amlexanox, seratrodast and pharmaceutically acceptable salts thereof, as an active ingredient;

[2]

The prophylactic and/or therapeutic agent for choroidal neovascularization according to the above [1], which is an oral agent;

[3]

The prophylactic and/or therapeutic agent for choroidal neovascularization according to the above [1] or [2], wherein the choroidal neovascularization occurs in age-related macular degeneration, polypoidal choroidal vasculopathy (PCV), or retinal angiomatous proliferation (RAP).

Also in the present invention, it is expected that symptoms such as distortion in visual field in Dry AMD can be ameliorated by suppressing drusen. However, a therapeutic drug that is effective for Dry AMD does not exist, and a therapeutic drug for radical cure is strongly demanded.

As a result of diligent studies for solving the aforementioned problems, the present inventors obtained new findings that drusen are structures caused by occurrence of epithelial-mesenchymal transition (EMT) in RPE cells. On the basis of the findings, the present inventors found that EMT can be easily induced in RPE cells, drusen can be reproduced in RPE cells, and that through assessment or screening of EMT suppressive compounds capable of suppressing EMT in RPE cells, these compounds are capable of suppressing drusen in RPE cells, and finally accomplished the present invention.

That is, the present invention relates to:

[4]

A drusen suppressor comprising a compound having an activity of suppressing epithelial-mesenchymal transition in retinal pigment epithelial cells, as an active ingredient;

[5]

The drusen suppressor according to the above [4], wherein the compound having an activity of suppressing epithelial-mesenchymal transition is an agent that suppresses expression of a mesenchymal marker or an extracellular matrix in the cells;

[6]

The drusen suppressor according to the above [5], wherein the mesenchymal marker is at least one selected from the group consisting of Snail, Slug, cadherin3, MMP1, and MMP7, and/or, the extracellular matrix is at least one selected from the group consisting of COL5A3, COL6A3, LAMC2, HMMR, and TNC;

[7]

The drusen suppressor according to any one of the above [4] to [6], wherein the compound having an activity of suppressing epithelial-mesenchymal transition is a nonsteroidal anti-inflammatory drug, an aldose reductase inhibitor, a leukotriene receptor antagonist, a chemical mediator release suppressor, and/or a thromboxane A2 receptor antagonist;

[8]

The drusen suppressor according to the above [7], wherein the nonsteroidal anti-inflammatory drug is at least one selected from the group consisting of zaltoprofen, oxaprozin, tiaprofenic acid, flufenamic acid, mefenamic acid, sulindac, ibuprofen, flurbiprofen, and pharmaceutically acceptable salts thereof, the aldose reductase inhibitor is epalrestat and/or a pharmaceutically acceptable salt thereof, the leukotriene receptor antagonist is at least one selected from the group consisting of zafirlukast, montelukast, pranlukast, and pharmaceutically acceptable salts thereof, the chemical mediator release suppressor is amlexanox and/or a pharmaceutically acceptable salt thereof, and/or, the thromboxane A2 receptor antagonist is seratrodast and/or a pharmaceutically acceptable salt thereof.

Also, the present invention relates to:

[9]

A prophylactic and/or therapeutic agent for age-related macular degeneration, containing a propionic acid-based nonsteroidal anti-inflammatory drug, an aminoaryl carboxylic acid-based nonsteroidal anti-inflammatory drug, an aryl acetic acid-based nonsteroidal anti-inflammatory drug, an aldose reductase inhibitor, a leukotriene receptor antagonist, a chemical mediator release suppressor, or a thromboxane A2 receptor antagonist as an active ingredient, wherein the aldose reductase inhibitor is epalrestat and/or a pharmaceutically acceptable salt thereof;

[10]

The prophylactic and/or therapeutic agent for age-related macular degeneration according to the above [9], wherein the propionic acid-based nonsteroidal anti-inflammatory drug is at least one selected from the group consisting of zaltoprofen, oxaprozin, ibuprofen, flurbiprofen, tiaprofenic acid, and pharmaceutically acceptable salts thereof, the aminoaryl carboxylic acid-based nonsteroidal anti-inflammatory drug is at least one selected from the group consisting of flufenamic acid, mefenamic acid, and pharmaceutically acceptable salts thereof, the aryl acetic acid-based nonsteroidal anti-inflammatory drug is sulindac and/or a pharmaceutically acceptable salt thereof, the leukotriene receptor antagonist is at least one selected from the group consisting of zafirlukast, montelukast, pranlukast, and pharmaceutically acceptable salts thereof, and/or the chemical mediator release suppressor is amlexanox and/or a pharmaceutically acceptable salt thereof, the thromboxane A2 receptor antagonist is seratrodast and/or a pharmaceutically acceptable salt thereof.

Also, the present invention relates to

[11]

A prophylactic and/or therapeutic agent for age-related macular degeneration, comprising a combination of an angiogenesis inhibitor and the drusen suppressor according to any one of the above [4] to [8].

Also, the present invention relates to

[12]

A method for assessing or screening a drusen suppressor, including measuring suppression of epithelial-mesenchymal transition in retinal pigment epithelial cells in vitro in the presence of a test drug.

Also, the present invention relates to

[13]

A method for assessing or screening a drusen suppressor, including measuring suppression of agglomeration of retinal pigment epithelial cells in vitro in the presence of a test drug.

Also, the present invention relates to

[14]

A method for assessing or screening a prophylactic and/or therapeutic agent for age-related macular degeneration, including measuring suppression of epithelial-mesenchymal transition in retinal pigment epithelial cells in vitro in the presence of a test drug.

Also, the present invention relates to

[15]

A method for assessing or screening a prophylactic and/or therapeutic agent for age-related macular degeneration, including measuring suppression of agglomeration of retinal pigment epithelial cells in vitro in the presence of a test drug.

Effect of the Invention

The compound of the present invention is useful as a prophylactic and/or therapeutic agent for choroidal neovascularization because the compound is capable of suppressing expression of VEGF by suppressing EMT in RPE cells. Further, the present invention has sufficient safety as pharmaceuticals.

Also from other view point, the present invention enables to effectively suppress drusen by using an EMT suppressive compound.

MODE FOR CARRYING OUT THE INVENTION

Figure 1:
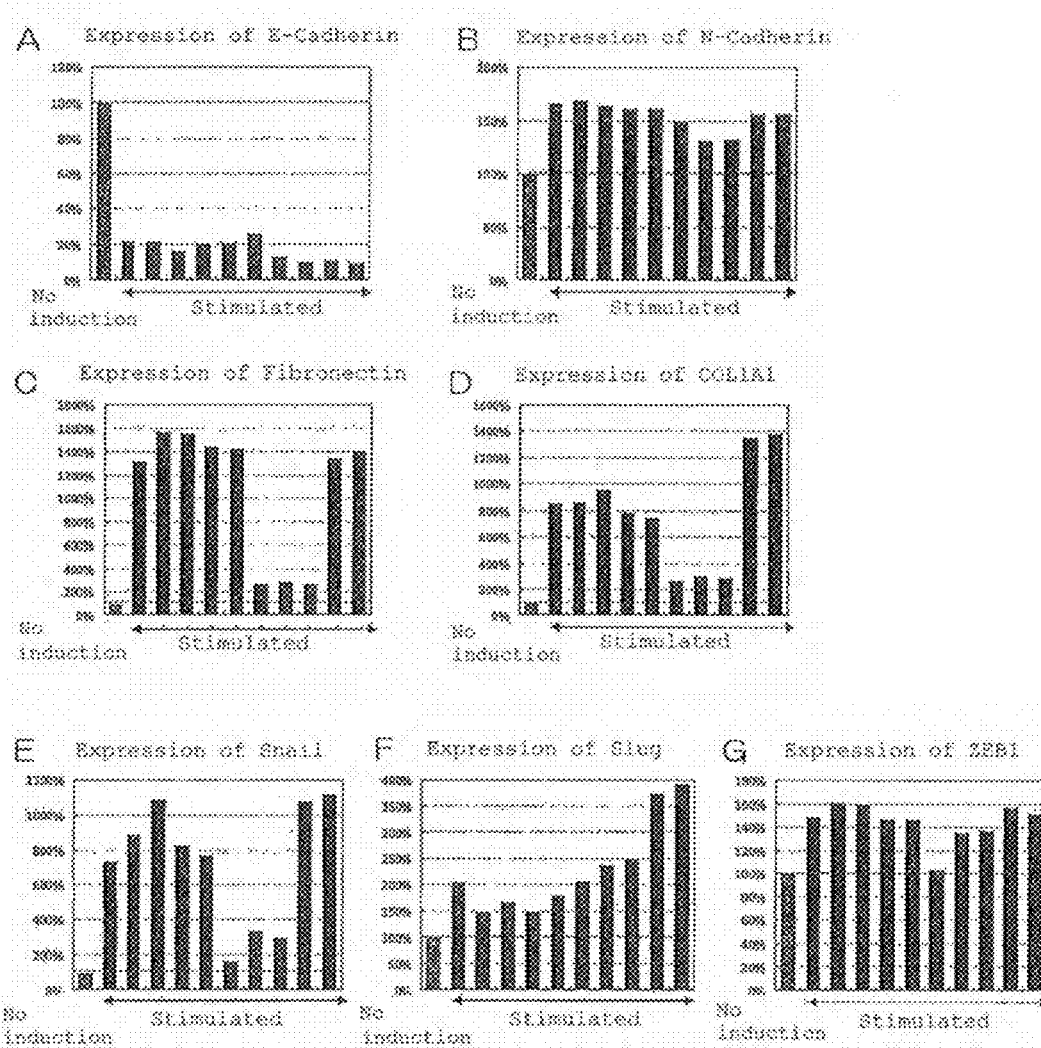
FIG. 1 includes graphs showing the results of EMT induction in RPE cells, verified by change in expression of EMT marker molecules.

Hereinafter, the present invention is described in detail.

[Prophylactic and/or Therapeutic Agent for Choroidal Neovascularization]

A prophylactic and/or therapeutic agent for choroidal neovascularization of the present invention contains at least one selected from the group consisting of zaltoprofen, oxaprozin, tiaprofenic acid, flufenamic acid, mefenamic acid, sulindac, epalrestat, zafirlukast, amlexanox, seratrodast, and pharmaceutically acceptable salts thereof, as an active ingredient.

In the present description, "choroidal neovascularization (CNV)" refers to development, propagation and/or extension of a new blood vessel from the choroid of the fundus oculi. Although not limited to the following, the new blood vessel developed from the choroid extends through the Bruch's membrane and/or a layer where retinal pigment epithelial cells exist. CNV can be examined by a known method. Although not limited to the following, CNV can be examined, for example, by a fundus angiography using a fluorescent pigment such as fluorescein.

In the present description, "retinal pigment epithelial cell (RPE cell)" refers to a monolayer cubic epithelial cell existing under the retina of the eye.

The present inventors infer that the epithelial mesenchymal transition (EMT) in RPE cells is a major causal factor of CNV. In the present description, "epithelial mesenchymal transition (EMT)" refers to such a phenomenon that epithelial cells lose the epithelial character and acquire the mesenchymal character. Cancelling of intercellular adhesion in epithelial cells results in morphologic change of the cells, and the cells acquire the mobility. Expression of the epithelial marker that has been expressed as an epithelial cell is suppressed, and expression of a mesenchymal marker and secretion of an extracellular matrix (ECM) are enhanced (in this description, an epithelial marker, a mesenchymal marker, and/or ECM are also called EMT markers).

The present inventors made the following hypothesis regarding development of CNV, and made verification. The present inventors have found that generation of EMT in RPE cells due to some external stimulation causes degeneration of RPE cells, and generation of drusen. It is considered that, in RPE cells that are exfoliated from the Bruch's membrane in the course of formation of drusen, supply of oxygen and nutrients from the lamina choriocapillaris directly under the Bruch's membrane is blocked, and thus secretion of VEGF or part of MMPs is enhanced due to a local hypoxic state. It is considered that, even when formation of drusen is not led, occurrence of EMT in RPE cells enhances secretion of VEGF or part of MMPs, as well as a mesenchymal marker or an extracellular matrix from the RPE cells. By these MMPs, breakdown and perforation occur in the Bruch's membrane, and angiogenesis from the choroid is induced by VEGF.

Since a new blood vessel is fragile, leakage of blood is likely to occur. Also, occurrence of subretinal hemorrhage due to rupture of fragile new blood vessels rapidly causes decline in visual acuity and can lead to blindness.

Examples of CNV-related diseases (ICD10: International classification of disease, the tenth edition (revised in 2003)) include age-related macular degeneration, exudative age-related macular degeneration, drusen, exudative retinitis, polypoidal choroidal vasculopathy (PCV), exudative retinopathy, central serous chorioretinopathy, central serous choroidopathy, hemorrhagic detachment of the retinal pigment epithelium, proliferative vitreoretinopathy, proliferative retinopathy, serous detachment of the retinal pigment epithelium, idiopathic choroidal neovascularization, retinal edema, retinal neovascularization, retinal angiomatous proliferation (RAP), retinal angiopathy, atrophic age-related macular degeneration, neovascular maculopathy, soft drusen, myopic choroidal neovascularization, macular degeneration, maculopathy, macular angiectopia, and macular disorder.

Examples of the effect-efficiency for these diseases include age-related macular degeneration accompanied by a subfoveal choroidal neovascularization.

Also, examples of CNV-related diseases (standard name of disease: ICD10) include myopic choroidal neovascularization, and idiopathic choroidal neovascularization.

Examples of the effect-efficiency for these diseases include choroidal neovascularization in pathologic myopia.

Also, examples of CNV-related diseases (standard name of disease: ICD10) include diabetic macular edema, type 1 diabetic macular edema, type 1 diabetic maculopathy, type 2 diabetic macular edema, type 2 diabetic maculopathy, and diabetic maculopathy.

Examples of the effect-efficiency for these diseases include diabetic macular edema.

Also, examples of CNV-related diseases (standard name of disease: ICD10) include macular edema due to retinal vein occlusion, central retinal vein embolism, central retinal vein thrombosis, central retinal vein occlusion, macular edema due to central retinal vein occlusion, retinal vein thrombosis, and retinal vein occlusion.

Examples of the effect-efficiency for these diseases include macular edema associated with retinal vein occlusion.

As to classification of age-related macular degeneration (AMD), classification into early AMD, intermediate AMD or late AMD, classification into non-progressive AMD or progressive AMD, and the like, besides general classification in to Dry AMD and Wet AMD have been reported. Examples of a specific type of Wet AMD include, but not limited to, retinal angiomatous proliferation (RAP).

Although not limited to the following, a new blood vessel in CNV can extend in a variety of directions above the Bruch's membrane or RPE cells, and a polypus-shaped new blood vessel can be formed under RPE cells as with the case with polypoidal choroidal vasculopathy (PCV).

As exudative AMD, a clinical state accompanied by CNV including a central fovea is known. Such AMD can be classified into three types of disease including typical AMD, PCV or RAP, and an initial treatment can be individually selected.

In the present description, any disease based on any classification can be a target for prophylaxis and/or therapy as long as it is a retinal disease accompanied by development of CNV.

Among the classifications of AMD, Wet AMD (exudative AMD), in particular, has a close relation with CNV because CNV develops in the subfoveal space through blood leakage and humidification, and subretinal hemorrhage is often observed around the CNV.

According to such an inferred mechanism of CNV development, it is expected that each of zaltoprofen, oxaprozin, tiaprofenic acid, flufenamic acid, mefenamic acid, sulindac, epalrestat, zafirlukast, amlexanox, seratrodast, and pharmaceutically acceptable salts thereof strongly suppresses EMT in RPE cells, and thus suppresses production of VEGF or MMPs involved in development or extension of CNV, and is capable of radically preventing and/or treating CNV.

Generation of EMT or suppression of EMT can be measured or assessed by a known method. Although not limited to the following, for example, loss of an epithelial character can be verified by measuring expression of an epithelial marker as will be described later. Also, for example, acquisition of a mesenchymal character can be verified by measuring expression of a mesenchymal marker described later or secretion of an extracellular matrix (ECM). Expression of gene or expression or secretion of protein can be measured by a known method such as a microarray, a real-time PCR method, a PCR method, an Western blotting method, an ELISA method, or an immunohistological staining. For example, enhancement of mobility can be measured by a known method such as histological staining, e.g., Giemsa staining or an invasion assay method. For example, morphological change can be measured by a known method such as histological staining, e.g., HE staining.

In the present description, "prophylaxis" refers to preventing development of a disease or a symptom, delaying development of a disease, or preventing reoccurrence of a disease in an individual.

In the present description, "therapy" refers to alleviating a symptom of a disease, making a symptom of a disease disappear, or maintaining a symptom of a disease, or suppressing progression, worsening, aggravation, or exacerbation of a symptom in an individual.

In the present description, "suppress EMT in RPE cells" refers to suppressing loss of the epithelial character in RPE cells, suppressing acquisition of the mesenchymal character, or causing loss of the acquired mesenchymal character. Although not limited to the following, EMT suppression in RPE cells can be assessed, for example, by detecting that expression of an epithelial marker is maintained, expression of a mesenchymal marker is suppressed, expression and/or secretion of ECM is suppressed, or enhancement of mobility in RPE cells is suppressed.

The compound having EMT suppressive activity in RPE cells (also referred to as EMT suppressive compound in the present description) includes compounds that are known to have an EMT suppressive activity in epithelial cells. Examples of the EMT suppressive compound include a nonsteroidal anti-inflammatory drug, an aldose reductase inhibitor, a leukotriene receptor antagonist, a chemical mediator release suppressor, and a thromboxane A2 receptor antagonist, and from the view point of exerting a significant EMT suppressive effect, zaltoprofen, oxaprozin, tiaprofenic acid, flufenamic acid, mefenamic acid, sulindac, epalrestat, zafirlukast, amlexanox, seratrodast, or a pharmaceutically acceptable salt thereof is used. As the EMT suppressive compound, the one having an excellent factor involved in BRB permeability such as lipid solubility is preferred from the view point of blood-retinal barrier (BRB) permeability. Although not limited to the following, since a compound having high lipid solubility has excellent BRB permeability, high prophylactic/therapeutic effect against retinal diseases are expected even when such a compound is administered orally and thus is not directly delivered to an eye. The EMT suppressive compound is preferably a compound that has little side effect from the view point of allowance of chronic administration depending on the symptom. Examples of the side effect include, but not limited to, anorexia, diarrhea, stomatitis, dyspepsia, gastritis, itching, and liver malfunction. From the view point of these BRB permeability and/or side effect, zaltoprofen, oxaprozin, tiaprofenic acid, flufenamic acid, mefenamic acid, sulindac, epalrestat, zafirlukast, amlexanox, seratrodast, or a pharmaceutically acceptable salt thereof is preferred. These ingredients may be synthesized by known methods or may be commercially available products.

In the present description, specific examples of "pharmaceutically acceptable salt" include, but not particularly limited to, organic acid salts, inorganic acid salts, organic bases, or inorganic bases. Examples of the organic acid salts include monocarboxylates such as acetate, trifluoroacetate, butyrate, palmitate, and stearate; polyvalent carboxylates such as fumarate, maleate, succinate, and malonate; oxycarbonates such as lactate, tartrate, and citrate; and organic sulfonates such as methanesulfonate, toluenesulfonate, and tosylate. Examples of the inorganic acid salts include hydrochloride, sulfate, nitrate, hydrobromate, and phosphate. Examples of the salts with organic base include salts with organic amines such as methylamine, triethylamine, triethanolamine, diethanolamine, morpholine, piperazine, pyrrolidine, tripyridine, picoline, and ethylenediamine. Examples of the salts with inorganic base include various salts including ammonium salts, and salts with alkali metal such as sodium or potassium, alkali earth metal such as calcium or magnesium, or metal such as aluminum. These salts may be used singly or in combination of two or more kinds. "Pharmaceutically acceptable salt" may include a solvate or hydrate of salt.

The present inventors found that at least one selected from the group consisting of zaltoprofen, oxaprozin, tiaprofenic acid, flufenamic acid, mefenamic acid, sulindac, epalrestat, zafirlukast, amlexanox, seratrodast, and pharmaceutically acceptable salts thereof significantly suppresses expression of a mesenchymal marker or an extracellular matrix (ECM).

In the present description, a known mesenchymal marker can be used, and examples of the mesenchymal marker include, but not limited to, Snail (SNAI1), Slug (SNAI2), matrix metalloprotease 1 (MMP1), MMP7, MMP2, MMP3, MMP9, N-cadherin (CDH2), CDH3, ZEB1, ZEB2 (SIP1), α-SMA, vimentin (VIM), FSP-1, β-catenin, OB-cadherin, α5β1 integrin, syndecan 1, ETS, Twist1, Goosecoid, LEF-1, FOXC2, miR10b, miR21, RDX, RHOA, TJP1, CTNNB1, HAS2, SERPINE1, MSN, TCF3, and ITGAV. For assessing EMT suppression, these mesenchymal markers may be used singly or in combination.

For the capability of effectively assessing EMT suppression in RPE cells, the mesenchymal marker is preferably at least one selected from the group consisting of Snail, Slug, CDH3, MMP1, MMP7, MMP3, ZEB2, CDH2, and VIM, and more preferably at least one selected from the group consisting of Snail, Slug, CDH3, MMP1, and MMP7.

In the present description, a known ECM can be used as a marker, and examples of the ECM include, but not limited to, collagen type 5α3 (COL5A3), COL6A3, laminin γ2 (LAMC2), Hyaluronan-Mediated Motility Receptor (HMMR), tenascin C (TNC), fibronectin 1 (FN1), COL1A1, COL1A2, COL5A1, COL5A2, COL11A2, COL13A1, COL16A1, COL27A1, chondroitin sulfate proteoglycan 4 (CSPG4), laminin β3 (LAMB3), serglycin (SRGN), and SPARC. For assessing EMT suppression, these ECMs may be used singly or in combination as a marker.

For the capability of effectively assessing EMT suppression in RPE cells, the ECM is preferably at least one selected from the group consisting of COL5A3, COL6A3, laminin γ2 (LAMC2), Hyaluronan-Mediated Motility Receptor (HMMR), tenascin C (TNC), COL1A1, COL1A2, SRGN, FN1, COL5A2, COL13A1, and LAMB3, and more preferably at least one selected from the group consisting of COL5A3, COL6A3, laminin γ2 (LAMC2), Hyaluronan-Mediated Motility Receptor (HMMR), and tenascin C (TNC).

In the present description, a known epithelial marker can be used, and examples of the epithelial marker include, but not limited to, ID1, ID2, MUC1, cytokeratin 18 (KRT18), THBS1, VIL2, and E-cadherin (CDH1). These epithelial markers may be used singly or in combination.

In the present description, the EMT suppressive compound includes compounds and components that are known to have a suppressive activity on EMT in epithelial cells, besides zaltoprofen, oxaprozin, tiaprofenic acid, flufenamic acid, mefenamic acid, sulindac, epalrestat, zafirlukast, amlexanox, seratrodast, or a pharmaceutically acceptable salt thereof. Examples include, but not limited to, Alisertib, MK-0457 (Tozasertib), PHA-739358 (danusertib), AMG-900, Barasertib, CYC116, MLN8054, Baicalin, Baicalein, Lupeol, Istanbulin A, Phytol, Diphenyl difluoroketone (EF24), Crucmin, Phloroglucinol, Plumbagin, Rapamycin, FK506 (Tacrolimus), Thalidomide, LY550410, SB-505124, SD-208, TAPI-0, TAPI-1, JNJ-38877605, PF-04217903, AG1478 (Tyrphostin), Erlotinib, Gefitinib, Lapatinib, PD153035, PD158780, WHI-P154, BMS-536924, A83-01, D4476, LY-364947, SB-431542, SD-208, AZD6244 (Selumetinib), CI-1040, PD0325901, GDC-0941 (Pictilisib), PI-103, PIK-90, ZSTK474, API-2, AZD0530 (Saracatinib), PP1, 2-Hydroxycinnamaldehyde, 5-aza-dC, BI 5700, Celecoxib, CX-4945 (Silmitasertib), Disulfiram, Eribulinmesyate, Evodiamine, EW-7203, Fasudil, Nintedanib, Fuzheng Huayu recipe, Grape seed proanthocyanidins, Vorinostat, Herbimycin A, Entinostat, Honokiol, NPI-0052, Methacycline, Dasatinib, Ki26894, NSC 74859, NVP-LDE-225 (Erismodegib), Palbociclib, Pinocembrin, Salvianolic Acid B, Sorafenib, Resveratrol, S-Allylcysteine, Silibinin meglumine, Simvastatin, Centchroman, ML327, GN-25, Trichostatin A, Sarasinoside A1, Panobinostat, Danusertib, Cystatin C, Thymoquinone, Ulinastatin, Dendrofalconerol A (DF-A), ginsenoside (carrot saponin), staff tree seed extract, salicin (white willow extract), salicylic acid, hedge parsley extract, osthol, Muscadine grape skin extract, Tongxinluo, procyanidin C1 (cinnamon), ashwagandha root extract (Withania somnifera root extract), Qingyihuaji, roselle extract, gallic acid epigallocatechin, proanthocyanidin (grape seed extract), and Salvianolic acid B.

[Prophylactic and/or Therapeutic Agent for Exudative Age-Related Macular Degeneration]

Existing angiogenesis inhibitors that are used for Wet AMD are mostly pharmaceuticals using antibody, so that they have the problem of high medical costs. In a treatment of Wet AMD, in particular, angiogenesis occurs again upon withdrawal of the administration, and the risk of the blindness can increase. By using the present invention, it becomes possible to reduce the dose, dosing interval, and dosing frequency of an angiogenesis inhibitor, so that it is possible to expect the effect in terms of health care economics. It is also expected that suppression of EMT in RPE cells by the present invention prevents Dry AMD from transiting to Wet AMD, or provides radical treatment of AMD. Since it is possible to suppress EMT in RPE cells by the present invention, it is also possible to use the present invention as a VEGF production suppressor or a VEGF expression suppressor.

[EMT Induction Model]

The present inventors have developed a model of inducing EMT in vitro by a method including giving stimulation on epithelial cells. By using the EMT induction model, it becomes possible to assess the influence by EMT in a variety of epithelial cells. It also becomes possible to assess and/or screen whether a drug suppresses EMT in a variety of epithelial cells.

The epithelial cells are not particularly limited as long as they are known epithelial cells, however, from the view point of assessing the influence by EMT, preferably RPE cells, more preferably human RPE cells, further preferably ARPE-19 which is a strain of RPE cells are used as the epithelial cells. The EMT induction model using such RPE cells is capable of assessing EMT in gene expression, secretion of protein, mobility, Focus formation and the like.

Stimulation that is given to epithelial cells includes, but not limited to, stimulation by a drug, stimulation by a mechanical operation, and stimulation by an electric operation, and from the view point of capability of significantly inducing EMT, stimulation including bringing a drug into contact with cells is preferred. The drug is preferably, but not limited to, at least one selected from the group consisting of a cytokine, a growth factor, and a chemokine.

As the cytokine used for stimulation, a known substance can be used, and examples of the cytokine include interleukin 1β, (IL-1β), IL-4, IL-5, IL-6, IL-10, IL-12, IL-13, IL-16, tumor necrosis factor-α (TNF-α), and interferon γ (INF-γ). From the view point of capability of significantly inducing EMT, the cytokine is preferably at least one selected from the group consisting of IL-1β, IL-6, INF-γ, and TNF-α, more preferably at least one selected from the group consisting of IL-1β, IL-6, and TNF-α, and further preferably IL-1β and/or TNF-α. The cytokines may be used singly or in combination.

As a growth factor used for stimulation, known substances can be used, and examples of such a growth factor include transforming growth factor (TGF-β), fibroblast growth factors (FGFs), hepatocyte growth factor (HGF), epidermal growth factor (EGF), and platelet-based growth factor (PDGF). From the view point of capability of significantly inducing EMT, the growth factor is preferably at least one selected from the group consisting of TGF-β, EGF, and FGFs, and more preferably TGF-β and/or EGF. The growth factor may be used singly or in combination.

As the chemokine used for stimulation, a known substance can be used, and examples of such a chemokine include IL-8, macrophage inflammatory protein 1α (MIP-1α), monocyte chemoattractant protein-1 (MCP-1), RANTES (regulated on activation normal T cell expressed and secreted), and eotaxin. From the view point of capability of significantly inducing EMT, the chemokine is preferably at least one selected from the group consisting of MIP-1α, MCP-1, and RANTES, and more preferably MIP-1α and/or MCP-1. The chemokines may be used singly or in combination.

The stimulation can use, for example, a combination of at least one cytokine selected from the group consisting of IL-1β, IL-6, INF-γ, and TNF-α, at least one growth factor selected from the group consisting of TGF-β, EGF, and FGFs, and at least one chemokine selected from the group consisting of MIP-1α, MCP-1, and RANTES.

The concentration of a cytokine, a growth factor, or a chemokine in stimulation is, for example, preferably greater than or equal to 1 ng/mL, more preferably greater than or equal to 5 ng/mL, further preferably greater than or equal to 10 ng/mL, particularly preferably greater than or equal to 15 ng/mL, most preferably greater than or equal to 20 ng/mL, although it can be appropriately adjusted depending on the kind of the epithelial cells, the state of cells, the kind of the cytokine and so on. Also, the concentration of a cytokine, a growth factor, or a chemokine is preferably less than or equal to 1 µg/mL, more preferably less than or equal to 700 ng/mL, further preferably less than or equal to 500 ng/mL, particularly preferably less than or equal to 200 ng/mL, most preferably less than or equal to 100 ng/mL. Also, the concentration of a cytokine, a growth factor, or a chemokine is preferably 1 ng/mL to 1 µg/mL, more preferably 5 to 700 ng/mL, further preferably 10 to 500 ng/mL, particularly preferably 15 to 200 ng/mL, most preferably 20 to 100 ng/mL.

Although not limited to the following, when the cytokine is IL-1β, IL-4, IL-5, IL-6, IL-8, IL-10, IL-12, IL-13, or IL-16, the concentration of cytokine is preferably 1 ng/mL to 1 µg/mL, more preferably 5 to 700 ng/mL, further preferably 10 to 500 ng/mL, particularly preferably 15 to 200 ng/mL, most preferably 20 to 100 ng/mL.

Although not limited to the following, when the cytokine or the chemokine is INF-γ, TNF-α, MIP-1α, the concentration is preferably 10 ng/mL to 1 µg/mL, more preferably 20 to 800 ng/mL, further preferably 30 to 700 ng/mL, particularly preferably 40 to 600 ng/mL, most preferably 50 to 500 ng/mL.

Although not limited to the following, when the growth factor is TGF-β, EGF, the concentration of the growth factor is preferably 1 to 200 ng/mL, more preferably 2 to 100 ng/mL, further preferably 3 to 50 ng/mL, particularly preferably 4 to 600 ng/mL, most preferably 5 to 25 ng/mL.

The reaction time in stimulation can be for example, at least 5 minutes or longer although it can be appropriately adjusted depending on the kind of epithelial cells, the state of cells, the kind of cytokine and so on, and from the view point of losing the epithelial character and acquiring the mesenchymal character in EMT, the reaction time in stimulation is preferably at least 10 minutes or longer, more preferably at least 1 hour or longer, further preferably at least 10 hours or longer, particularly preferably at least 24 hours or longer, most preferably at least 48 hours or longer. The reaction time in stimulation can be, for example, within 120 hours, and from the view point of losing the epithelial character and acquiring the mesenchymal character in EMT, the reaction time in stimulation is preferably within 108 hours, more preferably within 96 hours, further preferably within 84 hours, particularly preferably within 72 hours, most preferably within 60 hours. The reaction time in stimulation can be, for example, 5 minutes to 120 hours, and from the view point of losing the epithelial character and acquiring the mesenchymal character in EMT, the reaction time in stimulation is preferably 10 minutes to 108 hours, more preferably 1 to 96 hours, further preferably 10 to 84 hours, particularly preferably 24 to 72 hours, most preferably 48 to 60 hours.

The reaction temperature in stimulation can be for example, 4 to 50° C., preferably 10 to 45° C., more preferably 20° C. to 40° C., further preferably 30 to 37° C., although it can be appropriately adjusted depending on the kind of epithelial cells, the state of cells, the kind of cytokine and so on.

Examples of the method for assessing whether EMT is induced in cells, include, but not limited to, measuring expression (secretion) of at least one selected from the group consisting of an epithelial marker, a mesenchymal marker and an ECM before and/or after stimulation to the epithelial cells; observing morphological change of cells; or measuring variation in mobility of cells. Although not limited to the following, when EMT is induced in RPE cells, the following phenomena are observed: the epithelial marker is suppressed; the mesenchymal marker is enhanced; the mobility is enhanced; and/or the cell morphology is deformed to fusiform, the cells agglutinate to form a drusen-like structure (Focus), and the like.

Expression of gene or expression or secretion of protein can be measured by a known method such as a microarray, a real-time PCR method, a PCR method, an Western blotting method, an ELISA method, or an immunohistological staining. Variation in mobility can be measured by a known method such as histological staining, e.g., Giemsa staining or an invasion assay method. For example, morphological change can be measured by a known method such as histological staining, e.g., HE staining.

[Assessment of CNV Suppression]

CNV suppression can be assessed in vitro by using an EMT induction model. That is, by comparing the expression amount of VEGF in the presence of a drug, and the expression amount of VEGF in the absence of a drug after induction of EMT in RPE cells, it is possible to assess the suppression of CNV by the drug suppressing expression of VEGF in RPE cells. Examples of measuring the state of EMT include measuring expression (secretion) of at least one selected from the group consisting of an epithelial marker, a mesenchymal marker, and an ECM. Suppression of EMT in RPE cells results in suppression of the mesenchymal marker and/or the ECM. Expression of the EMT marker or the VEGF can be assessed, for example, by an expression amount of mRNA.

The step of extracting RNA from cells can be achieved by using a known RNA extraction method. It is preferred to use a commercially available RNA extraction kit or the like.

The step of quantitatively analyzing expression of mRNA, is preferably, but not limited to, achieved by using a real-time PCR method. As the EMT marker measured in the real-time PCR method, the EMT markers such as an epithelial marker, a mesenchymal marker, or an ECM as described above can be used. From the view point of using an EMT marker capable of measuring with excellent reproducibility in the real-time PCR method, as the epithelial marker, ID1, ID2, MUC1, cytokeratin 18 (KRT18), THBS1, VIL2, or E-cadherin (CDH1) is preferred, and MUC1, cytokeratin 18 (KRT18), or E-cadherin (CDH1) is more preferred. As the mesenchymal marker, Snail, Slug, CDH3, MMP1, MMP7, MMP3, ZEB2, CDH2, or vimentin is preferred, and Snail, Slug, CDH3, MMP1, MMP7, or vimentin is more preferred. As the ECM, COL5A3, COL6A3, LAMC2, HMMR, TNC, COL1A1, COL1A2, CSPG4, SRGN, FN1, VIM, COL5A2, COL13A1, or LAMB3 is preferred, and COL5A3, COL6A3, LAMC2, HMMR, TNC, or FN1 is more preferred from the view point of using an EMT marker capable of measuring with excellent reproducibility in the real-time PCR method.

[Drusen Suppressor]

The drusen suppressor of the present invention contains a compound having an activity of suppressing epithelial-mesenchymal transition (EMT) in retinal pigment epithelial cells (RPE cells) as an active ingredient.

In the present description, "drusen" is an age-related change observed even in the healthy elderly, and refers to deposits existing under or around RPE cells. "Drusen" is histologically deposits of polymorphic substances in the collagen fiber layer between the basal lamina of RPE cells and the Bruch's membrane, and examples of the constituents of drusen include cellular components such as an organelle, cell membrane-like debris, non-esterified cholesterol, a complement, and a secretion of RPE cells. Deposits in the macula forming drusen include a basal laminar deposit that exists inside the basal lamina of RPE cells, and a basal linear deposit that exists outside the basal membrane of RPE cells as observed by an electron microscope.

According to one estimate, it is considered that drusen in human can be classified into hard drusen (less than or equal to 63 µm) and soft drusen (greater than or equal to 63 µm) according to the ophthalmoscopic finding. Soft drusen, when they are fused, are called confluent drusen, and drusen that are fused and expanded and accompanied by retinal pigment epithelial detachment (PED) are called Drusenoid PED. In recent years, it is reported that pseudodrusen that are classified as still another drusen influence on the prognosis and thus are clinically important. In the present description, "drusen" includes a deposit or a structure resembling drusen such as pseudodrusen. besides hard drusen and soft drusen.

According to the diagnostic criteria of AMD in Japan, soft drusen (greater than or equal to 63 µm) and abnormal RPE cells are included as precursor lesions. Conventionally, the mechanism of formation of drusen is not known, and thus it has been difficult to radically prevent or treat drusen. To complete the present invention, the present inventors obtained new findings that drusen are structures caused by occurrence of EMT in RPE cells.

The present inventors estimated that epithelial cells represented by RPE cells change their characters by external stimulation such as aging, UV light or the like, and acquire the characters having enhanced secretion of the extracellular matrix, and acquisition of mobility (this is called a mesenchymal character). This strongly infers that drusen is generated by transformation of retinal pigment epithelial cells occurring in the macula.

In light of the above, the present inventors ascertained by using a retinal pigment epithelial cell strain (ARPE-19) that transformation of cells results in acquisition of the character having enhanced secretion of the extracellular matrix, acquisition of mobility and the like, and final formation of an agglomerate (also referred to as Focus) comparable to drusen composed of cellular components and secretions thereof, and verified the developmental mechanism, and obtained conclusive evidence that this drusen-like structure (agglomerate (Focus)) developed in the same process is equivalent to drusen occurring in a living body.

In the present description, "drusen suppression" refers to reducing the number of formed drusen or breaking down formed drusen, or decreasing or preventing increase in size (appropriately defined by diameter, area, volume or the like) of formed drusen, and also includes preventing formation of new drusen. Although not limited to the following, when the number of formed drusen is reduced, for example, the number of drusen is reduced by at least 5% or more, preferably 10% or more, further preferably 20% or more, particularly preferably 30% or more, most preferably 40% or more, compared with the control that is not treated with a drug. The number of drusen can be assessed by a known method, and for example, by fundus photography. Although not limited to the following, when the size of formed drusen is decreased or prevented from increase, for example, at least the size of drusen remains unchanged, and preferably reduced by 5% or more, more preferably reduced by 10% or more, further preferably reduced by 20% or more, particularly preferably reduced by 30% or more, most preferably reduced by 40% or more, compared with the control that is not treated with a drug. The size of drusen can be assessed by a known method, for example, by fundus photography, spectral domain optical coherence tomography (SD-OCT) finding, fluorescent fundus contrast imaging by fluorescein, indocyanine green or the like. Although not limited to the following, when formation of new drusen is prevented, for example, formation of at least 5% or more, preferably 10% or more, further preferably 20% or more, particularly preferably 30% or more, most preferably 40% or more of new drusen is prevented, compared with the control that is not treated with a drug. Formation of new drusen can be assessed by a known method, for example, by fundus photography, fluorescent fundus contrast imaging or the like. Although the assessing method of drusen suppression is not particularly limited as long as it can provide proper assessment, it is preferred that synthetical assessment is made based on the number, thickness and volume of drusen.

Formation of drusen is correlated with progression of the clinical state of AMD, namely decrease in visual field or visual acuity. According to one estimate, it has been reported that as the number of drusen in the retina increases, and as the formation of individual drusen in the retina advances and the size increases, the clinical state of Dry AMD progresses and a symptom such as geographic atrophy is observed. Also, generation of drusen is accompanied by generation of a new blood vessel in the choroid under the drusen, and retinal edema that is characteristic of Wet AMD, and retention of subretinal fluid are observed. There is a report that the new blood vessel is fragile and there is a case that AMD transits from Dry AMD to Wet AMD upon rupture of the new blood vessel.

Also, it is known that expression of VEGF (vascular endothelial growth factor) which is an inducer of neovascularization, or VEGFR (vascular endothelial growth factor receptor) which is a receptor of VEGF is enhanced when EMT occurs in cells. However, according the new finding that drusen formation which is a clinical state of Dry AMD is caused by EMT, it is inferred that angiogenesis is induced also in Dry AMD as long as drusen is generated.

Accordingly, it is supposed that suppression of drusen leads to prophylaxis or therapy of Wet AMD besides prophylaxis or therapy of Dry AMD, and also leads to prophylaxis or therapy of angiogenesis in Dry AMD which is the previous stage before transition to Wet AMD.

Also, the present inventors have hypothesized that one factor in the case of very slow progression of AMD is a balance between newly generated drusen and broken down (suppressed) drusen. A detailed description will be given below. Although drusen are generated by age-related change even in a healthy subject, breakdown (suppression) is dominant, and the clinical state of AMD is difficult to progress as long as such a balance relation is maintained. However, when the equilibrium is upset in this balance relation, and generation of drusen becomes dominant to breakdown (suppression), drusen gradually remain, and the clinical state of AMD progresses. The present inventors speculate that the factor that strongly influences on this balance relation is EMT. To be more specific, while RPE cells keep the inherent epithelial character in a healthy subject in which EMT is suppressed, RPE cells lose the epithelial character and have the mesenchymal character when enhancement of EMT becomes dominant due to aging, external stimulation or the like. As shown in Examples below, generation of ECM such as collagen which is a constituent of drusen is enhanced in RPE cells having acquired the mesenchymal character. Meanwhile, in a living body, these ECMs are decomposed by a breakdown enzyme MMP (matrix metalloproteinases), however, expression of TIMP (tissue inhibitors of metalloproteinases) that suppresses the activity of MMP is also enhanced by the enhanced EMT. By suppression of the activity of MMP, ECM is not decomposed, and breakdown of drusen is suppressed. As a result, drusen are increased by enhancement of EMT, and AMD progresses.

Also by suppressing EMT, expression of ECM such as collagen which is a constituent of drusen is suppressed, and the activity of MMP or the like is significantly expressed due to the suppressed expression of TIMP, so that decomposition of ECM is promoted. As a result, generation of drusen is suppressed, and progression of AMD is suppressed, and also curing of AMD by significant breakdown of drusen is expected. The present inventors infer that in a living body, enhancement of EMT triggers the action of the suppressing mechanism by TIMP and makes generation of drusen dominant, and thus clinical state of AMD gradually progresses.

According to such an inferred mechanism of AMD progression, by suppressing excessive expression of a factor related with the mesenchymal character and/or letting the mechanism of drusen breakdown in a living body sufficiently function, by suppressing EMT by an external factor, it is possible to improve the balance relation between generation and breakdown of drusen. The present inventors have established a cell model capable of reproducing drusen in a living body, and assessed and screened a compound that suppresses EMT by using the cell model, and verified whether or not drusen are suppressed by the compound.

As to classification of AMD, classification into early AMD, intermediate AMD or late AMD, classification into non-progressive AMD or progressive AMD, and the like, besides general classification into Dry AMD and Wet AMD have been reported. In the present description, any classification can be a target for prophylaxis and/or therapy as long as it is AMD in which drusen is involved in development and exacerbation.

Classification of early AMD, intermediate AMD or late AMD is proposed by NIH (NIH Eligibility Categories: A Randomized, Placebo-Controlled, Clinical Trial of High-Dose Supplementation With Vitamins C and E, Beta Carotene, and Zinc for Age-Related Macular Degeneration and Vision Loss Arch Ophthalmol. 2001 October; 119 (10): 1417-1436). This classification classifies the category of AMD into No AMD (Category 1), early AMD (Category 2), intermediate AMD (Categories 3a, 3b), late AMD (Categories 4a, 4b) according to the size of drusen (Drusen Size), the area of drusen (Drusen Area), and the pigment abnormality (Pigment Abnormalities) in one eye, and symptoms of the other eye.

No AMD (Category 1) refers to the case where the drusen is absent or small in size (less than 63 µm), the drusen area is less than a circle having a diameter of 125 µm (5 to 15 drusen), and the pigment abnormality is absent in one eye, and the same symptom is observed in the other eye. According to this classification, also in No AMD (Category 1), drusen are generated, so that this category can be a target for prophylaxis and/or therapy by the drusen suppressor according to the present invention.

It is inferred that in early AMD or intermediate AMD that are classified as symptoms in which the drusen size and area are further increased, the drusen suppressor of the present invention is used more effectively.

On the basis of the new finding that drusen are structures caused by EMT occurring in RPE cells, it can be understood that drusen are suppressed by suppressing EMT in RPE cells.

The compound having EMT suppressive activity in RPE cells (also referred to as EMT suppressive compound in the present description) includes compounds that are known for the suppressive activity against EMT in epithelial cells as described above. Examples of the compound that suppress EMT in RPE cells include compounds for which suppression of EMT is recognized by using an EMT induction model in an RPE cell strain that is newly found in the present invention.

The EMT suppressive compound can be, but not limited to, a drug that suppresses expression of a mesenchymal marker or an extracellular matrix (ECM).

In the drusen suppressor of the present invention, the EMT suppressive compound can be, but not limited to, a nonsteroidal anti-inflammatory drug, an aldose reductase inhibitor, a leukotriene receptor antagonist, a chemical mediator release suppressor, and/or a thromboxane A2 receptor antagonist.

Examples of the nonsteroidal anti-inflammatory drug (NSAIDs) include, but not limited to, propionic acid-based NSAIDs such as oxaprozin, zaltoprofen, pranoprofen, alminoprofen, benoxaprofen, bermoprofen, bucloxic acid, carprofen, ibuprofen, ibuproxam, indoprofen, ketoprofen, tiaprofenic acid, naproxen, flunoxaprofen, flurbiprofen, flurbiprofen axetil, fenoprofen calcium, naproxen, piketoprolen, pirprofen, protizinic acid, suprofen, tiaprofen, ximoprofen, and loxoprofen sodium; aryl acetic acid-based NSAIDs such as aceclofenac, acemetacin, alclofenac, amfenac sodium, amtolmetin guacil, bufexamac, cinmetacin, clopirac, felbinac, fenclozic acid, fentiazac, glucametacin, ibufenac, indometacin, indometacin farnesil, isofezolac, isoxepac, lonazolac, metiazinic acid, oxametacin, pirazolac, proglumetacin, tiaramide, tolmetin, tropesin, zomepirac, etodolac, diclofenac sodium, sulindac, nabumetone, fenbufen, proglumetacin maleate, and mofezolac; aminoaryl carboxylic acid-based NSAIDs such as enphenamic acid, etofenamate, flufenamic acid, isonixin, meclofenamic acid, flufenamic acid aluminum, mefenamic acid, niflumic acid, talniflumate, terofenamate, and tolfenamic acid; aryl butyric acid-based NSAIDs such as bumadizone, butibufen, fenbufen, and xenbucin; aryl carboxylic acid-based NSAIDs such as clidanac, ketorolac, and tinoridine; salicylic acid-based NSAIDs such as acetaminosalol, benorylate, bromosaligenin, calcium acetylsalicylate, diflunisal, etersalate, fendosal, gentisic acid, glycol salicylate, imidazole salicylate, lysine acetylsalicylate, mesalazine, morpholine salicylate, 1-naphthyl salicylate, olsalazine, parsalmide, phenyl acetylsalicylate, phenyl salicylate, salacetamide, salicylamide O-acetic acid, salicylsulfuric acid, salsalate, and sulfasalazine; fenamic acid-based NSAIDs such as mefenamic acid, flufenamic acid, and tolfenamic acid; pyrimidine-based NSAIDs such as bucolome; oxicam-based NSAIDs such as ampiroxicam, tenoxicam, piroxicam, meloxicam, lornoxicam, droxicam, and isoxicam; pyrazole-based NSAIDs such as epirizole, and difenamizole; pyrazolone-based NSAIDs such as apazone, benzpiperylone, feprazone, mofebutazone, morazone, oxyphenbutazone, phenylbutazone, pipebuzone, propyphenazone, ramifenazone, suxibuzone, and thiazolinobutazone; basic NSAIDs such as tiaramide hydrochloride, and emorfazone, or pharmaceutically acceptable salts thereof. These NSAIDs may be used singly or in combination of two or more kinds. As these NSAIDs, either the one synthesized by a known method or a commercially available product may be used.

Among these NSAIDs, from the view point of exerting significant EMT suppressive effect, propionic acid-based NSAIDs, aminoaryl carboxylic acid-based NSAIDs or aryl acetic acid-based NSAIDs are preferred, propionic acid-based NSAIDs, fenamic acid-based NSAIDs or aryl acetic acid-based NSAIDs are more preferred, at least one selected from the group consisting of zaltoprofen, oxaprozin, tiaprofenic acid, ibuprofen, flurbiprofen, flufenamic acid, mefenamic acid, sulindac, and pharmaceutically acceptable salts thereof is more preferred, and at least one selected from the group consisting of zaltoprofen, oxaprozin, flufenamic acid, mefenamic acid and pharmaceutically acceptable salts thereof is further preferred.

Examples of the aldose reductase inhibitor include, but not limited to, epalrestat, zenarestat, statil, and sorbinil. These aldose reductase inhibitors may be used singly or in combination of two or more kinds. As these aldose reductase inhibitors, either the one synthesized by a known method or a commercially available product may be used.

Among these aldose reductase inhibitors, from the view point of exerting significant EMT suppressive effect, epalrestat and/or a pharmaceutically acceptable salt thereof is preferred.

Examples of the leukotriene receptor antagonist include, but not limited to, antagonists of cysteinyl leukotriene type 1 (CysLT1) receptor, such as zafirlukast, montelukast, and pranlukast, and 5-lipoxygenase inhibitors such as zileuton. These leukotriene receptor antagonists may be used singly or in combination of two or more kinds. As these leukotriene receptor antagonists, either the one synthesized by a known method or a commercially available product may be used.

Among these leukotriene receptor antagonists, from the view point of exerting significant EMT suppressive effect, antagonists of cysteinyl leukotriene type 1 (CysLT1) receptor such as zafirlukast, montelukast, and pranlukast are preferred, at least one selected from the group consisting of zafirlukast, montelukast, pranlukast, and pharmaceutically acceptable salts thereof is more preferred, and zafirlukast and/or a pharmaceutically acceptable salt thereof is further preferred.

Examples of the chemical mediator release suppressor include, but not limited to, amlexanox, sodium cromoglicate, pemirolast potassium, and ibudilast. These chemical mediator release suppressors may be used singly or in combination of two or more kinds. As these chemical mediator release suppressors, either the one synthesized by a known method or a commercially available product may be used.

Among these chemical mediator release suppressors, from the view point of exerting significant EMT suppressive effect, amlexanox and/or a pharmaceutically acceptable salt thereof is preferred.

Examples of the thromboxane A2 antagonist include, but not limited to, a thromboxane A2 receptor antagonist and a thromboxane A2 synthase inhibitor. Examples of the thromboxane A2 receptor antagonist include seratrodast or ramatroban, and examples of the thromboxane A2 synthase inhibitor include ozagrel hydrochloride. These thromboxane A2 antagonists may be used singly or in combination of two or more kinds. As these thromboxane A2 antagonists, either the one synthesized by a known method or a commercially available product may be used.

Among these thromboxane A2 antagonists, from the view point of exerting significant EMT suppressive effect, seratrodast and/or a pharmaceutically acceptable salt thereof is preferred.

[Prophylactic and/or Therapeutic Agent for Age-Related Macular Degeneration]

The drusen suppressor of the present invention is mainly used as a prophylactic and/or therapeutic agent for age-related macular degeneration. Such a prophylactic and/or therapeutic agent for age-related macular degeneration contains a propionic acid-based nonsteroidal anti-inflammatory drug, an aminoaryl carboxylic acid-based nonsteroidal anti-inflammatory drug, an aryl acetic acid-based nonsteroidal anti-inflammatory drug, an aldose reductase inhibitor, a leukotriene receptor antagonist, a chemical mediator release suppressor, or a thromboxane A2 receptor antagonist as an active ingredient, and as the aldose reductase inhibitor, epalrestat and/or a pharmaceutically acceptable salt thereof can be used. Such active ingredients follow the ingredients as described in the item of [Drusen suppressor].

[Combination Use with Angiogenesis Inhibitor]

In the present invention, it is possible to provide a prophylactic and/or therapeutic agent for AMD including a combination of an angiogenesis inhibitor and a drusen suppressor of the present invention.

In the present description, "angiogenesis inhibitor" refers to a drug having the effect of preventing angiogenesis, a drug having the effect of preventing exacerbation of angiogenesis, or a drug having the effect of reducing a formed new blood vessel or making a formed new blood vessel disappear. Examples of the angiogenesis inhibitor include, but not limited to an anti-VEGF antibody or a fragment (Fab fragment, a single-stranded variable fragment (scFv) etc.) thereof, a fusion protein of a fragment of an anti-VEGF antibody and a Fc domain of an IgG molecule, and an anti-angiogenesis aptamer (RNA aptamer etc.). As the angiogenesis inhibitor, commercially available known angiogenesis inhibitors, including, but not limited to bevacizumab (AVASTIN (registered trademark)), ranibizumab (LUCENTIS (registered trademark)), aflibercept (EYLEA (registered trademark)), pegaptanib sodium (MACUGEN (registered trademark)), ESBA-1008, lampalizumab, MC-1101, doxycycline hyclate, and emixustat hydrochloride can be used. Specifically, the EMT suppressive compound, and the angiogenesis inhibitor can be combined appropriately in general consideration of the symptom or condition of the patient, the expected therapeutic effect and so on.

In AMD, it is known that angiogenesis occurs in the choroid under formed drusen, and it is inferred that inhibition of angiogenesis under drusen, combined with suppression of drusen can give an excellent prophylactic and/or therapeutic effect for AMD. As a classification where angiogenesis occurs in AMD, Wet AMD, early and/or intermediate AMD can be recited. In early and/or intermediate AMD, it is inferred that a fragile new blood vessel is generated in addition to that the number and the size of drusen are increased. Also in Dry AMD, it is inferred that angiogenesis is induced when drusen are generated. Exudation of blood components from the fragile new blood vessel, or breakage of the fragile vessel cause rapid progression of transition to Wet AMD. Also, it is considered to be important to start the therapy prophylactically in early AMD during which a fragile blood vessel can arise merely minutely. Therefore, in the present invention, the drusen suppressor is used preferably for prophylaxis and/or therapy for Wet AMD, more preferably for prophylaxis and/or therapy for intermediate AMD, further preferably for prophylaxis and/or therapy for early and/or intermediate AMD by being used in combination with an angiogenesis inhibitor.

By using the drusen suppressor of the present invention as a concomitant drug, it becomes possible to reduce the dose, dosing interval, and dosing frequency of an angiogenesis inhibitor, so that it is possible to expect the effect in terms of health care economics.

In one embodiment, the drusen suppressor of the present invention can be used for therapy in combination with a photodynamic therapy (PDT). While a drug such as Verteporfin that selectively migrates to a new blood vessel is used in the photodynamic therapy, normal choroid is known to be injured to some extent by laser irradiation. Therefore, by using the drusen suppressor of the present invention while reducing the dose of the drug such as Verteporfin, and the time or dose of irradiation by laser in the photodynamic therapy, it is possible to effectively prevent and/or treat AMD.

In one embodiment, the drusen suppressor of the present invention can also be used for prophylaxis and/or therapy for AMD by appropriately combining the angiogenesis inhibitor and the photodynamic therapy.

Since the EMT induction model using RPE cells as described in the item of [EMT induction model] shows the characters similar to those of drusen in AMD in terms of gene expression, secretion of protein, mobility, Focus formation and so on, it can be effectively used as a cell model in AMD.

[Method for Assessing or Screening Test Substance]

Drug sensitivity can be assessed in vitro by using the EMT induction model as described above. Further, the EMT induction model of the present invention is useful for assessment or screening of a drusen suppressor.

Although not limited to the following, assessment or screening of a drug can be conducted, for example, by reproducing drusen in vitro by EMT induction model of RPE cells, and bringing such a drusen-like structure into contact with a test drug in the presence of various concentrations of the test drug or in the absence of the test drug, and measuring the state of the drusen-like structure and comparing the states before and after addition of the drug. The assessment or screening of a drug can also be conducted by inducing EMT in RPE cells in the presence or absence of a drug, and measuring and comparing the state of the drusen-like structure in the presence or absence of the drug. Examples of measurement of the state of the drusen-like structure include measuring expression (secretion) of at least one selected from the group consisting of an epithelial marker, a mesenchymal marker, and an ECM, measuring the morphological change of the cells, or measuring the variation in mobility of the cells. When EMT in RPE cells is suppressed, the following phenomena are observed: the mesenchymal marker and/or ECM is suppressed, the mobility is suppressed, and/or the cell morphology is deformed from fusiform to a cubic form, and formation of a drusen-like structure (Focus) is suppressed.

When a drug is assessed and/or screened by the degree of formation of the drusen-like structure (Focus), it can be achieved by a method including, but not limited to, inducing EMT in RPE cells using an EMT induction model; bringing the RPE cells into contact with a test drug to cause them to react with each other; and measuring formation of a drusen-like structure (focus) in the cells. In one embodiment, inducing EMT in RPE cells using an EMT induction model, and bringing the RPE cells into contact with a test drug to cause them to react with each other can be conducted simultaneously. In one embodiment, the aforementioned method can also include fixing the cells after the contact reaction.

The step of bringing the RPE into contact with a test drug to cause them to react with each other includes reacting the test drug stepwise in concentrations of the test drug from low concentrations to high concentration. The concentration of the test drug can be, for example, 0 µM (in the absence, without addition) to 500 µM, may be 0.1 to 400 µM, or may be 0.5 to 300 µM although it can be appropriately adjusted depending on the kind of the drug or the like.

The contact reaction time between the RPE cells and the test drug can be, for example, 5 minutes to 120 hours, and from the view point of sufficiently suppressing the mesenchymal character by suppression of EMT, it is preferably 10 minutes to 108 hours, more preferably 1 to 96 hours, further preferably 10 to 84 hours, particularly preferably 24 to 72 hours, most preferably 48 to 60 hours.

The contact reaction temperature between the RPE cells and the test drug, can be, for example, 4 to 50° C., preferably 10 to 45° C., more preferably 20° C. to 40° C., further preferably 30 to 37° C. although it can be appropriately adjusted depending on the kind of the drug or the like.

In the step of fixing the cells after the contact reaction, a known method can be used as the method of fixing the cells. Although not limited to the following, the cells can be fixed, for example, by using paraformaldehyde.

The step of measuring formation of a drusen-like structure (Focus) in cells can further include staining the cells, and/or analyzing a formation rate or a formation suppressing rate of a drusen-like structure (Focus).

As the staining of cells, a known staining method can be used without limitation, however, fluorescent staining is preferred, and a nuclear staining and/or actin staining by a fluorescent substance is more preferred. As the nuclear staining, for example, 7-AAD (7-aminoactinomycin D), Acridine Orange, DAPI, DMAO, Ethidium Bromide, Hoechst, Propidium Iodide (PI) and the like can be recited, and from the view point of stainability, Hoechst is preferred. As the actin staining, for example, phalloidin is preferably used.

Analysis of a formation rate or a formation suppressing rate of a drusen-like structure (Focus) includes, for example, imaging and digitizing a formation state of a drusen-like structure (Focus) without addition of a candidate drug, and a formation state of a drusen-like structure (Focus) when a specific concentration of a candidate drug is added. Further, the analysis also includes calculating a formation rate or a formation suppressing rate of a drusen-like structure (Focus) by comparing the numerical data of these cases. While the formation state of the drusen-like structure (Focus) can be imaged and digitized by a known imaging technique and digitizing technique, for example, it is possible to use a diameter, an area, a volume and the like of the drusen-like structure (Focus) as an index, and from the viewpoint of conducting analysis with higher accuracy and higher reproducibility, it is preferred to measure and digitize the volume of the drusen-like structure (Focus), and it is also preferred to digitize the drusen-like structure (Focus) by generally assessing the number, the thickness, and the volume of the drusen-like structure (Focus).

Assessment and/or screening of a drug by suppression of a mesenchymal marker and/or an ECM can be achieved by a method including, but not limited to, inducing EMT in RPE cells using an EMT induction model; bringing the RPE cells into contact with a test drug to cause them to react with each other; extracting RNA from the cells after the contact reaction; and quantitatively assaying expression of mRNA. In one embodiment, inducing EMT in RPE cells using an EMT induction model, and bringing the RPE cells into contact with a test drug to cause them to react with each other can be conducted simultaneously.

The step of inducing EMT in RPE cells using an EMT induction model, and the step of bringing the RPE cells into contact with a test drug to cause them to react with each other follow the item of the degree of formation of drusen-like structure (Focus).

The step of extracting RNA from cells after contact reaction can be achieved by using a known RNA extraction method. It is preferred to use a commercially available RNA extraction kit or the like.

The step of quantitatively analyzing expression of mRNA, is preferably, but not limited to, achieved by using a real-time PCR method. As the EMT marker measured in the real-time PCR method, the EMT markers such as a mesenchymal marker, or an ECM as described above in the item of drusen suppressor can be used. From the view point of using an EMT marker capable of measuring with excellent reproducibility in the real-time PCR method, as the mesenchymal marker, Snail, Slug, CDH3, MMP1, MMP7, MMP3, ZEB2, CDH2, or Snail, Slug, CDH3, MMP1, or MMP7 is more preferred. As the ECM, COL5A3, COL6A3, LAMC2, HMMR, TNC, COL1A1, COL1A2, CSPG4, SRGN, FN1, VIM, COL5A2, COL13A1, or LAMB3 is preferred, and COL5A3, COL6A3, LAMC2, HMMR, or TNC is more preferred from the view point of using an EMT marker capable of measuring with excellent reproducibility in the real-time PCR method.

When a drug is assessed and/or screened by suppression of mobility, it can be achieved by a method including, but not limited to, inducing EMT in RPE cells using an EMT induction model; bringing the RPE cells into contact with a test drug to cause them to react with each other; collecting the cells after the contact reaction; and conducting an invasion assay using the collected cells. In one embodiment, inducing EMT in RPE cells using an EMT induction model, and bringing the RPE cells into contact with a test drug to cause them to react with each other can be conducted simultaneously.

The step of inducing EMT in RPE cells using an EMT induction model, and the step of bringing the RPE cells into contact with a test drug to cause them to react with each other follow the item of the degree of formation of drusen-like structure (Focus).

The cells after the contact reaction can be collected by a known method, and assessed for the mobility by using a commercially available invasion assay kit. Assessment of mobility can be conducted by image analysis of migration (invasion) of the cells and/or by counting the number of invasive cells.

Here the test drug to be assessed may be a known compound having an epithelial-mesenchymal transition suppressing activity, or may be a compound that is not known to have an epithelial-mesenchymal transition suppressing activity. Further, the test drug may be a newly synthesized compound.

[Preparations]

The present invention is formulated into a dosage form suited for administration together with an additive as necessary. For example, the present invention can be provided in a dosage form suited for oral administration, such as a tablet, a capsule, a syrup, fine granules, granules, powder, or a pill. The present invention can also be provided in a dosage form suited for parenteral administration, such as injections, ophthalmic preparations, or patches. The present invention can also be provided as a preparation employing a drug delivery system, besides the foregoing preparations.

While the dose of the prophylactic and/or therapeutic agent for choroidal neovascularization or the drusen suppressor in the present invention can vary depending on the kind of the target disease, the age and the body weight of the patient, the indication and the dosage form thereof, for example, the adult daily dose is about 1 mg to about 1000 mg for a single to several doses in the case of an injection. In the case of oral administration, an adult daily dose of generally 0.01 to 10000 mg, preferably 0.1 to 5000 mg, more preferably 0.5 to 2500 mg can be administered once or in several batches daily, and in the case of an injection, an adult dose of generally 0.0001 to 2000 mg can be administered once or in several batches. In the case of drops or inserts, those having an active ingredient concentration of 0.000001 to 10% (w/v), preferably 0.00001 to 1% (w/v), more preferably 0.0001 to 0.1% (w/v) can be administered once or several times daily. Further, in the case of a patch, a patch containing 0.0001 to 2000 mg for adult can be applied.

In the present description, "Cmax" refers to a maximum plasma concentration of drug obtained in intervals between dosages. For existing drugs, Cmax can be obtained from the interview form or the package insert of the drug. Cmax is achieved at about 1 to about 48 hours, about 1 to about 20 hours, about 1 to about 18 hours, about 1 to about 16 hours, about 1 to about 12 hours, about 1 to about 10 hours, about 1 to about 8 hours, about 1 to about 6 hours, or about 1 to 4 hours after administration.

Although not limited to the following, an adult daily dose in the case of using zaltoprofen as an active ingredient is preferably 25 to 360 mg, more preferably 50 to 300 mg, further preferably 70 to 260 mg, particularly preferably 80 to 240 mg, most preferably 80 mg. In the case of as-needed use, the dose of zaltoprofen can be 80 to 160 mg daily. The dose of zaltoprofen can be 240 mg daily at a maximum. Cmax in the case of zaltoprofen is 20.4 µM ("Japanese Pharmacopoeia, zaltoprofen tablet, nonsteroidal painkilling anti-inflammatory agent, Soluirubin (registered trademark) tablet 80", Pharmaceutical Interview Form, April 2012 (the revised fourth edition), in the case of single-dose administration). The dose of zaltoprofen is preferably an administration amount with which Cmax of greater than or equal to about 20.4 µM is achieved, and as long as the effect of the present invention is exerted, the dose can be such an administration amount that achieves a blood concentration of greater than or equal to ½ amount of Cmax, or greater than or equal to ¼ amount of Cmax. Also, Cmax of zaltoprofen can be 16.8 µM depending on the kind of the additive to be mixed ("Nonsteroidal painkilling anti-inflammatory agent, Soleton tablet (registered trademark) 80, Japanese Pharmacopoeia, zaltoprofen tablet", Pharmaceutical Interview Form, revised in August 2015 (the sixth edition), in the case of single-dose administration). In this case, the dose of zaltoprofen is preferably an administration amount with which Cmax of greater than or equal to about 16.8 μM is achieved, and as long as the effect of the present invention is exerted, the dose can be such an administration amount that achieves a blood concentration of greater than or equal to ½ amount of Cmax, or greater than or equal to ¼ amount of Cmax. From the view point of achieving the aforementioned Cmax, a daily dose of zaltoprofen can be 240 to 360 mg, 240 to 300 mg, or 240 to 260 mg. From the viewpoint of achieving a blood concentration of greater than or equal to ½ amount of the aforementioned Cmax, a daily dose of zaltoprofen can be 120 to 360 mg, 120 to 300 mg, 120 to 260 mg, 120 to 240 mg, 120 to 220 mg, 120 to 200 mg, or 120 to 180 mg. From the view point of achieving a blood concentration of ¼ amount or more of the aforementioned Cmax, a daily dose of zaltoprofen can be 60 to 360 mg, 60 to 300 mg, 60 to 260 mg, 60 to 240 mg, 60 to 200 mg, 60 to 160 mg, 60 to 120 mg, or 60 to 80 mg. The aforementioned administration is preferably by an injection or by oral administration. By achieving the aforementioned blood concentration, it is expected that zaltoprofen passes through BRB and effectively suppresses CNV or drusen.

Although not limited to the following, an adult daily dose in the case of using oxaprozin as an active ingredient is preferably 100 to 700 mg, more preferably 200 to 600 mg, further preferably 300 to 500 mg, particularly preferably 400 mg. The maximum plasma concentration of drug (Cmax) is calculated by a known method, and in the case of oxaprozin, Cmax is 340.9 μM ("Long acting anti-inflammatory painkilling agent, Alvo (registered trademark) tablet 100 mg, Alvo (registered trademark) tablet 200 mg, oxaprozin preparation", Pharmaceutical Interview Form, November 2011 (the revised third edition in new form), in the case of repeated-dose administration). The dose of oxaprozin is preferably an administration amount with which Cmax of greater than or equal to about 340.9 μM is achieved, and as long as the effect of the present invention is exerted, the dose can be such an administration amount that achieves a blood concentration of greater than or equal to ½ amount of Cmax, or greater than or equal to ¼ amount of Cmax. From the view point of achieving the aforementioned Cmax, a daily dose of oxaprozin can be 400 to 700 mg, or 400 to 600 mg. From the view point of achieving a blood concentration of greater than or equal to ½ amount of the aforementioned Cmax, a daily dose of oxaprozin can be 200 to 700 mg, 200 to 600 mg, 200 to 500 mg, 200 to 400 mg, or 200 to 300 mg. From the view point of achieving a blood concentration of ¼ amount or more of the aforementioned Cmax, a daily dose of oxaprozin can be 100 to 700 mg, 100 to 600 mg, 100 to 500 mg, 100 to 400 mg, 100 to 300 mg, or 100 to 150 mg. The aforementioned administration is preferably by an injection or by oral administration. By achieving the aforementioned blood concentration, it is expected that oxaprozin passes through BRB and effectively suppresses CNV or drusen.

Although not limited to the following, an adult daily dose in the case of using tiaprofenic acid as an active ingredient is preferably 60 to 900 mg, more preferably 100 to 800 mg, further preferably 150 to 700 mg, particularly preferably 200 mg to 600 mg, most preferably 600 mg. In the case of as-needed use, the dose of tiaprofenic acid can be 200 mg daily. The dose of tiaprofenic acid can be 600 mg daily at a maximum. Cmax in the case of tiaprofenic acid is 69.15 μM ("Painkilling anti-inflammatory agent, Surgam (registered trademark) tablet 100 mg, 200 mg", Pharmaceutical Interview Form, revised in August 2014, (the revised fifth edition), in the case of single-dose administration). The dose of tiaprofenic acid is preferably an administration amount with which Cmax of greater than or equal to about 69.15 μM is achieved, and as long as the effect of the present invention is exerted, the dose can be such an administration amount that achieves a blood concentration of greater than or equal to ½ amount of Cmax, or greater than or equal to ¼ amount of Cmax. From the viewpoint of achieving the aforementioned Cmax, a daily dose of tiaprofenic acid can be 600 to 900 mg, 600 to 800 mg, or 600 to 700 mg. From the view point of achieving a blood concentration of greater than or equal to ½ amount of the aforementioned Cmax, a daily dose of tiaprofenic acid can be 300 to 900 mg, 300 to 800 mg, 300 to 700 mg, 300 to 600 mg, 300 to 500 mg, or 300 to 400 mg. From the view point of achieving a blood concentration of ¼ amount or more of the aforementioned Cmax, a daily dose of tiaprofenic acid can be 150 to 900 mg, 150 to 800 mg, 150 to 700 mg, 150 to 600 mg, 150 to 500 mg, 150 to 400 mg, 150 to 300 mg, 150 to 250 mg, or 150 to 200 mg. The aforementioned administration is preferably by an injection or by oral administration. By achieving the aforementioned blood concentration, it is expected that tiaprofenic acid passes through BRB and effectively suppresses CNV or drusen.

Although not limited to the following, an adult daily dose in the case of using flufenamic acid aluminum as an active ingredient is preferably 75 to 1250 mg, more preferably 150 to 1000 mg, further preferably 200 to 800 mg, particularly preferably 250 to 750 mg, most preferably 375 to 750 mg. In the case of as-needed use, the dose of flufenamic acid aluminum can be 250 mg daily. The dose of flufenamic acid aluminum can be 750 mg daily at a maximum. Cmax in the case of flufenamic acid aluminum is 27.91 μM ("Nonsteroidal anti-inflammatory painkilling antipyretic agent, OPYRIN (registered trademark) tablet 125 mg", Pharmaceutical Interview Form, prepared in December 2011 (the revised fourth edition in new form), in the case of single-dose administration). The dose of flufenamic acid aluminum is preferably an administration amount with which Cmax of greater than or equal to about 27.91 μM is achieved, and as long as the effect of the present invention is exerted, the dose can be such an administration amount that achieves a blood concentration of greater than or equal to ½ amount of Cmax, or greater than or equal to ¼ amount of Cmax. From the view point of achieving the aforementioned Cmax, a daily dose of flufenamic acid aluminum can be 750 to 1250 mg, 750 to 1000 mg, or 750 to 800 mg. From the view point of achieving a blood concentration of greater than or equal to ½ amount of the aforementioned Cmax, a daily dose of flufenamic acid aluminum acid can be 400 to 1250 mg, 400 to 1000 mg, 400 to 800 mg, 400 to 750 mg, or 400 to 500 mg. From the view point of achieving a blood concentration of ¼ amount or more of the aforementioned Cmax, a daily dose of flufenamic acid aluminum can be 200 to 1250 mg, 200 to 1000 mg, 200 to 800 mg, 200 to 500 mg, 200 to 400 mg, 200 to 300 mg, or 200 to 250 mg. The aforementioned administration is preferably by an injection or by oral administration. By achieving the aforementioned blood concentration, it is expected that flufenamic acid aluminum passes through BRB and effectively suppresses CNV or drusen.

Although not limited to the following, an adult daily dose in the case of using mefenamic acid as an active ingredient is preferably 150 to 2250 mg, more preferably 250 to 1800 mg, further preferably 400 to 1600 mg, particularly preferably 500 to 1500 mg, most preferably 1000 to 1500 mg. In the case of as-needed use, the dose of mefenamic acid can be 500 mg daily. The dose of mefenamic acid can be 1500 mg daily at a maximum. Cmax in the case of mefenamic acid is 38.54 µM ("Painkilling anti-inflammatory antipyretic agent, Pontal (registered trademark) tablet 250 mg", Pharmaceutical Interview Form, revised in July 2015, (the ninth edition), in the case of single-dose administration). The dose of mefenamic acid is preferably an administration amount with which Cmax of greater than or equal to about 38.54 µM is achieved, and as long as the effect of the present invention is exerted, the dose can be such an administration amount that achieves a blood concentration of greater than or equal to ½ amount of Cmax, or greater than or equal to ¼ amount of Cmax. From the viewpoint of achieving the aforementioned Cmax, a daily dose of mefenamic acid can be 1000 to 2250 mg, 1000 to 1800 mg, 1000 to 1600 mg, 1000 to 1500 mg, or 1000 to 1200 mg. From the view point of achieving a blood concentration of greater than or equal to ½ amount of the aforementioned Cmax, a daily dose of mefenamic acid can be 500 to 2250 mg, 500 to 1800 mg, 500 to 1600 mg, 500 to 1500 mg, 500 to 1200 mg, 500 to 1000 mg, or 500 to 800 mg. From the view point of achieving a blood concentration of ¼ amount or more of the aforementioned Cmax, a daily dose of mefenamic acid can be 150 to 2250 mg, 250 to 1800 mg, 250 to 1600 mg, 250 to 1500 mg, 250 to 1200 mg, 250 to 1000 mg, 250 to 800 mg, 250 to 500 mg, or 250 to 300 mg. The aforementioned administration is preferably by an injection or by oral administration. By achieving the aforementioned blood concentration, it is expected that mefenamic acid passes through BRB and effectively suppresses CNV or drusen.

Although not limited to the following, an adult daily dose in the case of using sulindac as an active ingredient is preferably 30 to 500 mg, more preferably 100 to 450 mg, further preferably 200 to 400 mg, particularly preferably 250 to 350 mg, most preferably 300 mg. Cmax in the case of sulindac is 10.10 µM ("Nonsteroidal anti-inflammatory painkilling agent, Clinoril (registered trademark) tablet 50, 100", Pharmaceutical Interview Form, revised in March 2011, (the revised third edition), in the case of single-dose administration). The dose of sulindac is preferably an administration amount with which Cmax of greater than or equal to about 10.10 µM is achieved, and as long as the effect of the present invention is exerted, the dose can be such an administration amount that achieves a blood concentration of greater than or equal to ½ amount of Cmax, or greater than or equal to ¼ amount of Cmax. From the view point of achieving the aforementioned Cmax, a daily dose of sulindac can be 300 to 500 mg, 300 to 450 mg, 300 to 400 mg, or 300 to 350 mg. From the view point of achieving a blood concentration of greater than or equal to ½ amount of the aforementioned Cmax, a daily dose of sulindac can be 200 to 500 mg, 200 to 450 mg, 200 to 400 mg, 200 to 350 mg, 200 to 300 mg, or 200 to 250 mg. From the view point of achieving a blood concentration of ¼ amount or more of the aforementioned Cmax, a daily dose of sulindac can be 100 to 500 mg, 100 to 450 mg, 100 to 400 mg, 100 to 350 mg, 100 to 300 mg, 100 to 250 mg, or 100 to 200 mg. The aforementioned administration is preferably by an injection or by oral administration. By achieving the aforementioned blood concentration, it is expected that sulindac passes through BRB and effectively suppresses CNV or drusen.

Although not limited to the following, an adult daily dose in the case of using epalrestat as an active ingredient is preferably 10 to 400 mg, more preferably 50 to 300 mg, further preferably 100 to 200 mg, particularly preferably 150 mg. Cmax in the case of epalrestat is 12.2 µM ("Aldose reductase inhibitor, Japanese Pharmacopoeia, epalrestat tablet, KINEDAK (registered trademark) tablet 50 mg", Pharmaceutical Interview Form, revised in November 2013 (the sixth edition), in the case of single-dose administration). The dose of epalrestat is preferably an administration amount with which Cmax of greater than or equal to about 12.2 µM is achieved, and as long as the effect of the present invention is exerted, the dose can be such an administration amount that achieves a blood concentration of greater than or equal to ½ amount of Cmax, or greater than or equal to ¼ amount of Cmax. From the view point of achieving the aforementioned Cmax, a daily dose of epalrestat can be 150 to 400 mg, 150 to 300 mg, or 150 to 200 mg. From the viewpoint of achieving a blood concentration of greater than or equal to ½ amount of the aforementioned Cmax, a daily dose of epalrestat can be 75 to 400 mg, 75 to 300 mg, 75 to 200 mg, or 75 to 150 mg. From the view point of achieving a blood concentration of ¼ amount or more of the aforementioned Cmax, a daily dose of epalrestat can be 37 to 400 mg, 37 to 300 mg, 37 to 200 mg, or 37 to 150 mg. The aforementioned administration is preferably by an injection or by oral administration. By achieving the aforementioned blood concentration, it is expected that epalrestat passes through BRB and effectively suppresses CNV or drusen.

Although not limited to the following, an adult daily dose in the case of using zafirlukast as an active ingredient is preferably 10 to 200 mg, more preferably 20 to 150 mg, further preferably 30 to 100 mg, particularly preferably 40 to 80 mg. Cmax in the case of zafirlukast is 0.8 µM ("Leukotriene receptor antagonist/antiasthmatic agent, ACCOLATE (registered trademark) tablet 20 mg zafirlukast tablet", Pharmaceutical Interview Form, prepared in January 2015 (the revised ninth edition), in the case of single-dose administration). The dose of zafirlukast is preferably an administration amount with which Cmax of greater than or equal to about 0.8 µM is achieved, and as long as the effect of the present invention is exerted, the dose can be such an administration amount that achieves a blood concentration of greater than or equal to ½ amount of Cmax, or greater than or equal to ¼ amount of Cmax. From the viewpoint of achieving the aforementioned Cmax, a daily dose of zafirlukast can be 40 to 200 mg, 40 to 150 mg, 40 to 100 mg, or 40 to 80 mg. From the viewpoint of achieving a blood concentration of greater than or equal to ½ amount of the aforementioned Cmax, a daily dose of zafirlukast can be 20 to 200 mg, 20 to 150 mg, 20 to 100 mg, 20 to 80 mg, or 20 to 40 mg. From the view point of achieving a blood concentration of ¼ amount or more of the aforementioned Cmax, a daily dose of zafirlukast can be 10 to 200 mg, 10 to 150 mg, 10 to 100 mg, 10 to 80 mg, 10 to 40 mg, or 10 to 20 mg. The aforementioned administration is preferably by an injection or by oral administration. By achieving the aforementioned blood concentration, it is expected that zafirlukast passes through BRB and effectively suppresses CNV or drusen.

Although not limited to the following, an adult daily dose in the case of using amlexanox as an active ingredient is preferably 10 to 150 mg, more preferably 15 to 100 mg, further preferably 20 to 80 mg, particularly preferably 25 to 50 mg. Cmax in the case of amlexanox is 16.0 µM ("Antiasthmatic, allergic coryza therapeutic agent", Japanese Pharmacopoeia, amlexanox tablet SOLFA (registered trademark) 25 mg tablet, SOLFA (registered trademark) 50 mg tablet, Pharmaceutical Interview Form, revised in October 2012

(the revised second edition), in the case of single-dose administration). The dose of amlexanox is preferably an administration amount with which Cmax of greater than or equal to about 16.0 µM is achieved, and as long as the effect of the present invention is exerted, the dose can be such an administration amount that achieves a blood concentration of greater than or equal to ½ amount of Cmax, or greater than or equal to ¼ amount of Cmax. From the view point of achieving the aforementioned Cmax, a daily dose of amlexanox can be 75 to 150 mg. From the view point of achieving a blood concentration of greater than or equal to ½ amount of the aforementioned Cmax, a daily dose of amlexanox can be 37 to 150 mg, 37 to 100 mg, or 37 to 75 mg. From the view point of achieving a blood concentration of ¼ amount or more of the aforementioned Cmax, a daily dose of amlexanox can be 18 to 150 mg, 18 to 100 mg, 18 to 75 mg, or 18 to 37 mg. The aforementioned administration is preferably by an injection or by oral administration. By achieving the aforementioned blood concentration, it is expected that amlexanox passes through BRB and effectively suppresses CNV or drusen.

Although not limited to the following, an adult daily dose in the case of using seratrodast as an active ingredient is preferably 8 to 120 mg, more preferably 25 to 110 mg, further preferably 50 to 100 mg, particularly preferably 70 to 90 mg, most preferably 80 mg. Cmax in the case of seratrodast is 31.03 µM ("Thromboxane A2 receptor antagonist, Bronica (registered trademark) tablet 40, 80", Pharmaceutical Interview Form, revised in October 2016, (the fourth edition), in the case of single-dose administration). The dose of seratrodast is preferably an administration amount with which Cmax of greater than or equal to about 31.03 µM is achieved, and as long as the effect of the present invention is exerted, the dose can be such an administration amount that achieves a blood concentration of greater than or equal to ½ amount of Cmax, or greater than or equal to ¼ amount of Cmax. From the view point of achieving the aforementioned Cmax, a daily dose of seratrodast can be 80 to 120 mg, 80 to 110 mg, 80 to 100 mg, or 80 to 90 mg. From the view point of achieving a blood concentration of greater than or equal to ½ amount of the aforementioned Cmax, a daily dose of seratrodast can be 50 to 120 mg, 50 to 110 mg, 50 to 100 mg, 50 to 90 mg, 50 to 80 mg, or 50 to 70 mg. From the view point of achieving a blood concentration of ¼ amount or more of the aforementioned Cmax, a daily dose of seratrodast can be 25 to 120 mg, 25 to 110 mg, 25 to 100 mg, 25 to 90 mg, 25 to 80 mg, 25 to 60 mg, or 25 to 40 mg. The aforementioned administration is preferably by an injection or by oral administration. By achieving the aforementioned blood concentration, it is expected that seratrodast passes through BRB and effectively suppresses CNV or drusen.

In the present description, the dosage form of preparation is not particularly limited, and can be liquid preparations (e.g., suspensions, emulsions, capsules, syrups, injections, etc.) or solid preparations (powders, fine granules, granules, pills, tablets, etc.).

The preparation provided in the present description can have, but not limited to, a pH of 4.0 to 8.5. From the view point of significantly exerting the effect of the present invention, pH of the preparation is preferably greater than or equal to 4.5, more preferably greater than or equal to 5.0, further preferably greater than or equal to 5.5, particularly preferably greater than or equal to 6.0, most preferably greater than or equal to 6.5. Also from the view point of significantly exerting the effect of the present invention, pH of the preparation is preferably less than or equal to 8.0, more preferably less than or equal to 7.8, further preferably less than or equal to 7.7, particularly preferably less than or equal to 7.6, most preferably less than or equal to 7.5. Also from the view point of significantly exerting the effect of the present invention, pH of the preparation is preferably 4.5 to 8.0, more preferably 5.0 to 7.8, further preferably 5.5 to 7.7, particularly preferably 6.0 to 7.6, most preferably 6.5 to 7.6.

[Solid Preparations]

The preparation provided in the present description can be prepared by an ordinary method while an ordinary carrier component is added depending on the preparation form as long as stability or the like is not impaired. For example, tablets can be prepared by mixing a powdery active ingredient, and a pharmaceutically acceptable carrier component (filler or the like), and compression-molding the mixture. Among solid preparations, powder and granular preparations such as granules may be prepared by a variety of granulation methods (extrusion granulation method, crushing granulation method, dry compaction granulation method, fluidized bed granulation method, tumbling granulation method, high-speed stirring granulation method, etc.), and tablets can be prepared by appropriately combining the aforementioned granulation methods, and tableting methods (wet tableting method, direct tableting method) and so on. Tablets may be coated with sugar to give sugar-coated tablets. Further, tablets maybe either monolayer tablets, or multilayer tablets such as bilayer tablets. A preferred dosage form of solid preparations is a tablet (for example, an oral chewable tablet).

In solid preparations, examples of carrier components and additives include fillers (sugar alcohols such as D-sorbitol, D-mannitol, and xylitol, saccharides such as glucose, sucrose, lactose, and fructose, crystalline cellulose, carmellose sodium, carmellose calcium, dibasic calcium phosphate, wheat starch, rice starch, corn starch, potato starch, dextrin, β-cyclodextrin, light anhydrous silicic acid, titanium oxide, magnesium aluminometasilicate, talc, kaolin, etc.); disintegrators (low substituted hydroxypropylcellulose, carboxymethylcellulose calcium, crospovidone, croscarmellose sodium, hydroxypropyl starch, partly pregelatinized starch, etc.); binders (cellulose derivatives such as methyl cellulose, ethyl cellulose, hydroxyethyl cellulose, hydroxypropyl cellulose, hydroxypropyl methylcellulose, and sodium carboxymethylcellulose, polyvinyl pyrrolidone, polyvinyl alcohol, acrylic acid-based polymer, gelatin, gum arabic, pullulan, pregelatinized starch, agar, tragacanth, sodium alginate, propylene glycol alginate, etc.); lubricants (stearic acid, magnesium stearate, calcium stearate, polyoxyl stearate, cetanol, talc, hardened oil, sucrose fatty acid ester, dimethyl polysiloxane, yellow beeswax, white beeswax, etc.); antioxidants (dibutylhydroxytoluene (BHT), propyl gallate, butylated hydroxyanisole (BHA), tocopherol, citric acid, etc.); coating agents (hydroxypropyl methylcellulose, hydroxypropyl cellulose, methyl cellulose, ethyl cellulose, hydroxypropylmethylcellulose phthalate, hydroxypropylmethylcellulose acetate succinate, carboxymethylethyl cellulose, cellulose acetate phthalate, polyvinyl acetal diethylaminoacetate, aminoalkyl methacrylate copolymer, hydroxypropylmethylcellulose acetate succinate, methacrylate copolymer, polyvinylacetate diethylaminoacetate, shellac, etc.); coloring agents (turmeric extract, riboflavin, titanium oxide, carotene liquid, etc.); corrigents (aspartame, ascorbic acid, stevia, menthol, glycyrrhiza crude extract, simple syrup, etc.); foaming agents (sodium bicarbonate etc.); fluidizing agents (sodium aluminometasilicate, light anhydrous silicic acid, etc.); surfactants (polyoxyethylene hardened castor oil, glyceryl monostearate, sorbitan monostearate, sorbitan monolaurate, polyoxyethylene polyoxypropylene, polysorbates, sodium lauryl sulfate, macrogols such as macrogol 6000, sucrose fatty acid ester, etc.); plasticizers (triethyl citrate, polyethylene glycol, triacetin, cetanol, etc.); sweetening agents (natural or synthetic sweetening agents such as sucrose, mannitol, aspartame, etc.); aromatizing agents (menthol, etc.); absorbents, preservatives, moistening agents, and antistatic agents.

When the preparation is a solid preparation, the content of at least one selected from the group consisting of zaltoprofen, oxaprozin, tiaprofenic acid, flufenamic acid, mefenamic acid, sulindac, epalrestat, zafirlukast, amlexanox, seratrodast, and pharmaceutically acceptable salts thereof, or an EMT suppressive compound can be, but not limited to, 0.1 to 30 wt %, preferably 0.5 to 25 wt %, more preferably 0.5 to 20 wt % relative to the whole quantity of the preparation. The content of the present compound may be 0.01 to 3 wt %, 0.02 to 2 wt %, or 0.03 to 1 wt %.

[Ophthalmic Preparations]

In the case of ophthalmic preparations, the properties are not particularly limited, and can be any properties such as liquid, fluid, gel, semisolid, or solid, for example. The types of ophthalmic preparations are not particularly limited. For example, ophthalmic solutions, ophthalmic ointments (water soluble ophthalmic ointments, oil soluble ophthalmic ointments), and intraocular injections (for example, intravitreous injections) can be recited.

Ophthalmic preparations in the forms other than solid, such as of liquid, fluid, gel, or semi-solid, or in the solid form or the like may be aqueous compositions, or oleaginous compositions as represented by ointments.

Methods for preparing ophthalmic preparations are well known. An ophthalmic preparation can be prepared by mixing at least one selected from the group consisting of zaltoprofen, oxaprozin, tiaprofenic acid, flufenamic acid, mefenamic acid, sulindac, epalrestat, zafirlukast, amlexanox, seratrodast, and pharmaceutically acceptable salts thereof, or an EMT suppressive compound with a pharmaceutically acceptable base or carrier, and with a pharmaceutically acceptable additive for ophthalmic preparations, and other active ingredient (physiologically active component or pharmacologically active component other than the present compound) as needed.

Examples of the base or carrier include water, aqueous solvents such as polar solvents; polyhydric alcohols; vegetable oils; and oleaginous bases. Examples of the base or carrier for intraocular injections include distilled water for injections or saline. The base or carrier can be used singly or in combination of two or more kinds.

Examples of the additive for ophthalmic preparations include a surfactant, a perfume or a refrigerant, an antiseptic, a bactericide, or an antibacterial, a pH regulator, an isotonizing agent, a chelating agent, a buffer, a stabilizer, an antioxidant, and a thickening agent. An intraocular injection may contain a solubilizing agent, a suspending agent, an isotonizing agent, a buffer, a soothing agent, a stabilizer, an antiseptic and the like. The additive can be used singly or in combination of two or more kinds.

When the ophthalmic preparation is in the form other than solid, such as of liquid, fluid, gel, or semi-solid, the content of at least one selected from the group consisting of zaltoprofen, oxaprozin, tiaprofenic acid, flufenamic acid, mefenamic acid, sulindac, epalrestat, zafirlukast, amlexanox, seratrodast, and pharmaceutically acceptable salts thereof, or an EMT suppressive compound in the ophthalmic composition can be greater than or equal to 0.00001 wt %, preferably greater than or equal to 0.0001 wt %, more preferably greater than or equal to 0.001 wt % relative to the whole quantity of the composition. Also, the content of at least one selected from the group consisting of zaltoprofen, oxaprozin, tiaprofenic acid, flufenamic acid, mefenamic acid, sulindac, epalrestat, zafirlukast, amlexanox, seratrodast, and pharmaceutically acceptable salts thereof, or an EMT suppressive compound in the ophthalmic composition may be greater than or equal to 0.01 wt %, greater than or equal to 0.1 wt %, or greater than or equal to 1 wt % relative to the whole quantity of the composition. The above range provides sufficient prophylactic, ameliorative or therapeutic effect for retinal diseases.

Meanwhile, when the ophthalmic preparation is in the form other than solid, such as of liquid, fluid, gel, or semi-solid, the content of at least one selected from the group consisting of zaltoprofen, oxaprozin, tiaprofenic acid, flufenamic acid, mefenamic acid, sulindac, epalrestat, zafirlukast, amlexanox, seratrodast, and pharmaceutically acceptable salts thereof, or an EMT suppressive compound in the ophthalmic composition can be less than or equal to 10 wt %, preferably less than or equal to 5 wt %, more preferably less than or equal to 3 wt % relative to the whole quantity of the composition. The above range provides sufficient prophylactic, ameliorative or therapeutic effect of retinal diseases, and provides a preparation with less foreign body feeling at the time of instillation.

When the ophthalmic preparation is in the form other than solid, such as of liquid, fluid, gel, or semi-solid, the content of the present composition in the ophthalmic composition can be 0.00001 to 10 wt %, 0.00001 to 5 wt %, 0.00001 to 3 wt %, 0.0001 to 10 wt %, 0.0001 to 5 wt %, 0.0001 to 3 wt %, 0.001 to 10 wt %, 0.001 to 5 wt %, 0.001 to 3 wt %, 0.01 to 10 wt %, 0.01 to 5 wt %, 0.01 to 3 wt %, 0.1 to 10 wt %, 0.1 to 5 wt %, 0.1 to 3 wt %, 1 to 10 wt %, 1 to 5 wt %, 1 to 3 wt %, relative to the whole quantity of the composition.

When the ophthalmic preparation is a composition containing moisture, pH of the ophthalmic preparation is, but not limited to, preferably greater than or equal to 4, more preferably greater than or equal to 5.5, further preferably greater than or equal to 6, and still further preferably greater than or equal to 6.5. The above range provides a preparation in which the present compound has excellent stability against heat and light. The ophthalmic preparation has pH of preferably less than or equal to 9, more preferably less than or equal to 8.5, further preferably less than or equal to 8, still further preferably less than or equal to 7.5. Stimulation to an eye is suppressed by the above range.

[Injections]

An injection can be prepared, for example, according to a known method described in Japanese Pharmacopoeia, by dissolving or dispersing at least one selected from the group consisting of zaltoprofen, oxaprozin, tiaprofenic acid, flufenamic acid, mefenamic acid, sulindac, epalrestat, zafirlukast, amlexanox, seratrodast, and pharmaceutically acceptable salts thereof, or an EMT suppressive compound in distilled water for injection or a saline as an active ingredient. Also, an injection may further contain a pharmaceutically acceptable carrier such as a solubilizing agent, a suspending agent, an isotonizing agent, a buffer, a soothing agent, a stabilizer, or an antiseptic, or further a pharmaceutically acceptable additive for injections.

An injection can contain a pharmacologically active component or a physiologically active component other than prophylactic, ameliorative, or therapeutic component for retinal diseases. Examples of such a pharmacologically active component or a physiologically active component include a neurotrophic factor, a decongestive component, an ocular muscle regulator component, an anti-inflammatory component or an astringent component, an antihistamine component or an antiallergic component, vitamins, amino acids, an antibacterial component or a bactericide component.

The content of at least one selected from the group consisting of zaltoprofen, oxaprozin, tiaprofenic acid, flufenamic acid, mefenamic acid, sulindac, epalrestat, zafirlukast, amlexanox, seratrodast, and pharmaceutically acceptable salts thereof, or an EMT suppressive compound in the injection is preferably greater than or equal to 0.001 wt %, more preferably greater than or equal to 0.01 wt %, further preferably greater than or equal to 0.1 wt % relative to the whole quantity of the preparation. Also, less than or equal to 80 wt % is preferred, less than or equal to 60 wt % is more preferred, and less than or equal to 50 wt % is further preferred. The above range provides sufficient prophylactic, ameliorative or therapeutic effect for retinal diseases.

The content of at least one selected from the group consisting of zaltoprofen, oxaprozin, tiaprofenic acid, flufenamic acid, mefenamic acid, sulindac, epalrestat, zafirlukast, amlexanox, seratrodast, and pharmaceutically acceptable salts thereof, or an EMT suppressive compound in the injection can be 0.001 to 80 wt %, 0.001 to 60 wt %, 0.001 to 50 wt %, 0.01 to 80 wt %, 0.01 to 60 wt %, 0.01 to 50 wt %, 0.1 to 80 wt %, 0.1 to 60 wt %, or 0.1 to 50 wt. % relative to the whole quantity of the preparation.

In an injection, a pharmacologically active component or a physiologically active component other than an additive, and at least one selected from the group consisting of zaltoprofen, oxaprozin, tiaprofenic acid, flufenamic acid, mefenamic acid, sulindac, epalrestat, zafirlukast, amlexanox, seratrodast, and pharmaceutically acceptable salts thereof, or an EMT suppressive compound can be used singly or in combination of two or more kinds.

[Capsules]

Capsules can be prepared by filling capsules (soft or hard capsules) with powder and granular formulations (powders, granules, etc.). When the preparation is a capsule, the content of at least one selected from the group consisting of zaltoprofen, oxaprozin, tiaprofenic acid, flufenamic acid, mefenamic acid, sulindac, epalrestat, zafirlukast, amlexanox, seratrodast, and pharmaceutically acceptable salts thereof, or an EMT suppressive compound in the preparation can be, but not limited to, 0.01 to 3 wt %, preferably 0.02 to 2 wt %, more preferably 0.03 to 1 wt. % relative to the whole quantity of the preparation. It is preferred to fill a soft capsule or the like with such a liquid preparation for use as soft capsules.

When the preparation is a hard capsule, the content of at least one selected from the group consisting of zaltoprofen, oxaprozin, tiaprofenic acid, flufenamic acid, mefenamic acid, sulindac, epalrestat, zafirlukast, amlexanox, seratrodast, and pharmaceutically acceptable salts thereof, or an EMT suppressive compound in the contents for hard capsules excluding a capsule shell can be, but not limited to, 0.1 to 30 wt %, preferably 0.5 to 25 wt %, more preferably 0.5 to 20 wt % relative to the whole quantity of the preparation. The content of the present compound may be 0.01 to 3 wt %, 0.02 to 2 wt %, or 0.03 to 1 wt %.

Examples of additives in the case of liquid formulations include oleaginous bases (e.g., vegetable oil such as olive oil, corn oil, soybean oil, sesame oil, or cottonseed oil; medium-chain fatty acid triglyceride, etc.), aqueous bases (e.g., macrogol 400, water), gel bases (e.g., carboxy vinyl polymer, gum substances, etc.), surfactants (e.g., polysorbate 80, hardened castor oil, glycerin fatty acid ester, sorbitan sesquioleate, etc.), suspending agents (e.g., kaolin, carmellose sodium, tragacanth, white beeswax, various surfactants, gum arabic, powdered gum arabic, xanthan gum, soybean lecithin, etc.), dispersants, emulsifiers, stabilizers, buffers, solubilizing agents, antifoaming agents (dimethylpolysiloxane, silicon antifoamer, etc.), pH regulators (citric acid, malic acid, dibasic sodium phosphate, dipotassium phosphate, etc.), antiseptics (preservatives), and refrigerants (1-menthol, mentha water, etc.).

In any case, an antioxidant, a sweetening agent, an acidulant, a coloring agent, a perfume, a tasting agent and the like may be appropriately added to these liquid formulations.

Liquid formulations can be prepared, for example, by dissolving or dispersing ingredients in an aqueous solvent (such as purified water, ethanol-containing purified water) which is a carrier ingredient, and conducting a filtration or sterilization treatment as needed, and filling a predetermined container with the resultant solution or dispersion, and subjecting the container to a sterilization treatment.

The aforementioned composition can be made into, for example, but not particularly limited as long as the effect of the present invention is exerted, pharmaceuticals, quasi-drugs, or functional food products.

[Functional Foods]

The present invention can also be provided as functional foods. In the present description, "functional foods" refer to foods and beverages having pharmaceutical efficacy approved and designated by the government or public entity, or foods and beverages indicating their functionalities based on the contents of prescribed effects reported to the government or the like by the manufacturer. Functional foods include specially designated health foods, functional nutritional foods, foods with functional claims, foods for the aged, and dietary supplements (balanced nutritional foods, supplements). Also included are foods and beverages that contain packages, containers, package inserts, instructions and so on indicating pharmaceutical efficacy or functionality. Also included are foods and beverages indicating pharmaceutical efficacy or functionality in an application form to the government or the like. Such indications include indication regarding prophylaxis and/or therapy for choroidal neovascularization, indication regarding prophylaxis and/or therapy for AMD such as AMD, early or intermediate AMD, Dry AMD, WetAMD and so on, and indication regarding prophylaxis, amelioration, and/or therapy of symptoms characteristic for AMD such as distortion of visual field (metamorphopsia), color tone of visual field, hyperphotosensitivity, rapid decline in visual acuity, and central scotoma.

Embodiments

Regarding the aforementioned aspects, the present invention discloses, but not limited to, the following embodiments.

A prophylactic and/or therapeutic agent for choroidal neovascularization containing at least one selected from the group consisting of zaltoprofen, oxaprozin, tiaprofenic acid, flufenamic acid, mefenamic acid, sulindac, epalrestat, zafirlukast, amlexanox, seratrodast, and pharmaceutically acceptable salts thereof, as an active ingredient.

The prophylactic and/or therapeutic agent for choroidal neovascularization, which is an oral agent or an injection.

The prophylactic and/or therapeutic agent for choroidal neovascularization, wherein the oral agent is a solid preparation.

The prophylactic and/or therapeutic agent for choroidal neovascularization, wherein the solid preparation is a tablet.

The prophylactic and/or therapeutic agent for choroidal neovascularization, which is a liquid formulation.

The prophylactic and/or therapeutic agent for choroidal neovascularization, wherein the liquid formulation is an ophthalmic preparation or a capsule.

The prophylactic and/or therapeutic agent for choroidal neovascularization, wherein the choroidal neovascularization occurs in age-related macular degeneration, polypoidal choroidal vasculopathy (PCV), or retinal angiomatous proliferation (RAP).

The prophylactic and/or therapeutic agent for choroidal neovascularization, wherein the choroidal neovascularization occurs by EMT in RPE cells.

The prophylactic and/or therapeutic agent for choroidal neovascularization, wherein at least one selected from the group consisting of zaltoprofen, oxaprozin, tiaprofenic acid, flufenamic acid, mefenamic acid, sulindac, epalrestat, zafirlukast, amlexanox, seratrodast, and pharmaceutically acceptable salts thereof is administered in an amount sufficient to suppress EMT in RPE cells.

The prophylactic and/or therapeutic agent for choroidal neovascularization, wherein at least one selected from the group consisting of zaltoprofen, oxaprozin, tiaprofenic acid, flufenamic acid, mefenamic acid, sulindac, epalrestat, zafirlukast, amlexanox, seratrodast, and pharmaceutically acceptable salts thereof is administered in an amount sufficient to suppress expression of a mesenchymal marker or an extracellular matrix in RPE cells.

The prophylactic and/or therapeutic agent for choroidal neovascularization, wherein the mesenchymal marker is at least one selected from the group consisting of Snail, Slug, CDH3, MMP1, MMP7, MMP3, ZEB2, CDH2, and VIM.

The prophylactic and/or therapeutic agent for choroidal neovascularization, wherein the extracellular matrix is at least one selected from the group consisting of COL5A3, COL6A3, LAMC2, HMMR, TNC, COL1A1, COL1A2, SRGN, FN1, COL5A2, COL13A1, and LAMB3.

The prophylactic and/or therapeutic agent for choroidal neovascularization, wherein zaltoprofen or a salt thereof is administered in an administration amount that achieves a Cmax of greater than or equal to 20.4 µM.

The prophylactic and/or therapeutic agent for choroidal neovascularization, wherein zaltoprofen or a salt thereof is administered in an administration amount that achieves a Cmax of greater than or equal to 16.8 µM.

The prophylactic and/or therapeutic agent for choroidal neovascularization, wherein zaltoprofen or a salt thereof is administered in an administration amount that achieves a blood concentration of greater than or equal to ½ amount of the Cmax.

The prophylactic and/or therapeutic agent for choroidal neovascularization, wherein zaltoprofen or a salt thereof is administered in an administration amount that achieves a blood concentration of greater than or equal to ¼ amount of the Cmax.

The prophylactic and/or therapeutic agent for choroidal neovascularization, wherein oxaprozin or a salt thereof is administered in an administration amount that achieves a Cmax of greater than or equal to 340.9 µM.

The prophylactic and/or therapeutic agent for choroidal neovascularization, wherein oxaprozin or a salt thereof is administered in an administration amount that achieves a blood concentration of greater than or equal to ½ amount of the Cmax.

The prophylactic and/or therapeutic agent for choroidal neovascularization, wherein oxaprozin or a salt thereof is administered in an administration amount that achieves a blood concentration of greater than or equal to ¼ amount of the Cmax.

The prophylactic and/or therapeutic agent for choroidal neovascularization, wherein tiaprofenic acid or a salt thereof is administered in an administration amount that achieves a Cmax of greater than or equal to 69.15 µM.

The prophylactic and/or therapeutic agent for choroidal neovascularization, wherein tiaprofenic acid or a salt thereof is administered in an administration amount that achieves a blood concentration of greater than or equal to ½ amount of the Cmax.

The prophylactic and/or therapeutic agent for choroidal neovascularization, wherein tiaprofenic acid or a salt thereof is administered in an administration amount that achieves a blood concentration of greater than or equal to ¼ amount of the Cmax.

The prophylactic and/or therapeutic agent for choroidal neovascularization, wherein flufenamic acid or a salt thereof is administered in an administration amount that achieves a Cmax of greater than or equal to 27.91 µM.

The prophylactic and/or therapeutic agent for choroidal neovascularization, wherein flufenamic acid or a salt thereof is administered in an administration amount that achieves a blood concentration of greater than or equal to ½ amount of the Cmax.

The prophylactic and/or therapeutic agent for choroidal neovascularization, wherein flufenamic acid or a salt thereof is administered in an administration amount that achieves a blood concentration of greater than or equal to ¼ amount of the Cmax.

The prophylactic and/or therapeutic agent for choroidal neovascularization, wherein mefenamic acid or a salt thereof is administered in an administration amount that achieves a Cmax of greater than or equal to 38.54 µM.

The prophylactic and/or therapeutic agent for choroidal neovascularization, wherein mefenamic acid or a salt thereof is administered in an administration amount that achieves a blood concentration of greater than or equal to ½ amount of the Cmax.

The prophylactic and/or therapeutic agent for choroidal neovascularization, wherein mefenamic acid or a salt thereof is administered in an administration amount that achieves a blood concentration of greater than or equal to ¼ amount of the Cmax.

The prophylactic and/or therapeutic agent for choroidal neovascularization, wherein sulindac or a salt thereof is administered in an administration amount that achieves a Cmax of greater than or equal to 10.10 µM.

The prophylactic and/or therapeutic agent for choroidal neovascularization, wherein sulindac or a salt thereof is administered in an administration amount that achieves a blood concentration of greater than or equal to ½ amount of the Cmax.

The prophylactic and/or therapeutic agent for choroidal neovascularization, wherein sulindac or a salt thereof is administered in an administration amount that achieves a blood concentration of greater than or equal to ¼ amount of the Cmax.

The prophylactic and/or therapeutic agent for choroidal neovascularization, wherein epalrestat or a salt thereof is administered in an administration amount that achieves a Cmax of greater than or equal to 12.2 μM.

The prophylactic and/or therapeutic agent for choroidal neovascularization, wherein epalrestat or a salt thereof is administered in an administration amount that achieves a blood concentration of greater than or equal to ½ amount of the Cmax.

The prophylactic and/or therapeutic agent for choroidal neovascularization, wherein epalrestat or a salt thereof is administered in an administration amount that achieves a blood concentration of greater than or equal to ¼ amount of the Cmax.

The prophylactic and/or therapeutic agent for choroidal neovascularization, wherein zafirlukast or a salt thereof is administered in an administration amount that achieves a Cmax of greater than or equal to 0.8 μM.

The prophylactic and/or therapeutic agent for choroidal neovascularization, wherein zafirlukast or a salt thereof is administered in an administration amount that achieves a blood concentration of greater than or equal to ½ amount of the Cmax.

The prophylactic and/or therapeutic agent for choroidal neovascularization, wherein zafirlukast or a salt thereof is administered in an administration amount that achieves a blood concentration of greater than or equal to ¼ amount of the Cmax.

The prophylactic and/or therapeutic agent for choroidal neovascularization, wherein amlexanox or a salt thereof is administered in an administration amount that achieves a Cmax of greater than or equal to 16.0 μM.

The prophylactic and/or therapeutic agent for choroidal neovascularization, wherein amlexanox or a salt thereof is administered in an administration amount that achieves a blood concentration of greater than or equal to ½ amount of the Cmax.

The prophylactic and/or therapeutic agent for choroidal neovascularization, wherein amlexanox or a salt thereof is administered in an administration amount that achieves a blood concentration of greater than or equal to ¼ amount of the Cmax.

The prophylactic and/or therapeutic agent for choroidal neovascularization, wherein seratrodast or a salt thereof is administered in an administration amount that achieves a Cmax of greater than or equal to 31.03 μM.

The prophylactic and/or therapeutic agent for choroidal neovascularization, wherein seratrodast or a salt thereof is administered in an administration amount that achieves a blood concentration of greater than or equal to ½ amount of the Cmax.

The prophylactic and/or therapeutic agent for choroidal neovascularization, wherein seratrodast or a salt thereof is administered in an administration amount that achieves a blood concentration of greater than or equal to ¼ amount of the Cmax.

The prophylactic and/or therapeutic agent for choroidal neovascularization, containing 25 to 360 mg of zaltoprofen or a salt thereof as a daily dose.

The prophylactic and/or therapeutic agent for choroidal neovascularization, containing 100 to 700 mg of oxaprozin or a salt thereof as a daily dose.

The prophylactic and/or therapeutic agent for choroidal neovascularization, containing 60 to 900 mg of tiaprofenic acid or a salt thereof as a daily dose.

The prophylactic and/or therapeutic agent for choroidal neovascularization, containing 75 to 1250 mg of flufenamic acid or a salt thereof as a daily dose.

The prophylactic and/or therapeutic agent for choroidal neovascularization, containing 150 to 2250 mg of mefenamic acid or a salt thereof as a daily dose.

The prophylactic and/or therapeutic agent for choroidal neovascularization, containing 30 to 500 mg of sulindac or a salt thereof as a daily dose.

The prophylactic and/or therapeutic agent for choroidal neovascularization, containing 10 to 400 mg of epalrestat or a salt thereof as a daily dose.

The prophylactic and/or therapeutic agent for choroidal neovascularization, containing 10 to 200 mg of zafirlukast or a salt thereof as a daily dose.

The prophylactic and/or therapeutic agent for choroidal neovascularization, containing 10 to 150 mg of amlexanox or a salt thereof as a daily dose.

The prophylactic and/or therapeutic agent for choroidal neovascularization, containing 8 to 120 mg of seratrodast or a salt thereof as a daily dose.

The prophylactic and/or therapeutic agent for choroidal neovascularization, administered once to three times a day.

The prophylactic and/or therapeutic agent for choroidal neovascularization, administered once or twice a day.

The prophylactic and/or therapeutic agent for choroidal neovascularization, administered once a day.

A VEGF production suppressor containing at least one selected from the group consisting of zaltoprofen, oxaprozin, tiaprofenic acid, flufenamic acid, mefenamic acid, sulindac, epalrestat, zafirlukast, amlexanox, seratrodast, and pharmaceutically acceptable salts thereof, as an active ingredient.

A VEGF expression suppressor containing at least one selected from the group consisting of zaltoprofen, oxaprozin, tiaprofenic acid, flufenamic acid, mefenamic acid, sulindac, epalrestat, zafirlukast, amlexanox, seratrodast, and pharmaceutically acceptable salts thereof, as an active ingredient.

A drusen suppressor containing a compound having an activity of suppressing epithelial-mesenchymal transition in retinal pigment epithelial cells, as an active ingredient.

The drusen suppressor, wherein the compound having an activity of suppressing epithelial-mesenchymal transition is a drug that suppresses expression of a mesenchymal marker or an extracellular matrix in the retinal pigment epithelial cells.

The drusen suppressor, wherein the compound having an activity of suppressing epithelial-mesenchymal transition is a drug that suppresses enhancement of mobility of the retinal pigment epithelial cells.

The drusen suppressor, wherein the mesenchymal marker is at least one selected from the group consisting of Snail, Slug, CDH3, MMP1, MMP7, MMP3, ZEB2, CDH2, and VIM.

The drusen suppressor, wherein the extracellular matrix is at least one selected from the group consisting of COL5A3, COL6A3, LAMC2, HMMR, TNC, COL1A1, COL1A2, SRGN, FN1, COL5A2, COL13A1, and LAMB3.

The drusen suppressor, wherein the mesenchymal marker is at least one selected from the group consisting of Snail, Slug, cadherin3, MMP1, and MMP7, and/or, the extracellular matrix is at least one selected from the group consisting of COL5A3, COL6A3, LAMC2, HMMR, and TNC.

The drusen suppressor, wherein the compound having an activity of suppressing epithelial-mesenchymal transition is a nonsteroidal anti-inflammatory drug, an aldose reductase inhibitor, a leukotriene receptor antagonist, a chemical mediator release suppressor, and/or a thromboxane A2 receptor antagonist.

The drusen suppressor, wherein the nonsteroidal anti-inflammatory drug is a propionic acid-based nonsteroidal anti-inflammatory drug, an aminoaryl carboxylic acid-based nonsteroidal anti-inflammatory drug, or an aryl acetic acid-based nonsteroidal anti-inflammatory drug, and the leukotriene receptor antagonist is an antagonist of cysteinyl leukotriene type 1 (CysLT1) receptor or a 5-lipoxygenase inhibitor.

The drusen suppressor, wherein the propionic acid-based nonsteroidal anti-inflammatory drug is at least one selected from the group consisting of zaltoprofen, oxaprozin, tiaprofenic acid, ibuprofen, flurbiprofen, and pharmaceutically acceptable salts thereof,
the aminoaryl carboxylic acid-based nonsteroidal anti-inflammatory drug is at least one selected from the group consisting of flufenamic acid, mefenamic acid, and pharmaceutically acceptable salts thereof,
the aryl acetic acid-based nonsteroidal anti-inflammatory drug is sulindac and/or a pharmaceutically acceptable salt thereof,
the aldose reductase inhibitor is epalrestat and/or a pharmaceutically acceptable salt thereof,
the leukotriene receptor antagonist is at least one selected from the group consisting of zafirlukast, montelukast, pranlukast, and pharmaceutically acceptable salts thereof,
the chemical mediator release suppressor is amlexanox and/or a pharmaceutically acceptable salt thereof, and/or,
the thromboxane A2 receptor antagonist is seratrodast and/or a pharmaceutically acceptable salt thereof.

The drusen suppressor, wherein the compound having an activity of suppressing epithelial-mesenchymal transition is at least one selected from the group consisting of Alisertib, MK-0457 (Tozasertib), PHA-739358 (danusertib), AMG-900, Barasertib, CYC116, MLN8054, Baicalin, Baicalein, Lupeol, Istanbulin A, Phytol, Diphenyl difluoroketone (EF24), Crucmin, Phloroglucinol, Plumbagin, Rapamycin, FK506 (Tacrolimus), Thalidomide, LY550410, SB-505124, SD-208, TAPI-0, TAPI-1, JNJ-38877605, PF-04217903, AG1478 (Tyrphostin), Erlotinib, Gefitinib, Lapatinib, PD153035, PD158780, WHI-P154, BMS-536924, A83-01, D4476, LY-364947, SB-431542, SD-208, AZD6244 (Selumetinib), CI-1040, PD0325901, GDC-0941 (Pictilisib), PI-103, PIK-90, ZSTK474, API-2, AZD0530 (Saracatinib), PP1, 2-Hydroxycinnamaldehyde, 5-aza-dC, BI 5700, Celecoxib, CX-4945 (Silmitasertib), Disulfiram, Eribulin mesyate, Evodiamine, EW-7203, Fasudil, Nintedanib, Fuzheng Huayu recipe, Grape seed proanthocyanidins, Vorinostat, Herbimycin A, Entinostat, Honokiol, NPI-0052, Methacycline, Dasatinib, Ki26894, NSC 74859, NVP-LDE-225 (Erismodegib), Palbociclib, Pinocembrin, Salvianolic Acid B, Sorafenib, Resveratrol, S-Allylcysteine, Silibinin meglumine, Simvastatin, Centchroman, ML327, GN-25, Trichostatin A, Sarasinoside A1, Panobinostat, Danusertib, Cystatin C, Thymoquinone, Ulinastatin, Dendrofalconerol A (DF-A), ginsenoside (carrot saponin), staff tree seed extract, salicin (white willow extract), salicylic acid, hedge parsley extract, osthol, Muscadine grape skin extract, Tongxinluo, procyanidin C1 (cinnamon), ashwagandha root extract (Withania somnifera root extract), Qingyihuaji, roselle extract, gallic acid epigallocatechin, proanthocyanidin (grape seed extract), and Salvianolic acid B.

The drusen suppressor, which is an oral agent or an injection.

The drusen suppressor, wherein the oral agent is a solid preparation.

The drusen suppressor, wherein the solid preparation is a tablet.

The drusen formulation, which is a liquid formulation.

The drusen suppressor, wherein the liquid formulation is an ophthalmic preparation or a capsule.

The drusen suppressor, wherein zaltoprofen or a salt thereof is administered in an administration amount that achieves a Cmax of greater than or equal to 20.4 µM.

The drusen suppressor, wherein zaltoprofen or a salt thereof is administered in an administration amount that achieves a Cmax of greater than or equal to 16.8 µM.

The drusen suppressor, wherein zaltoprofen or a salt thereof is administered in an administration amount that achieves a blood concentration of greater than or equal to ½ amount of the Cmax.

The drusen suppressor, wherein zaltoprofen or a salt thereof is administered in an administration amount that achieves a blood concentration of greater than or equal to ¼ amount of the Cmax.

The drusen suppressor, wherein oxaprozin or a salt thereof is administered in an administration amount that achieves a Cmax of greater than or equal to 340.9 µM.

The drusen suppressor, wherein oxaprozin or a salt thereof is administered in an administration amount that achieves a blood concentration of greater than or equal to ½ amount of the Cmax.

The drusen suppressor, wherein oxaprozin or a salt thereof is administered in an administration amount that achieves a blood concentration of greater than or equal to ¼ amount of the Cmax.

The drusen suppressor, wherein tiaprofenic acid or a salt thereof is administered in an administration amount that achieves a Cmax of greater than or equal to 69.15 µM.

The drusen suppressor, wherein tiaprofenic acid or a salt thereof is administered in an administration amount that achieves a blood concentration of greater than or equal to ½ amount of the Cmax.

The drusen suppressor, wherein tiaprofenic acid or a salt thereof is administered in an administration amount that achieves a blood concentration of greater than or equal to ¼ amount of the Cmax.

The drusen suppressor, wherein flufenamic acid or a salt thereof is administered in an administration amount that achieves a Cmax of greater than or equal to 27.91 µM.

The drusen suppressor, wherein flufenamic acid or a salt thereof is administered in an administration amount that achieves a blood concentration of greater than or equal to ½ amount of the Cmax.

The drusen suppressor, wherein flufenamic acid or a salt thereof is administered in an administration amount that achieves a blood concentration of greater than or equal to ¼ amount of the Cmax.

The drusen suppressor, wherein mefenamic acid or a salt thereof is administered in an administration amount that achieves a Cmax of greater than or equal to 38.54 µM.

The drusen suppressor, wherein mefenamic acid or a salt thereof is administered in an administration amount that achieves a blood concentration of greater than or equal to ½ amount of the Cmax.

The drusen suppressor, wherein mefenamic acid or a salt thereof is administered in an administration amount that achieves a blood concentration of greater than or equal to ¼ amount of the Cmax.

The drusen suppressor, wherein sulindac or a salt thereof is administered in an administration amount that achieves a Cmax of greater than or equal to 10.10 µM.

The drusen suppressor, wherein sulindac or a salt thereof is administered in an administration amount that achieves a blood concentration of greater than or equal to ½ amount of the Cmax.

The drusen suppressor, wherein sulindac or a salt thereof is administered in an administration amount that achieves a blood concentration of greater than or equal to ¼ amount of the Cmax.

The drusen suppressor, wherein epalrestat or a salt thereof is administered in an administration amount that achieves a Cmax of greater than or equal to 12.2 μM.

The drusen suppressor, wherein epalrestat or a salt thereof is administered in an administration amount that achieves a blood concentration of greater than or equal to ½ amount of the Cmax.

The drusen suppressor, wherein epalrestat or a salt thereof is administered in an administration amount that achieves a blood concentration of greater than or equal to ¼ amount of the Cmax.

The drusen suppressor, wherein zafirlukast or a salt thereof is administered in an administration amount that achieves a Cmax of greater than or equal to 0.8 μM.

The drusen suppressor, wherein zafirlukast or a salt thereof is administered in an administration amount that achieves a blood concentration of greater than or equal to ½ amount of the Cmax.

The drusen suppressor, wherein zafirlukast or a salt thereof is administered in an administration amount that achieves a blood concentration of greater than or equal to ¼ amount of the Cmax.

The drusen suppressor, wherein amlexanox or a salt thereof is administered in an administration amount that achieves a Cmax of greater than or equal to 16.0 μM.

The drusen suppressor, wherein amlexanox or a salt thereof is administered in an administration amount that achieves a blood concentration of greater than or equal to ½ amount of the Cmax.

The drusen suppressor, wherein amlexanox or a salt thereof is administered in an administration amount that achieves a blood concentration of greater than or equal to ¼ amount of the Cmax.

The drusen suppressor, wherein seratrodast or a salt thereof is administered in an administration amount that achieves a Cmax of greater than or equal to 31.03 μM.

The drusen suppressor, wherein seratrodast or a salt thereof is administered in an administration amount that achieves a blood concentration of greater than or equal to ½ amount of the Cmax.

The drusen suppressor, wherein seratrodast or a salt thereof is administered in an administration amount that achieves a blood concentration of greater than or equal to ¼ amount of the Cmax.

The drusen suppressor, containing 25 to 360 mg of zaltoprofen or a salt thereof as a daily dose.

The drusen suppressor, containing 100 to 700 mg of oxaprozin or a salt thereof as a daily dose.

The drusen suppressor, containing 60 to 900 mg of tiaprofenic acid or a salt thereof as a daily dose.

The drusen suppressor, containing 75 to 1250 mg of flufenamic acid or a salt thereof as a daily dose.

The drusen suppressor, containing 150 to 2250 mg of mefenamic acid or a salt thereof as a daily dose.

The drusen suppressor, containing 30 to 500 mg of sulindac or a salt thereof as a daily dose.

The drusen suppressor, containing 10 to 400 mg of epalrestat or a salt thereof as a daily dose.

The drusen suppressor, containing 10 to 200 mg of zafirlukast or a salt thereof as a daily dose.

The drusen suppressor, containing 10 to 150 mg of amlexanox or a salt thereof as a daily dose.

The drusen suppressor, containing 8 to 120 mg of seratrodast or a salt thereof as a daily dose.

The drusen suppressor, administered once to three times a day.

The drusen suppressor, administered once or twice a day.

The drusen suppressor, administered once a day.

A prophylactic and/or therapeutic agent for age-related macular degeneration, containing the drusen suppressor as an active ingredient.

A prophylactic and/or therapeutic agent for age-related macular degeneration, containing a propionic acid-based nonsteroidal anti-inflammatory drug, an aminoaryl carboxylic acid-based nonsteroidal anti-inflammatory drug, an aryl acetic acid-based nonsteroidal anti-inflammatory drug, an aldose reductase inhibitor, a leukotriene receptor antagonist, a chemical mediator release suppressor, or a thromboxane A2 receptor antagonist as an active ingredient, wherein the aldose reductase inhibitor is epalrestat and/or a pharmaceutically acceptable salt thereof.

The prophylactic and/or therapeutic agent for age-related macular degeneration, wherein the propionic acid-based nonsteroidal anti-inflammatory drug is at least one selected from the group consisting of zaltoprofen, oxaprozin, ibuprofen, flurbiprofen, and pharmaceutically acceptable salts thereof, the aminoaryl carboxylic acid-based nonsteroidal anti-inflammatory drug is at least one selected from the group consisting of flufenamic acid, mefenamic acid, and pharmaceutically acceptable salts thereof, the aryl acetic acid-based nonsteroidal anti-inflammatory drug is sulindac and/or a pharmaceutically acceptable salt thereof, the leukotriene receptor antagonist is at least one selected from the group consisting of zafirlukast, montelukast, pranlukast, and pharmaceutically acceptable salts thereof, the chemical mediator release suppressor is amlexanox and/or a pharmaceutically acceptable salt thereof, and the thromboxane A2 receptor antagonist is seratrodast and/or a pharmaceutically acceptable salt thereof.

The prophylactic and/or therapeutic agent for age-related macular degeneration, which is an oral agent or an injection.

The prophylactic and/or therapeutic agent for age-related macular degeneration, wherein the oral agent is a solid preparation.

The prophylactic and/or therapeutic agent for age-related macular degeneration, wherein the solid preparation is a tablet.

The prophylactic and/or therapeutic agent for age-related macular degeneration, which is a liquid formulation.

The prophylactic and/or therapeutic agent for age-related macular degeneration, wherein the liquid formulation is an ophthalmic preparation or a capsule.

The prophylactic and/or therapeutic agent for age-related macular degeneration, wherein the age-related macular degeneration is Dry AMD.

The prophylactic and/or therapeutic agent for age-related macular degeneration, wherein the age-related macular degeneration is Wet AMD.

The prophylactic and/or therapeutic agent for age-related macular degeneration, wherein the age-related macular degeneration is No AMD, early AMD and/or intermediate AMD.

A prophylactic and/or therapeutic agent for age-related macular degeneration, including a combination of an angiogenesis inhibitor, and the drusen suppressor.

The prophylactic and/or therapeutic agent for age-related macular degeneration, wherein the angiogenesis inhibitor is an anti-VEGF antibody or a fragment thereof, a fusion protein of a fragment of an anti-VEGF antibody and a Fc domain of an IgG molecule, and/or an anti-angiogenesis aptamer.

The prophylactic and/or therapeutic agent for age-related macular degeneration, wherein the angiogenesis inhibitor is at least one selected from the group consisting of bevacizumab, ranibizumab, aflibercept, pegaptanib sodium, ESBA-1008, lampalizumab, MC-1101, doxycycline hyclate, and emixustat hydrochloride.

The prophylactic and/or therapeutic agent for age-related macular degeneration, wherein the drusen suppressor is an oral agent or an injection.

The prophylactic and/or therapeutic agent for age-related macular degeneration, wherein the oral agent is a solid preparation.

The prophylactic and/or therapeutic agent for age-related macular degeneration, wherein the solid preparation is a tablet.

The prophylactic and/or therapeutic agent for age-related macular degeneration, which is a liquid formulation.

The prophylactic and/or therapeutic agent for age-related macular degeneration, wherein the liquid formulation is an ophthalmic preparation or a capsule.

The prophylactic and/or therapeutic agent for age-related macular degeneration, wherein the age-related macular degeneration is Dry AMD.

The prophylactic and/or therapeutic agent for age-related macular degeneration, wherein the age-related macular degeneration is Wet AMD.

The prophylactic and/or therapeutic agent for age-related macular degeneration, wherein the age-related macular degeneration is No AMD, early AMD and/or intermediate AMD.

A method for inducing drusen in vitro, including:
bringing at least one selected from the group consisting of a cytokine, a growth factor, and a chemokine into contact with cells.

The method, wherein the cells are retinal pigment epithelial cells.

The method, wherein the cells are ARPE-19.

The method, wherein the cytokine is at least one selected from the group consisting of IL-1p, IL-4, IL-5, IL-6, IL-10, IL-12, IL-13, IL-16, TNF-α, and IFN-γ.

The method, wherein the growth factor is at least one selected from the group consisting of TGF-P, FGFs, HGF, EGF, and PDGF.

The method, wherein the chemokine is at least one selected from the group consisting of IL-8, MIP-1α, MCP-1, RANTES, and eotaxin.

The method, wherein a time for the contacting step is 10 minutes to 108 hours.

The method, wherein a temperature in the contacting step is 4 to 50° C.

The method, including assessing the induction of drusen by using an epithelial marker, a mesenchymal marker, secretion of ECM, enhancement of mobility, and/or formation of Focus as an index.

A method for assessing or screening a drusen suppressor, including measuring suppression of epithelial-mesenchymal transition in retinal pigment epithelial cells in vitro in the presence of a test drug.

A method for assessing or screening a drusen suppressor, including measuring suppression of agglomeration of retinal pigment epithelial cells in vitro in the presence of a test drug.

A method for assessing or screening a prophylactic and/or therapeutic agent for age-related macular degeneration, including measuring suppression of epithelial-mesenchymal transition in retinal pigment epithelial cells in vitro in the presence of a test drug.

A method for assessing or screening a prophylactic and/or therapeutic agent for age-related macular degeneration, including measuring suppression of agglomeration of retinal pigment epithelial cells in vitro in the presence of a test drug.

The method for assessing or screening, including:
bringing at least one selected from the group consisting of a cytokine, a growth factor, and a chemokine into contact with the retinal pigment epithelial cells.

The method for assessing or screening, wherein the retinal pigment epithelial cells are ARPE-19.

The method for assessing or screening, wherein the cytokine is at least one selected from the group consisting of IL-1β, IL-4, IL-5, IL-6, IL-10, IL-12, IL-13, IL-16, TNF-α, and IFN-γ.

The method for assessing or screening, wherein the growth factor is at least one selected from the group consisting of TGF-β, FGFs, HGF, EGF, and PDGF.

The method for assessing or screening, wherein the chemokine is at least one selected from the group consisting of IL-8, MIP-106, MCP-1, RANTES, and eotaxin.

The method for assessing or screening, wherein a time for the contacting step is 10 minutes to 108 hours.

The method for assessing or screening, wherein a temperature in the contacting step is 4 to 50° C.

Use of a compound having an activity of suppressing epithelial-mesenchymal transition, for production of a prophylactic and/or therapeutic agent for choroidal neovascularization.

Use of a compound having an activity of suppressing epithelial-mesenchymal transition for production of a VEGF production suppressor.

Use of a compound having an activity of suppressing epithelial-mesenchymal transition for production of a drusen suppressor.

Use of a compound having a compound having an activity of suppressing epithelial-mesenchymal transition, for production of a prophylactic and/or therapeutic agent for age-related macular degeneration.

The use of the compound, wherein the compound having an activity of suppressing epithelial-mesenchymal transition is an agent that suppresses expression of a mesenchymal marker or an extracellular matrix in the retinal pigment epithelial cells.

The use of the compound, wherein the mesenchymal marker is at least one selected from the group consisting of Snail, Slug, CDH3, MMP1, MMP7, MMP3, ZEB2, CDH2, and VIM.

The use of the compound, wherein the extracellular matrix is at least one selected from the group consisting of COL5A3, COL6A3, LAMC2, HMMR, TNC, COL1A1, COL1A2, SRGN, FN1, COL5A2, COL13A1, and LAMB3.

The use of the compound, wherein the mesenchymal marker is at least one selected from the group consisting of Snail, Slug, cadherin3, MMP1, and MMP7, and/or, the extracellular matrix is at least one selected from the group consisting of COL5A3, COL6A3, LAMC2, HMMR, and TNC.

The use of the compound, wherein the compound having an activity of suppressing epithelial-mesenchymal transition is a nonsteroidal anti-inflammatory drug, an aldose reductase inhibitor, a leukotriene receptor antagonist, a chemical mediator release suppressor, and/or a thromboxane A2 receptor antagonist.

Use of the compound, wherein the nonsteroidal anti-inflammatory drug is a propionic acid-based nonsteroidal anti-inflammatory drug, an aminoaryl carboxylic acid-based nonsteroidal anti-inflammatory drug, or an aryl acetic acid-based nonsteroidal anti-inflammatory drug, and the leukotriene receptor antagonist is an antagonist of cysteinyl leukotriene type 1 (CysLT1) receptor or a 5-lipoxygenase inhibitor.

The use of the compound, wherein the propionic acid-based nonsteroidal anti-inflammatory drug is at least one selected from the group consisting of zaltoprofen, oxaprozin, tiaprofenic acid, ibuprofen, flurbiprofen, and pharmaceutically acceptable salts thereof, the aminoaryl carboxylic acid-based nonsteroidal anti-inflammatory drug is at least one selected from the group consisting of flufenamic acid, mefenamic acid, and pharmaceutically acceptable salts thereof, the aryl acetic acid-based nonsteroidal anti-inflammatory drug is sulindac and/or a pharmaceutically acceptable salt thereof, the aldose reductase inhibitor is epalrestat and/or a pharmaceutically acceptable salt thereof, the leukotriene receptor antagonist is at least one selected from the group consisting of zafirlukast, montelukast, pranlukast, and pharmaceutically acceptable salts thereof, the chemical mediator release suppressor is amlexanox and/or a pharmaceutically acceptable salt thereof, and/or, the thromboxane A2 receptor antagonist is seratrodast and/or a pharmaceutically acceptable salt thereof.

The use of the compound, wherein the compound having an activity of suppressing epithelial-mesenchymal transition is at least one selected from the group consisting of Alisertib, MK-0457 (Tozasertib), PHA-739358 (danusertib), AMG-900, Barasertib, CYC116, MLN8054, Baicalin, Baicalein, Lupeol, Istanbulin A, Phytol, Diphenyl difluoroketone (EF24), Crucmin, Phloroglucinol, Plumbagin, Rapamycin, FK506 (Tacrolimus), Thalidomide, LY550410, SB-505124, SD-208, TAPI-0, TAPI-1, JNJ-38877605, PF-04217903, AG1478 (Tyrphostin), Erlotinib, Gefitinib, Lapatinib, PD153035, PD158780, WHI-P154, BMS-536924, A83-01, D4476, LY-364947, SB-431542, SD-208, AZD6244 (Selumetinib), CI-1040, PD0325901, GDC-0941 (Pictilisib), PI-103, PIK-90, ZSTK474, API-2, AZD0530 (Saracatinib), PP1, 2-Hydroxycinnamaldehyde, 5-aza-dC, BI 5700, Celecoxib, CX-4945 (Silmitasertib), Disulfiram, Eribulin mesyate, Evodiamine, EW-7203, Fasudil, Nintedanib, Fuzheng Huayu recipe, Grape seed proanthocyanidins, Vorinostat, Herbimycin A, Entinostat, Honokiol, NPI-0052, Methacycline, Dasatinib, Ki26894, NSC 74859, NVP-LDE-225 (Erismodegib), Palbociclib, Pinocembrin, Salvianolic Acid B, Sorafenib, Resveratrol, S-Allylcysteine, Silibinin meglumine, Simvastatin, Centchroman, ML327, GN-25, TrichostatinA, Sarasinoside A1, Panobinostat, Danusertib, Cystatin C, Thymoquinone, Ulinastatin, Dendrofalconerol A (DF-A), ginsenoside (carrot saponin), staff tree seed extract, salicin (white willow extract), salicylic acid, hedge parsley extract, osthol, Muscadine grape skin extract, Tongxinluo, procyanidin C1 (cinnamon), ashwagandha root extract (Withania somnifera root extract), Qingyihuaji, roselle extract, gallic acid epigallocatechin, proanthocyanidin (grape seed extract), and Salvianolic acid B.

The use of the compound, which is an oral agent or an injection.

The use of the compound, wherein the oral agent is a solid preparation.

The use of the compound, wherein the solid preparation is a tablet.

The use of the compound, which is a liquid formulation.

The use of the compound, wherein the liquid formulation is an ophthalmic preparation or a capsule.

A compound having an activity of suppressing epithelial-mesenchymal transition for use in prophylaxis and/or therapy of choroidal neovascularization.

A compound having an activity of suppressing epithelial-mesenchymal transition for use in suppression of production of VEGF.

A compound having an activity of suppressing epithelial-mesenchymal transition for use in suppression of drusen.

A compound having an activity of suppressing epithelial-mesenchymal transition for use in prophylaxis and/or therapy of age-related macular degeneration.

The compound, wherein the compound having an activity of suppressing epithelial-mesenchymal transition is an agent that suppresses expression of a mesenchymal marker or an extracellular matrix in the retinal pigment epithelial cells.

The compound, wherein the mesenchymal marker is at least one selected from the group consisting of Snail, Slug, CDH3, MMP1, MMP7, MMP3, ZEB2, CDH2, and VIM.

The compound, wherein the extracellular matrix is at least one selected from the group consisting of COL5A3, COL6A3, LAMC2, HMMR, TNC, COL1A1, COL1A2, SRGN, FN1, COL5A2, COL13A1, and LAMB3.

The compound, wherein the mesenchymal marker is at least one selected from the group consisting of Snail, Slug, cadherin3, MMP1, and MMP7, and/or, the extracellular matrix is at least one selected from the group consisting of COL5A3, COL6A3, LAMC2, HMMR, and TNC.

The compound, wherein the compound having an activity of suppressing epithelial-mesenchymal transition is a nonsteroidal anti-inflammatory drug, an aldose reductase inhibitor, a leukotriene receptor antagonist, a chemical mediator release suppressor, and/or a thromboxane A2 receptor antagonist.

The compound, wherein the nonsteroidal anti-inflammatory drug is a propionic acid-based nonsteroidal anti-inflammatory drug, an aminoaryl carboxylic acid-based nonsteroidal anti-inflammatory drug, or an aryl acetic acid-based nonsteroidal anti-inflammatory drug, and the leukotriene receptor antagonist is an antagonist of cysteinyl leukotriene type 1 (CysLT1) receptor or a 5-lipoxygenase inhibitor.

The compound, wherein the propionic acid-based nonsteroidal anti-inflammatory drug is at least one selected from the group consisting of zaltoprofen, oxaprozin, tiaprofenic acid, ibuprofen, flurbiprofen, and pharmaceutically acceptable salts thereof, the aminoaryl carboxylic acid-based nonsteroidal anti-inflammatory drug is at least one selected from the group consisting of flufenamic acid, mefenamic acid, and pharmaceutically acceptable salts thereof, the aryl acetic acid-based nonsteroidal anti-inflammatory drug is sulindac and/or a pharmaceutically acceptable salt thereof, the aldose reductase inhibitor is epalrestat and/or a pharmaceutically acceptable salt thereof, the leukotriene receptor antagonist is at least one selected from the group consisting of zafirlukast, montelukast, pranlukast, and pharmaceutically acceptable salts thereof, the chemical mediator release suppressor is amlexanox and/or a pharmaceutically acceptable salt thereof, and/or, the thromboxane A2 receptor antagonist is seratrodast and/or a pharmaceutically acceptable salt thereof.

The compound, wherein the compound having an activity of suppressing epithelial-mesenchymal transition is at least one selected from the group consisting of Alisertib, MK-0457 (Tozasertib), PHA-739358 (danusertib), AMG-900, Barasertib, CYC116, MLN8054, Baicalin, Baicalein, Lupeol, Istanbulin A, Phytol, Diphenyl difluoroketone (EF24), Crucmin, Phloroglucinol, Plumbagin, Rapamycin, FK506 (Tacrolimus), Thalidomide, LY550410, SB-505124, SD-208, TAPI-0, TAPI-1, JNJ-38877605, PF-04217903, AG1478 (Tyrphostin), Erlotinib, Gefitinib, Lapatinib, PD153035, PD158780, WHI-P154, BMS-536924, A83-01, D4476, LY-364947, SB-431542, SD-208, AZD6244 (Selumetinib), CI-1040, PD0325901, GDC-0941 (Pictilisib), PI-103, PIK-90, ZSTK474, API-2, AZD0530 (Saracatinib), PP1, 2-Hydroxycinnamaldehyde, 5-aza-dC, BI 5700, Celecoxib, CX-4945 (Silmitasertib), Disulfiram, Eribulin mesyate, Evodiamine, EW-7203, Fasudil, Nintedanib, Fuzheng Huayu recipe, Grape seed proanthocyanidins, Vorinostat, Herbimycin A, Entinostat, Honokiol, NPI-0052, Methacycline, Dasatinib, Ki26894, NSC 74859, NVP-LDE-225 (Erismodegib), Palbociclib, Pinocembrin, Salvianolic Acid B, Sorafenib, Resveratrol, S-Allylcysteine, Silibinin meglumine, Simvastatin, Centchroman, ML327, GN-25, TrichostatinA, Sarasinoside A1, Panobinostat, Danusertib, Cystatin C, Thymoquinone, Ulinastatin, Dendrofalconerol A (DF-A), ginsenoside (carrot saponin), staff tree seed extract, salicin (white willow extract), salicylic acid, hedge parsley extract, osthol, Muscadine grape skin extract, Tongxinluo, procyanidin C1 (cinnamon), ashwagandha root extract (Withania somnifera root extract), Qingyihuaji, roselle extract, gallic acid epigallocatechin, proanthocyanidin (grape seed extract), and Salvianolic acid B.

The compound, which is an oral agent or an injection.

The compound, wherein the oral agent is provided in the form of a solid preparation.

The compound, wherein the solid preparation is a tablet.

The compound, provided in the form of a liquid formulation.

The compound, wherein the liquid formulation is an ophthalmic preparation or a capsule.

EXAMPLES

The present invention will be described specifically by the following examples, however, it is to be noted that the present invention is not limited to these examples.

Test example 1 to Test example 3 and Reference test example 2-4 show the tests regarding prophylaxis and/or therapy of CNV.

Test example 4 to Test example 8 show the tests regarding prophylaxis and/or therapy of drusen.

Test Example 1

Construction of EMT Cell Model

Test Example 1-1

Consideration of Induction Condition of EMT in RPE Cells

The present inventors made experiments of testing for stimulation in ten different conditions on RPE cells (retinal pigment epithelial cells strain: ARPE-19, the same applies hereinafter) using a cytokine or a growth factor (TNF-α/IL-1β/TGF-β), and found that significant EMT induction is caused. It is considered that a EMT induction cell model using a cytokine or a growth factor reflects an estimated EMT induction mechanism in a patient associated with CNV.

The ten different conditions are as follows.
(1) TNF-α 100 ng/mL
(2) IL-1β 100 ng/mL
(3) IL-1β 20 ng/mL
(4) TNF-α 500 ng/mL+TGF-β 5 ng/mL
(5) TNF-α 200 ng/mL+TGF-β 5 ng/mL
(6) TNF-α 100 ng/mL+TGF-β 5 ng/mL
(7) TNF-α 100 ng/mL+TGF-β 10 ng/mL
(8) TNF-α 100 ng/mL+TGF-β 25 ng/mL
(9) IL-1β 100 ng/mL+TGF-β 5 ng/mL
(10) IL-1β 20 ng/mL+TGF-β 5 ng/mL Test Example 1-2

Verification of EMT by Change in Expression of EMT Marker Molecule

RNA was extracted from RPE cells after stimulation, and change in expression was verified.

RPE cells (ARPE-19) were seeded on a plate, and incubated for 5 days at 37° C. For the RPE cells, EMT was induced by the conditions described in Test example 1-1, and the cells were collected after 48 hours from the EMT induction. The collected cells were washed with PBS, and 350 μL of an RLT buffer (available from QIAGEN) was added to prepare a lysate for RNA extraction. Total RNA was extracted from the lysate using an RNeasy Micro kit (QIAGEN, #74004), and from 2 μg of the obtained RNA, cDNA was prepared using a SuperScript III First-Strand Synthesis SuperMix for qRT-PCR (Invitrogen, #11752-250). Using 50 ng of the obtained cDNA as a template, a real-time PCR (ABI Prism 7500 Sequence Detection System) was conducted according to the manufacturer's protocol, and expression of mRNA of each gene was quantified. Specific primers for respective genes were purchased from Invitrogen. Ct (Threshold Cycle) value of each gene was calculated as a percentage to a non-treated sample after normalization by endogenous control. The results are shown in FIG. 1.

As shown in FIGS. 1A and B, in the RPE cells after stimulation, expression of E-Cadherin which is an epithelial marker was decreased (FIG. 1A), and expression of N-cadherin which is a mesenchymal marker was enhanced (FIG. 1B). Such cadherin switching is a representative phenomenon of EMT. Also enhancement in a mesenchymal marker represented by fibronectin (FIG. 1C) and a EMT-related transcription factor group (Snail, Slug, ZEB1) (FIG. 1E to G), and enhancement in expression of ECM represented by type I collagen (COL1A1) were observed (FIG. 1D), and it was confirmed that EMT is induced by stimulation in RPE cells.

Test Example 1-3

Verification of Time-Varying Change in Expression of EMT Marker by Microarray

The EMT induction state at a time in the EMT induction time was analyzed.

RPE cells (ARPE-19) were seeded on a plate, and incubated for 5 days at 37° C. For RPE cells, EMT was induced in the conditions as described in Test example 1-1, and cells were collected after 1 hour, after 4 hours, 12 hours, 24 hours, 48 hours and 72 hours from induction of EMT. The collected cells were washed with PBS, and 350 μL of an RLT buffer was added to prepare a lysate for RNA extraction. Total RNA was extracted from the lysate using an RNeasy Micro kit (QIAGEN, #74004), and fluorescent-labeled with a Low Input QuickAmp Labeling kit (Agilent Technologies, # 5190-2305). The labeled cRNA was hybridized with a Whole Human Genome Oligo-DNA Microarray Kit (Agilent Technologies, # G 4112F) according to the protocol prescribed by the manufacturer. The hybridized slide was washed with a Gene Expression Wash Pack (Agilent Technologies, # 5188-5327), and scanned with an Agilent Microarray Scanner (Agilent Technologies, # G 2505B). The scanned image was digitized by using a Feature Extraction software version 9.5.1 (available from Agilent Technologies). The numerical data was normalized by a Grobal Normalization method. The results are shown in FIG. 2.

Figure 2:
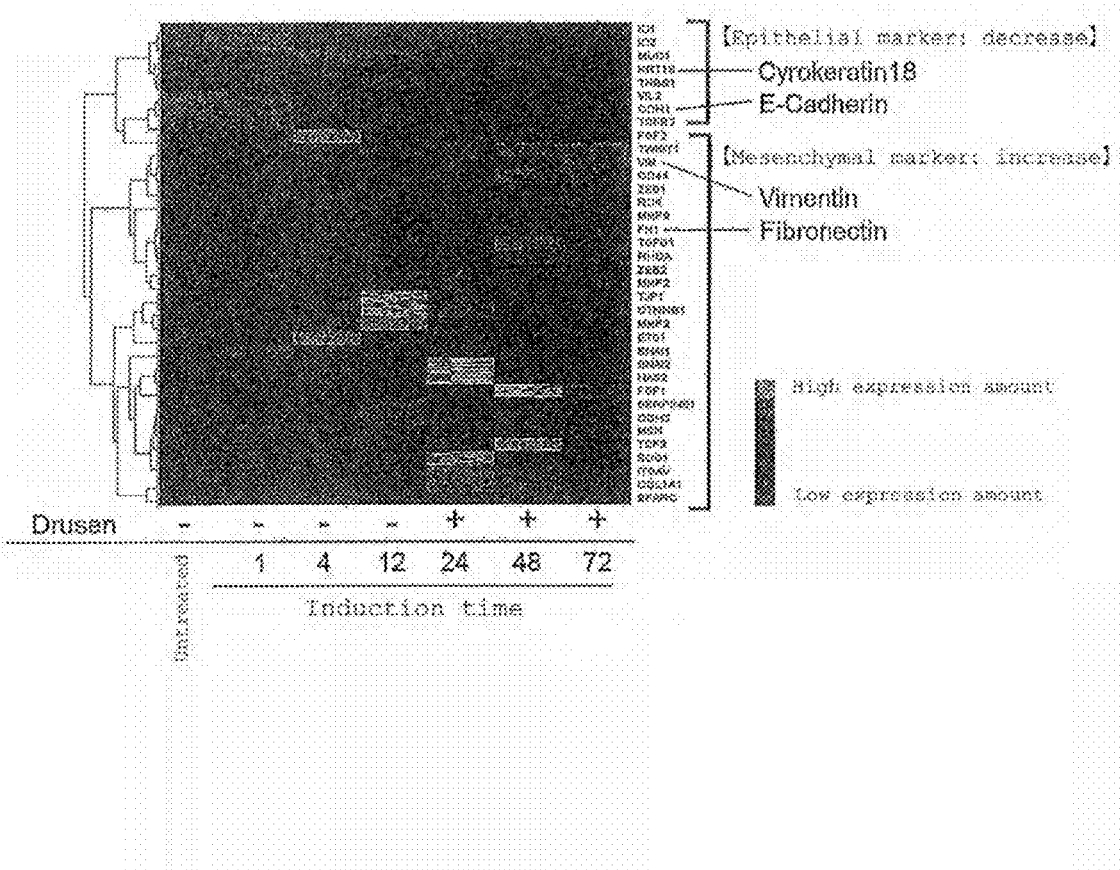
FIG. 2 shows a chart showing the results of EMT induction in RPE cells, verified by time-varying change in expression of EMT markers.

As shown in FIG. 2, the peaks of decrease or increase of the EMT markers occurred variably depending on the particular gene, as observed after 12 hours or 72 hours from induction of EMT, and decreased epithelial markers and enhanced mesenchymal markers and ECMs are as follows.

As epithelial markers decreased by induction of EMT, ID1, ID2, MUC1, Cytokeratin 18 (KRT18), THBS1, VIL2, and E-Cadherin (CDH1) were confirmed. Also, decrease in TGFB2 which is a growth factor was confirmed.

As the mesenchymal markers and ECMs that were enhanced by induction of EMT, TWIST1, VIM, CD44, ZEB1, RDX, MMP9, FN1, RHOA, ZEB2, MMP2, TJP1, CTNNB1, MMP3, ETS1, SNAIL SNAI2, HAS2, SERPINE1, CDH2, MSN, TCF3, SDC1, ITGAV, COL1A1, and SPARC were confirmed. Also, enhancement in FGF1, FGF2, and TGFB1 which are growth factors was confirmed.

Test Example 2

CNV Suppressing Test

Test Example 2-1

Change in Expression of EMT Marker 1

Five compounds (oxaprozin, epalrestat, zafirlukast, amlexanox, zaltoprofen) were assessed for an EMT suppressive effect using the cell model as described above.

RPE cells (ARPE-19) were seeded on a plate, and incubated for 5 days at 37° C. For the RPE cells, EMT was induced in the conditions described in Test example 1-1, and respective compounds (oxaprozin, epalrestat, zafirlukast, amlexanox, zaltoprofen) were added simultaneously, and the cells were collected after 48 hours from induction of EMT. As a control, a sample to which a compound to be assessed (test drug) is not added was used. The collected cells were washed with PBS, and 350 µL of an RLT buffer was added to prepare a lysate for RNA extraction. The respective compounds were used in the following concentrations. Oxaprozin: 300 µM, epalrestat: 30 µM, zafirlukast: 3 µM, amlexanox: 30 µM, zaltoprofen: 30 µM. Total RNA was extracted from the lysate using an RNeasy Micro kit (QIAGEN, #74004), and from 2 µg of the obtained RNA, cDNA was prepared using a SuperScript III First-Strand Synthesis SuperMix for qRT-PCR (Invitrogen, #11752-250). Using 50 ng of the obtained cDNA as a template, a real-time PCR (ABI Prism 7500 Sequence Detection System) was conducted according to the manufacturer's protocol, and expression of mRNA of each gene was quantified. Specific primers for respective genes were purchased from Invitrogen. Ct (Threshold Cycle) value of each gene was calculated as a percentage to a non-treated sample after normalization by endogenous control. The results are shown in FIG. 3 to FIG. 7.

In each graph of FIG. 3 to FIG. 7, the left bar graph indicates an expression amount of each gene when EMT is not induced. The center bar graph indicates an expression amount of each gene when EMT is induced. The right bar graph indicates an expression amount of each gene when an EMT suppressive compound is administered. Also, FIG. 3 to FIG. 7 indicate the results using oxaprozin, epalrestat, zafirlukast, amlexanox, and zaltoprofen, respectively as an EMT suppressive compound.

In the present description, the EMT markers are also described respectively by the following abbreviated names.
Cadherin: CDH (CDH2, CDH3, etc.)
Matrix metalloproteinase: MMP (MMP1, MMP3, MMP7, etc.)
Fibronectin: FN (FN1, etc.)
Vimentin: VIM
Collagen type 1α1: COL1A1
Collagen type 1α2: COL1A2
Collagen type 5α2: COL5A2
Collagen type 5α3: COL5A3
Collagen type 6α3: COL6A3
Collagen type 13α1: COL13A1
Laminin β3: LAMB3
Laminin γ2: LAMC2
Hyaluronan-Mediated Motility Receptor: HMMR
Tenascin C: TNC
Zinc Finger E-Box Binding Homeobox 2: ZEB2
Serglycin: SRGN
chondroitin sulfate proteoglycan 4: CSPG4

In each graph of FIGS. 3 to 7, the first stage shows Snail, Slug, CDH3, COL5A3, and COL6A3 from the left, and the second stage shows MMP1, MMP7, LAMC2, HMMR, and TNC from the left.

Figure 3:
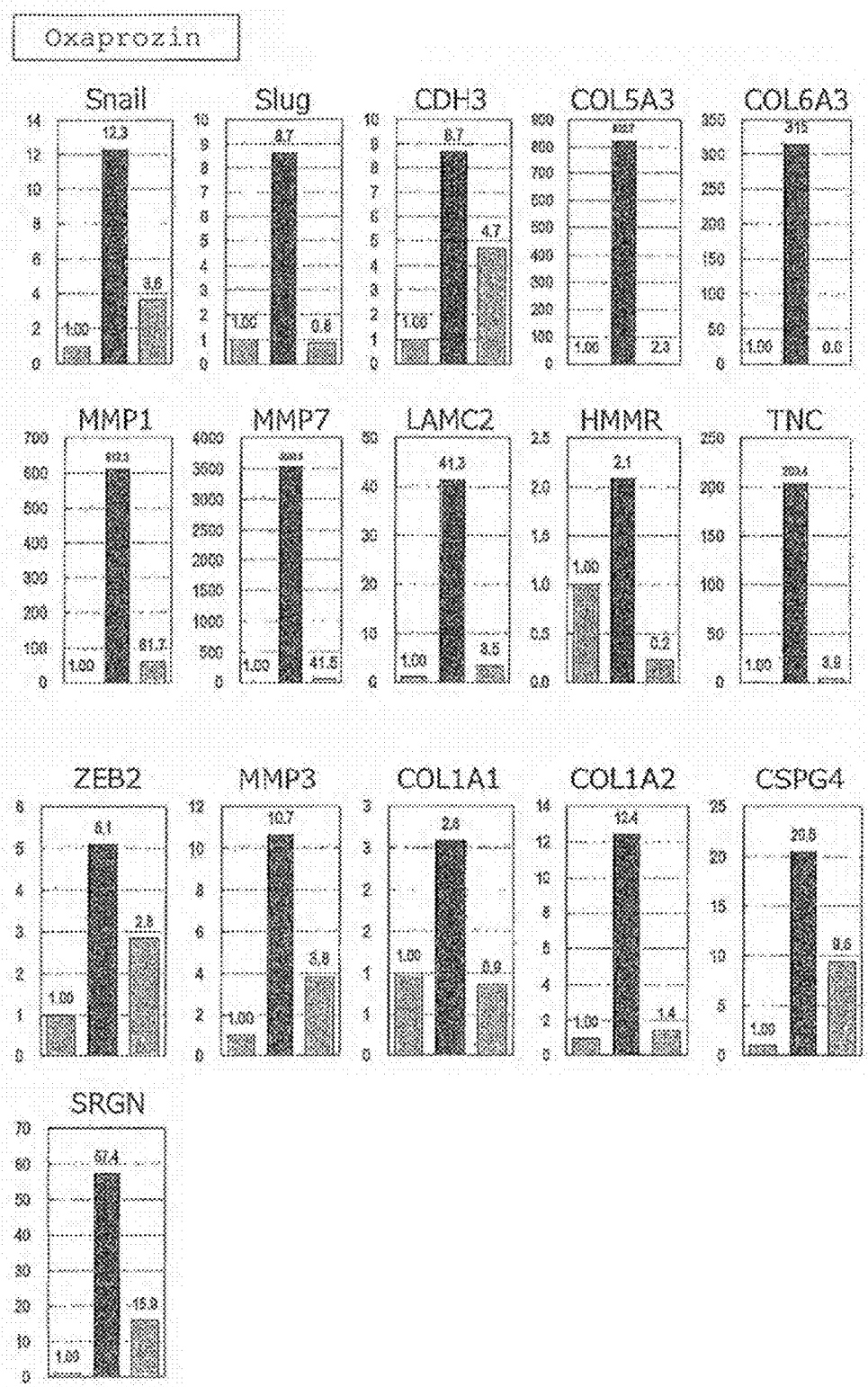
FIG. 3 includes graphs showing that oxaprozin suppresses EMT in RPE cells.

The third stage of FIG. 3 (oxaprozin) shows ZEB2, MMP3, COL1A1, COL1A2, and CSPG4 from the left, and the fourth stage shows SRGN.

Figure 4:
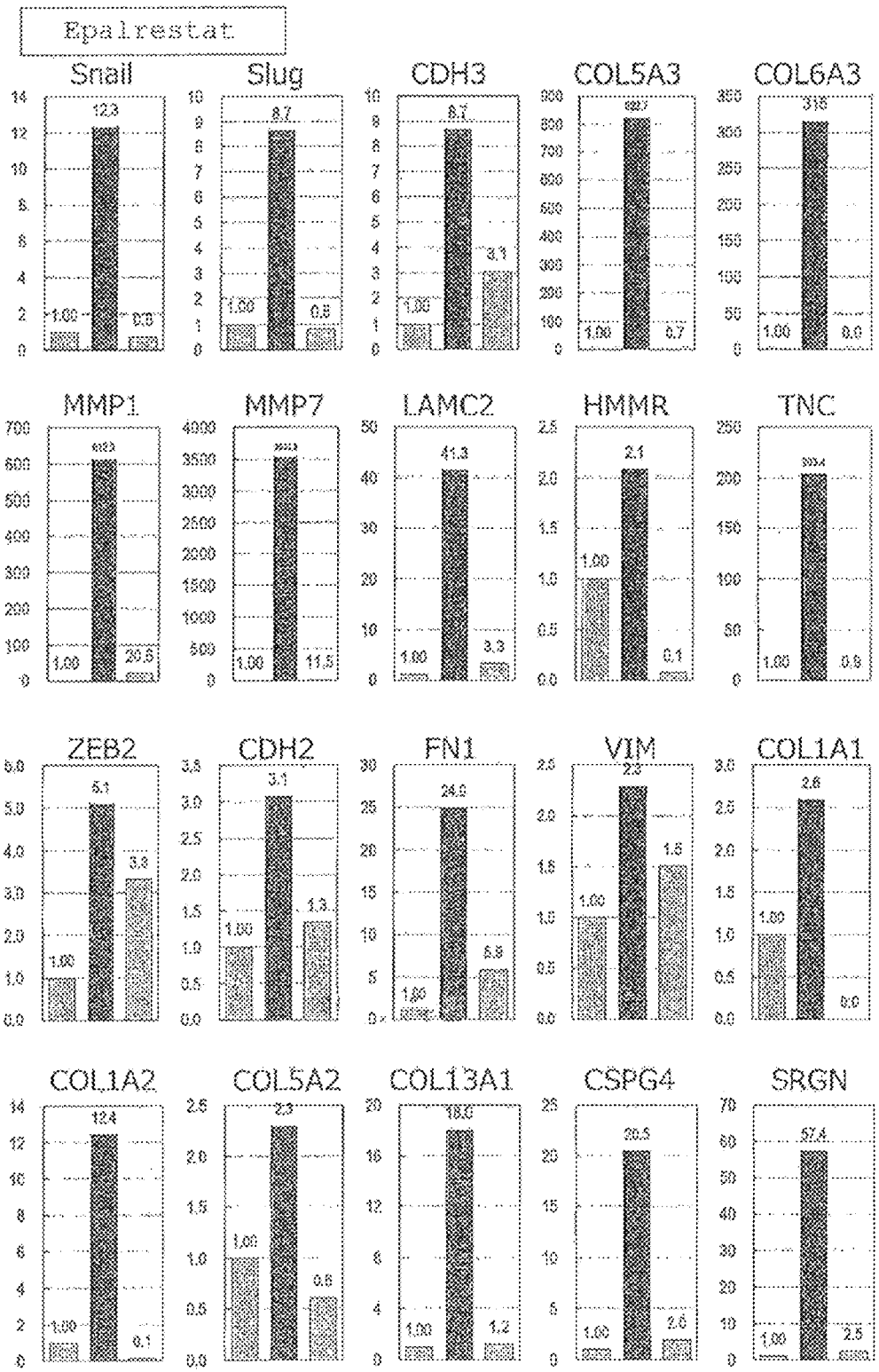
FIG. 4 includes graphs showing that epalrestat suppresses EMT in RPE cells.

The third stage of FIG. 4 (epalrestat) shows ZEB2, CDH2, FN1, VIM, and COL1A1 from the left, and the fourth stage shows COL1A2, COL5A2, COL13A1, CSPG4, and SRGN from the left.

Figure 5:
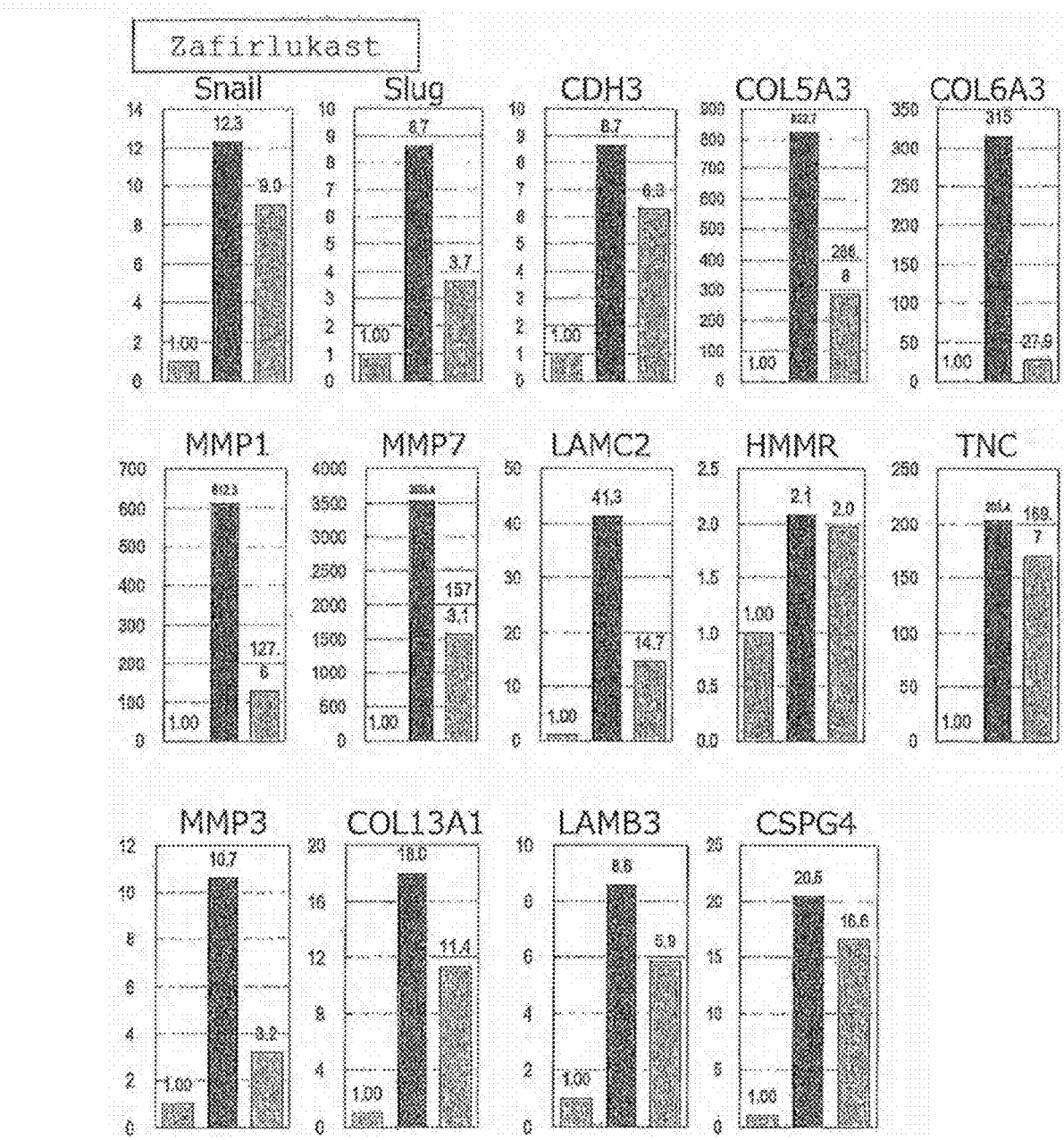
FIG. 5 includes graphs showing that zafirlukast suppresses EMT in RPE cells.

The third stage of FIG. 5 (zafirlukast) shows MMP3, COL13A1, LAMB3, and CSPG4 from the left.

Figure 6:
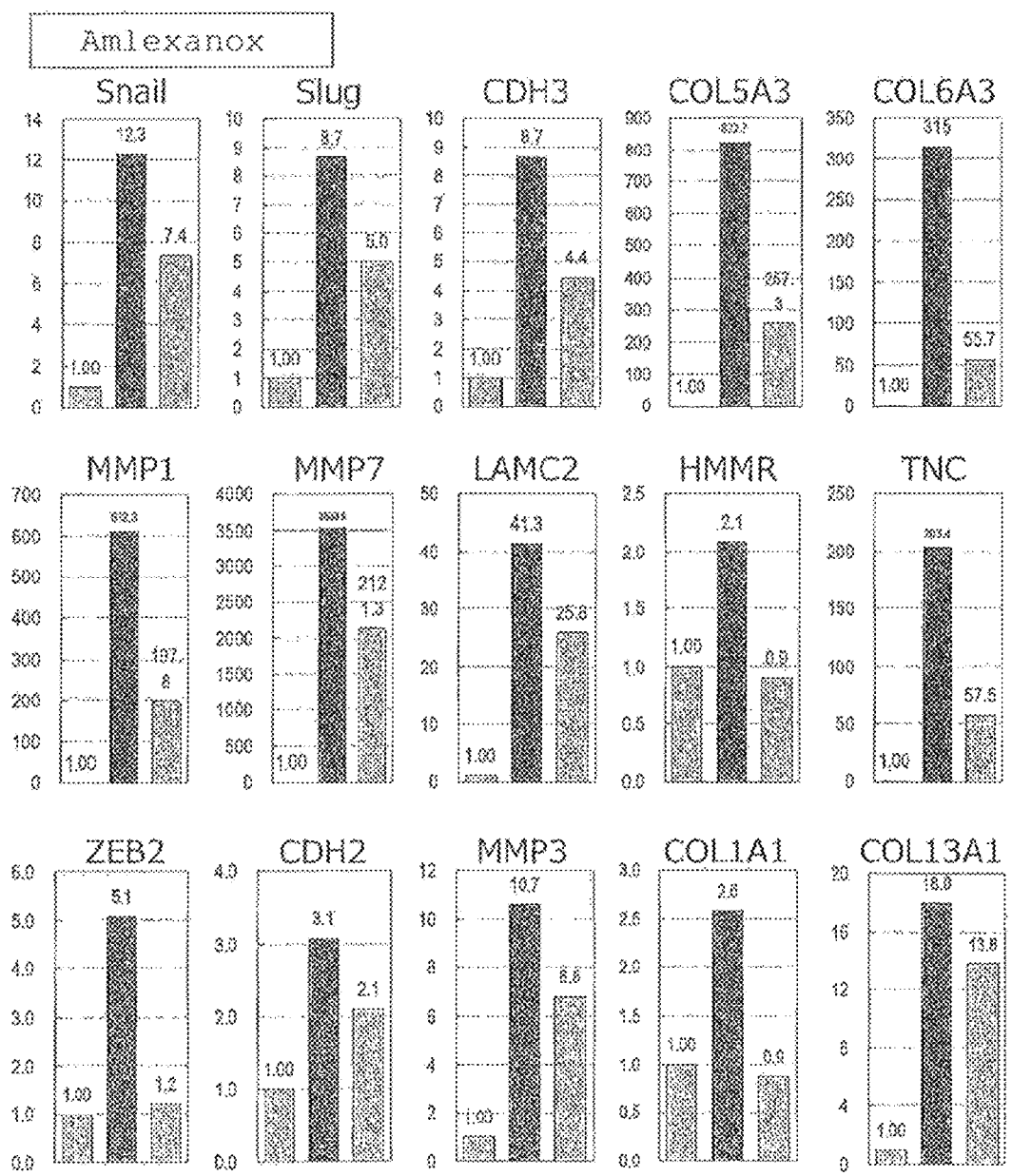
FIG. 6 includes graphs showing that amlexanox suppresses EMT in RPE cells.

The third stage of FIG. 6 (amlexanox) shows ZEB2, CDH2, MMP3, COL1A1, and COL13A1 from the left.

Figure 7:
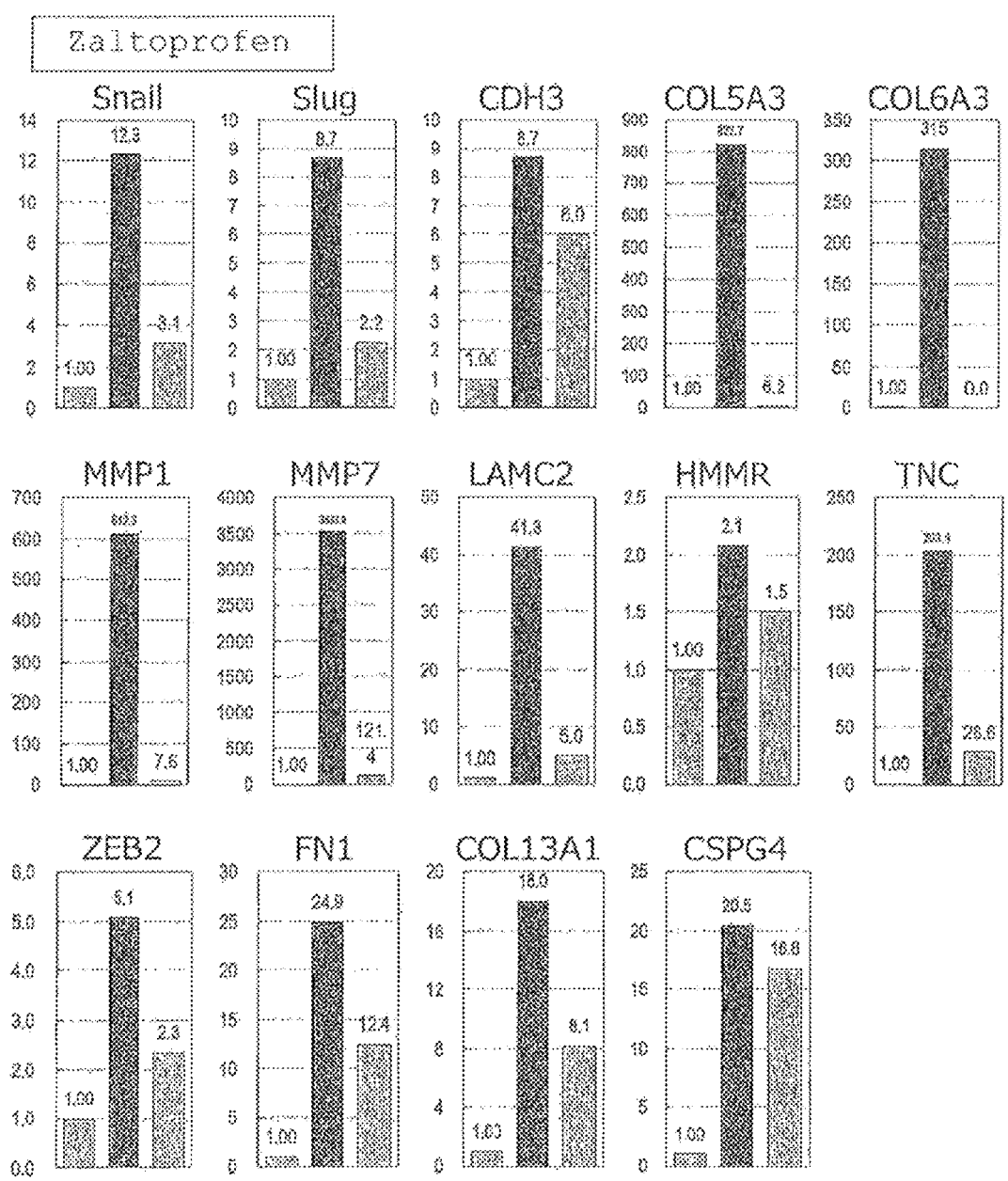
FIG. 7 includes graphs showing that zaltoprofen suppresses EMT in RPE cells.

The third stage of FIG. 7 (zaltoprofen) shows ZEB2, FN1, COL13A1, and CSPG4 from the left.

As shown in FIG. 3 to FIG. 7, among the EMT markers, Snail, Slug, CDH3, MMP1, and MMP7 which are mesenchymal markers, and COL5A3, COL6A3, LAMC2, HMMR, and TNC which are ECMs exhibited suppressed expression regardless of the applied EMT suppressive compound. As a result, these ten EMT markers were confirmed to be indexes that are commonly suppressed by the EMT suppressive compounds. Even with EMT markers other than these ten markers, decrease in expression was observed in ZEB2, MMP3, COL1A1, COL1A2, CSPG4, and SRGN in the case of oxaprozin as shown in FIG. 3. As shown in FIG. 4, decrease in expression was observed in ZEB2, CDH2, FN1, VIM, COL1A1, COL1A2, COL5A2, COL13A1, CSPG4, and SRGN in the case of epalrestat. As shown in FIG. 5, decrease in expression was observed in MMP3, COL13A1, LAMB3, or CSPG4 in the case of zafirlukast. As shown in FIG. 6, decrease in expression was observed in ZEB2, CDH2, MMP3, COL1A1, and COL13A1 in the case of amlexanox. As shown in FIG. 7, decrease in expression was observed in ZEB2, FN1, COL13A1, and CSPG4 in the case of zaltoprofen. It was confirmed that these EMT markers can be indexes that are suppressed by EMT suppressive compounds.

FIG. 3 to FIG. 7 revealed that the five compounds (oxaprozin, epalrestat, zafirlukast, amlexanox, zaltoprofen) significantly suppress EMT. It is considered that these compounds suppress production of VEGF and the like involved in development or extension of CNV by significantly suppressing EMT, and can prevent and/or treat CNV radically.

Test Example 2-2

Change in Expression of EMT Marker 2

Five compounds (flufenamic acid aluminum (addition concentration: 28 µM (Cmax)), mefenamic acid (addition concentration: 39 µm (Cmax)), sulindac (addition concentration: 100 µM), tiaprofenic acid (addition concentration: 1000 µM), and seratrodast (addition concentration: 31 µM (Cmax))) were assessed for change in expression of EMT markers in the same manner as in Test example 2-1. The results are shown in FIG. 8 to FIG. 12, respectively.

Figure 8:
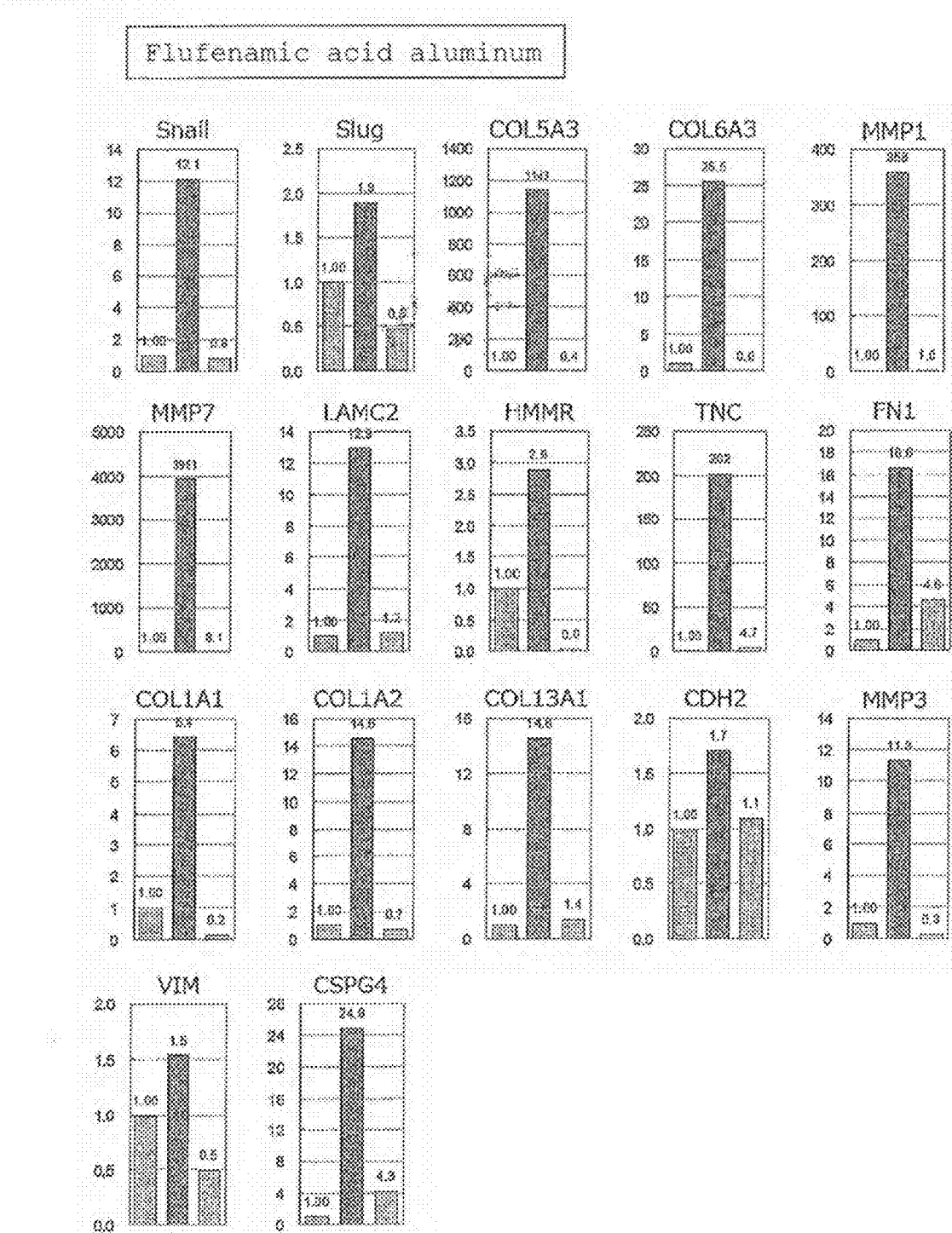
FIG. 8 includes graphs showing that flufenamic acid aluminum suppresses EMT in RPE cells.

The first stage in FIG. 8 (flufenamic acid aluminum) shows Snail, Slug, COL5A3, COL6A3, and MMP1 from the left, the second stage shows MMP7, LAMC2, HMMR, TNC, and FN1 from the left, the third stage shows COL1A1, COL1A2, COL13A1, CDH2, and MMP3 from the left, and the fourth stage shows VIM, and CSPG4 from the left.

Figure 9:
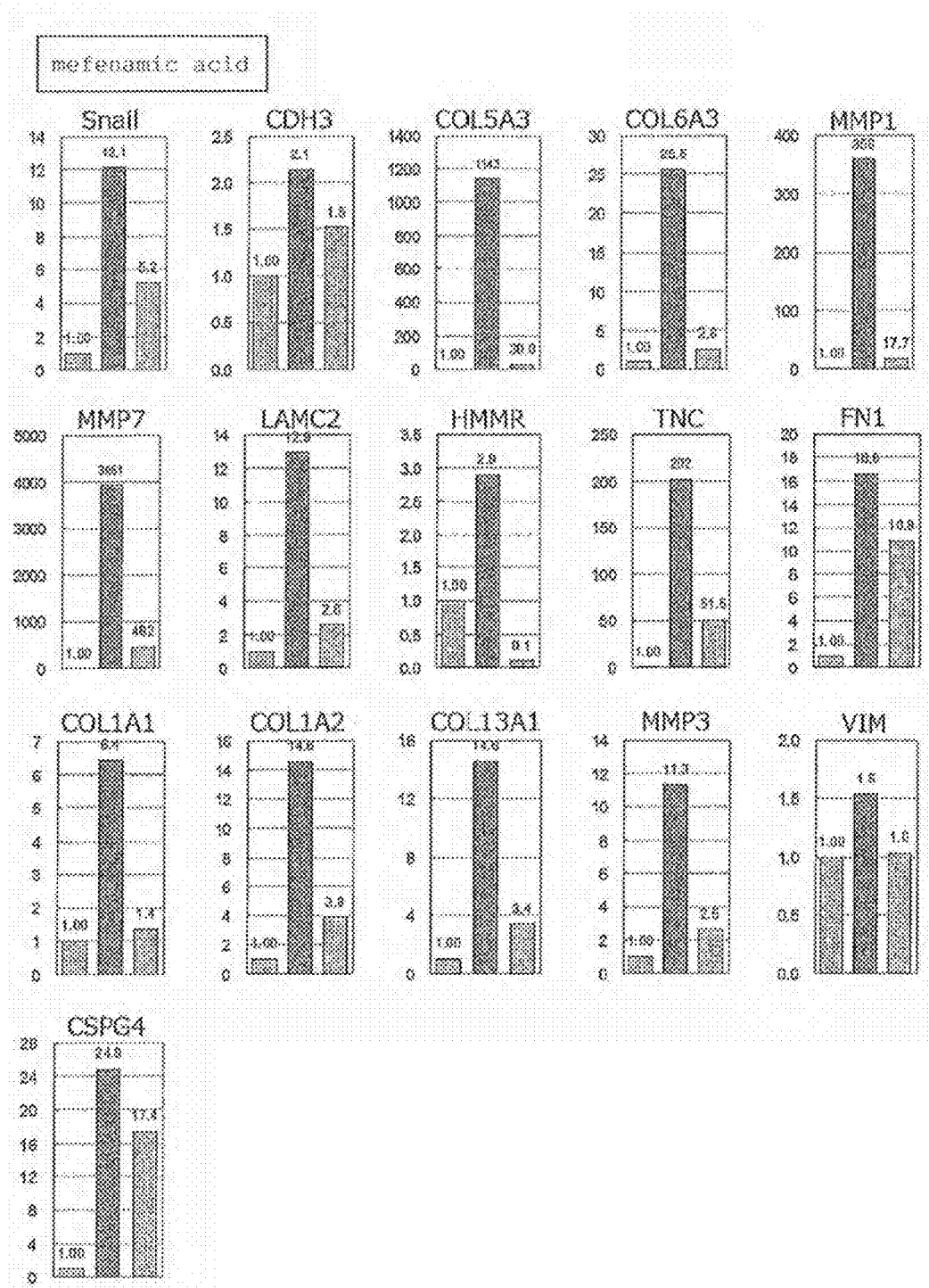
FIG. 9 includes graphs showing that mefenamic acid suppresses EMT in RPE cells.

The first stage in FIG. 9 (mefenamic acid) shows Snail, CDH3, COL5A3, COL6A3, and MMP1 from the left, the second stage shows MMP7, LAMC2, HMMR, TNC, and FN1 from the left, the third stage shows COL1A1, COL1A2, COL13A1, MMP3, and VIM from the left, and the fourth stage shows CSPG4.

Figure 10:
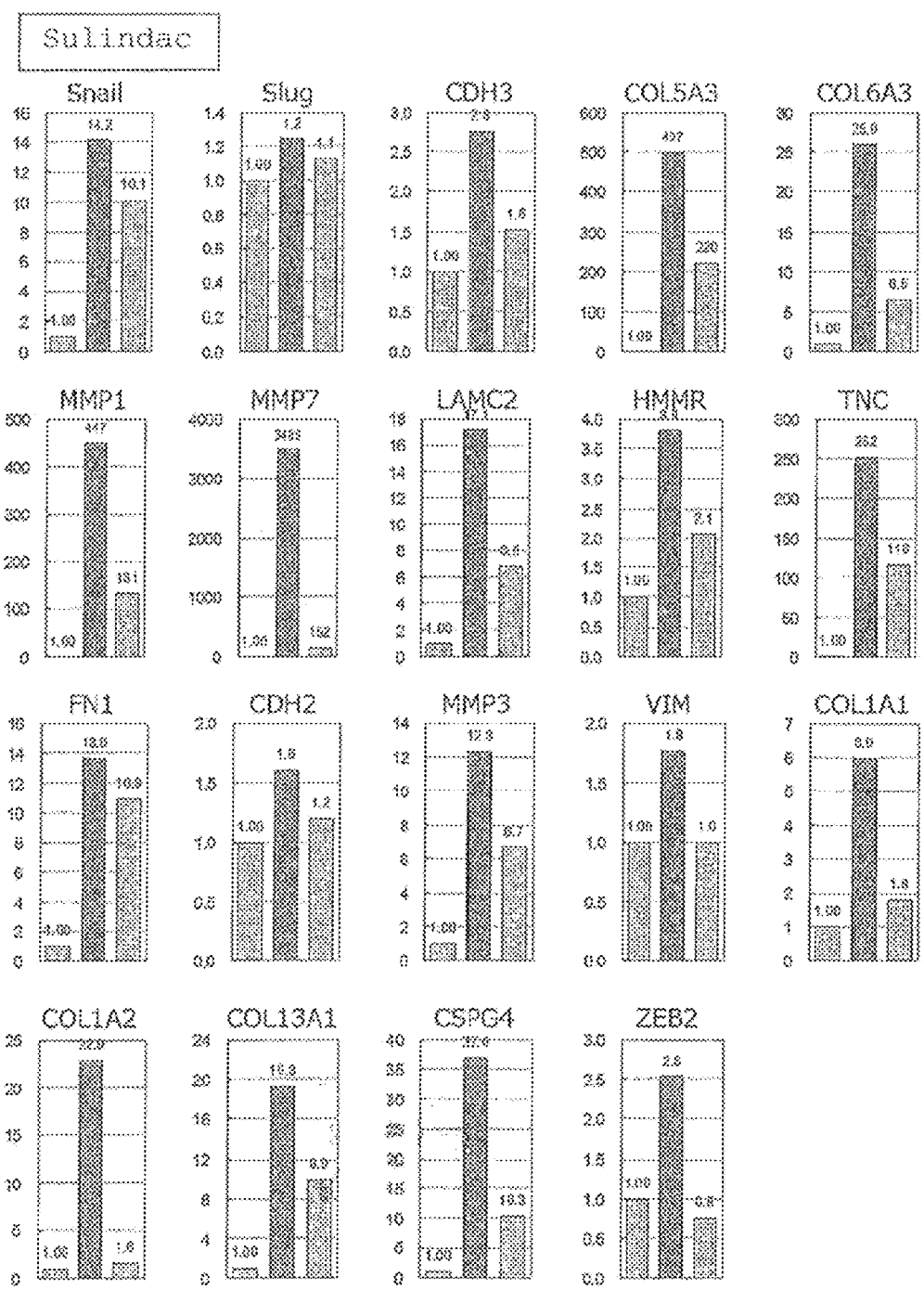
FIG. 10 includes graphs showing that sulindac suppresses EMT in RPE cells.

The first stage in FIG. 10 (sulindac) shows Snail, Slug, CDH3, COL5A3, and COL6A3 from the left, the second stage shows MMP1, MMP7, LAMC2, HMMR, and TNC from the left, the third stage shows FN1, CDH2, MMP3, VIM, and COL1A1 from the left, and the fourth stage shows COL1A2, COL13A1, CSPG4, and ZEB2 from the left.

Figure 11:
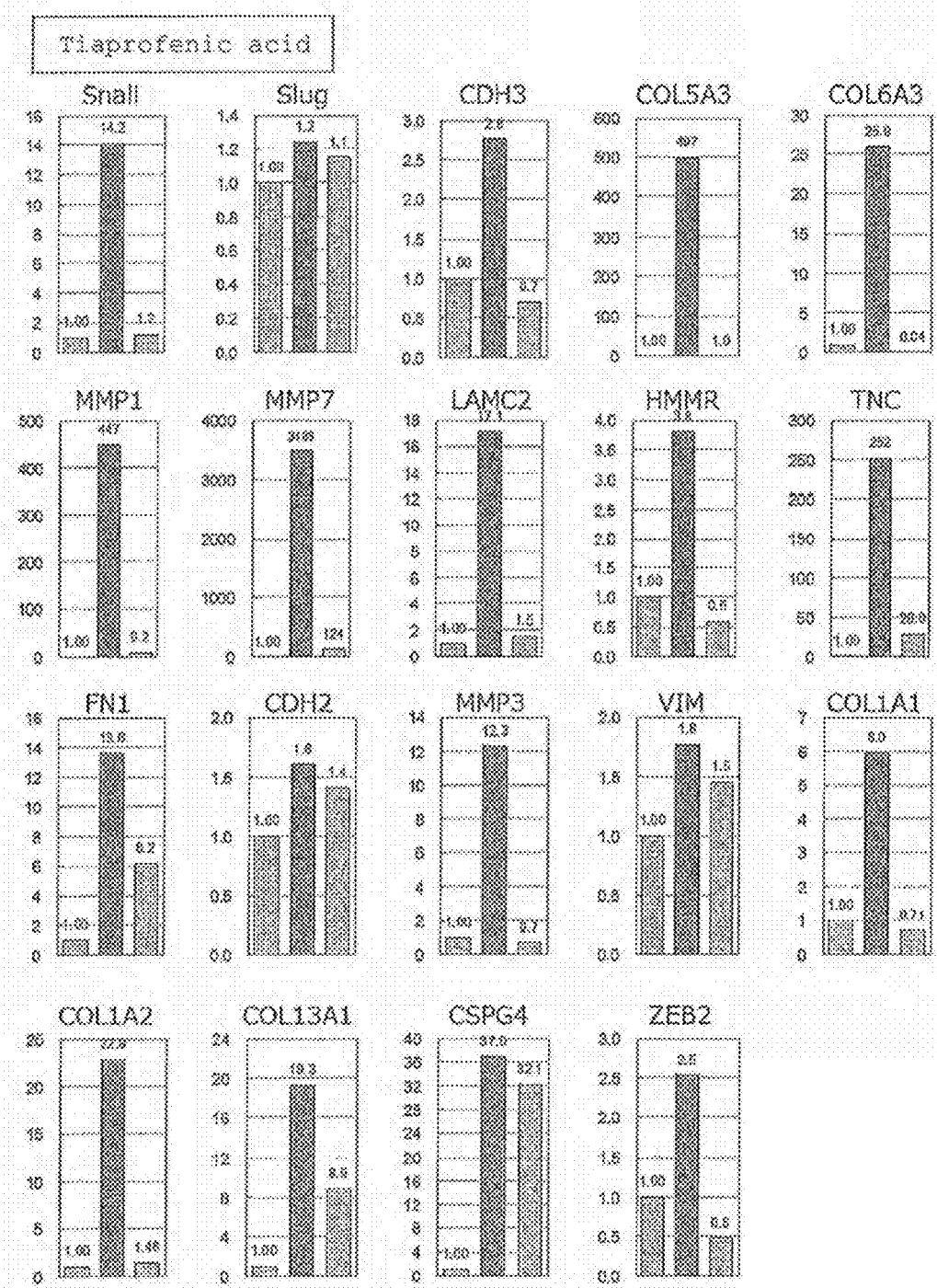
FIG. 11 includes graphs showing that tiaprofenic acid suppresses EMT in RPE cells.

The first stage in FIG. 11 (tiaprofenic acid) shows Snail, Slug, CDH3, COL5A3, and COL6A3 from the left, the second stage shows MMP1, MMP7, LAMC2, HMMR, and TNC from the left, the third stage shows FN1, CDH2, MMP3, VIM, and COL1A1 from the left, and the fourth stage shows COL1A2, COL13A1, CSPG4, and ZEB2 from the left.

Figure 12:
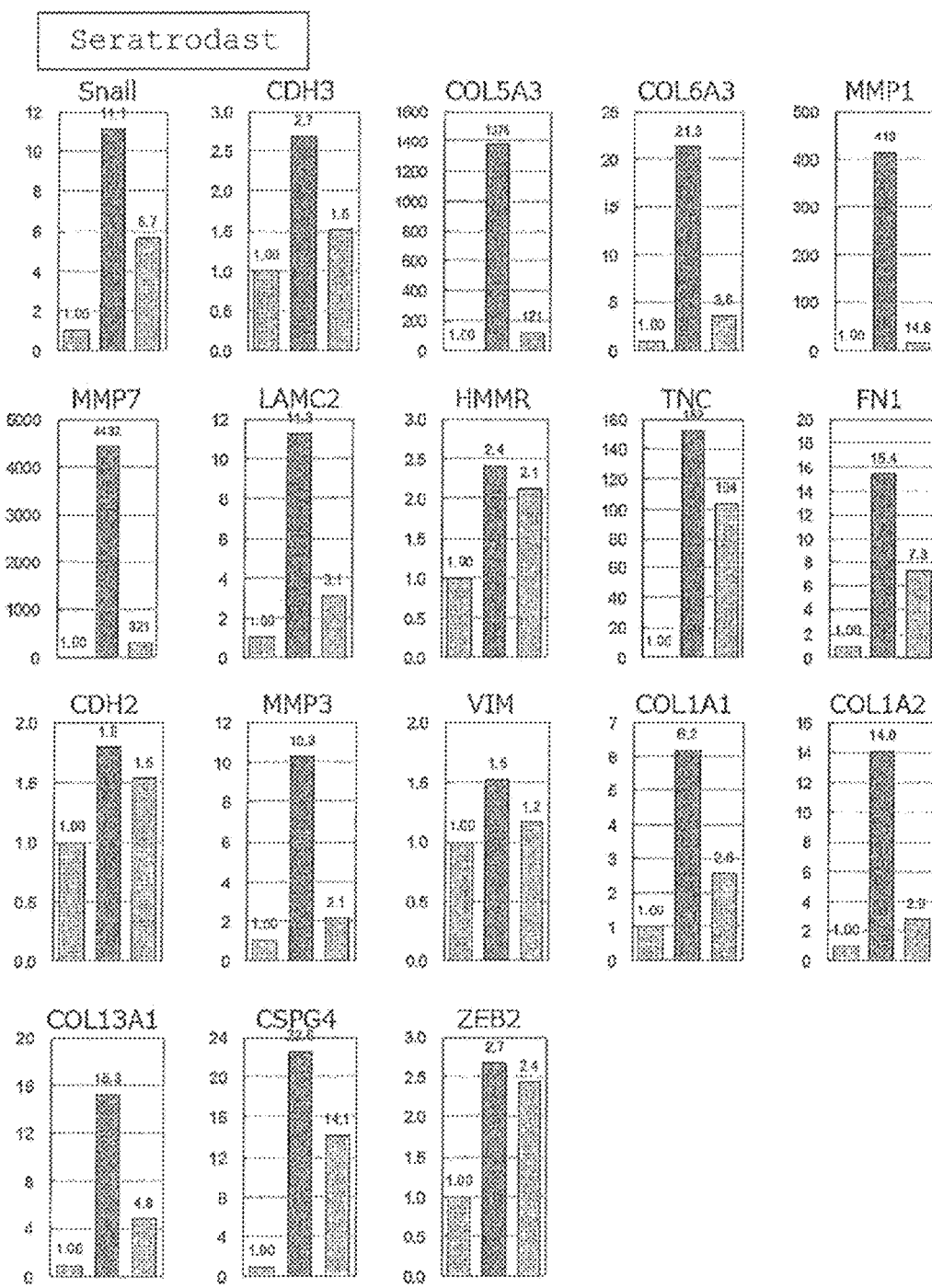
FIG. 12 includes graphs showing that seratrodast suppresses EMT in RPE cells.

The first stage in FIG. 12 (seratrodast) shows Snail, CDH3, COL5A3, COL6A3, and MMP1 from the left, the second stage shows MMP7, LAMC2, HMMR, TNC, and FN1 from the left, the third stage shows CDH2, MMP3, VIM, COL1A1, and COL1A2 from the left, and the fourth stage shows COL13A1, CSPG4, and ZEB2 from the left.

As shown in FIG. 8 to FIG. 12, also the five compounds (flufenamic acid aluminum, mefenamic acid, sulindac, tiaprofenic acid, seratrodast) were demonstrated to significantly suppress expression of EMT markers at the time of EMT induction. It is considered that these compounds suppress production of VEGF and the like involved in development or extension of CNV by significantly suppressing EMT, and can prevent and/or treat CNV radically.

Test Example 2-3

Change in Expression of VEGF 1

Three compounds (oxaprozin, epalrestat, zaltoprofen) were assessed for the VEGF suppressive effect using the cell model as described above.

RPE cells (ARPE-19) were seeded on a plate, and incubated for 5 days at 37° C. For the RPE cells, EMT was induced in the conditions described in Test example 1-1, and oxaprozin (Cmax: 340.9 µM), epalrestat (Cmax: 12.2 µm), or zaltoprofen (Cmax: 20.4 µM) was added simultaneously, and the cells were collected after 48 hours from induction of EMT. Each compound was added in a concentration of Cmax, ½ of Cmax or ¼ of Cmax. As a control, a sample to which a compound to be assessed (test drug) is not added was used. The collected cells were washed with PBS, and 350 µL of an RLT buffer was added to prepare a lysate for RNA extraction. Total RNA was extracted from the lysate using an RNeasy Micro kit (QIAGEN, #74004), and from 2 µg of the obtained RNA, cDNA was prepared using a SuperScript III First-Strand Synthesis SuperMix for qRT-PCR (Invitrogen, #11752-250). Using 50 ng of the obtained cDNA as a template, a real-time PCR (ABI Prism 7500 Sequence Detection System) was conducted according to the manufacturer's protocol, and expression of mRNA of each gene was quantified. Specific primers for respective genes were purchased from Invitrogen. Ct (Threshold Cycle) value of each gene was calculated as a percentage to a non-treated sample after normalization by endogenous control. For each result, a significant test (Student t test) was conducted, and when $p<0.05$, the result was marked with "*", and when $p<0.01$, the result was marked with "**". The results are shown in FIG. 13 to FIG. 15.

Figure 13:
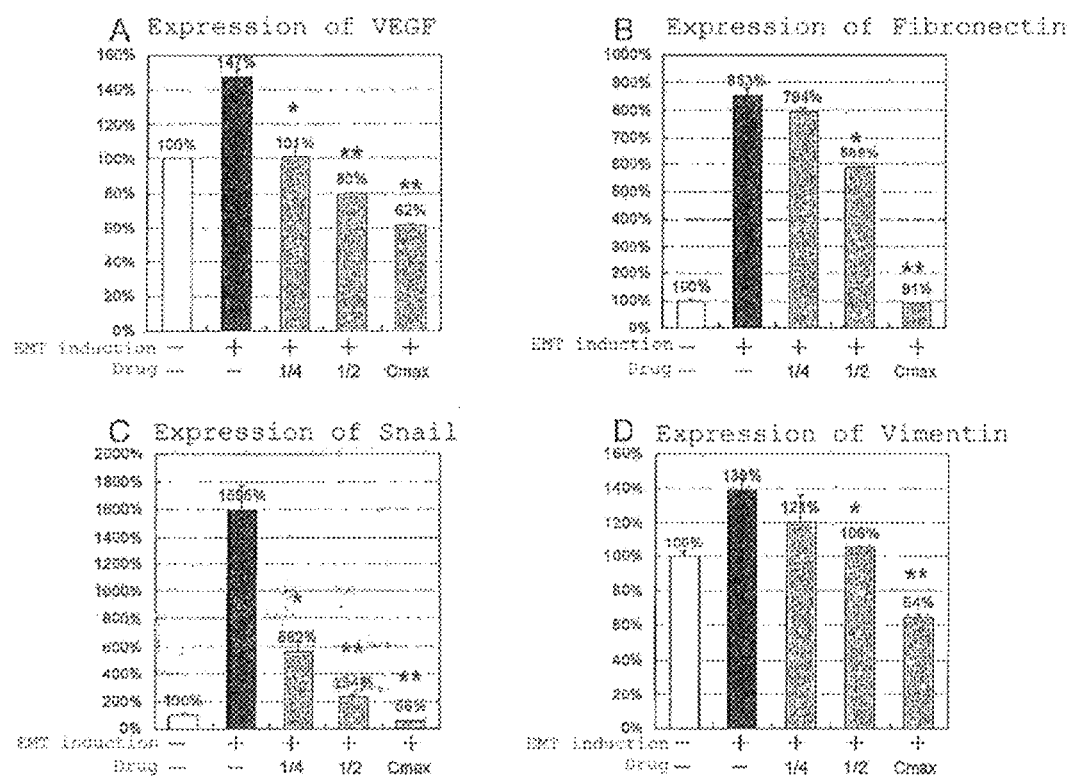
FIG. 13 includes graphs showing the results of verification for influence of oxaprozin on expression amounts of VEGF and EMT markers in RPE cells.

As shown in FIG. 13, in RPE cells, VEGF showed enhanced mRNA expression by induction of EMT. Oxaprozin suppressed enhancement of VEGF expression in a concentration dependent manner. Significant VEGF suppressive effect was observed also in a concentration of ¼ of Cmax (A). Fibronectin, Snail, and vimentin which are mesenchymal markers showed enhanced expression amount by induction of EMT. Oxaprozin suppressed enhancement of expression of these in a concentration dependent manner (B to D, respectively).

Figure 14:
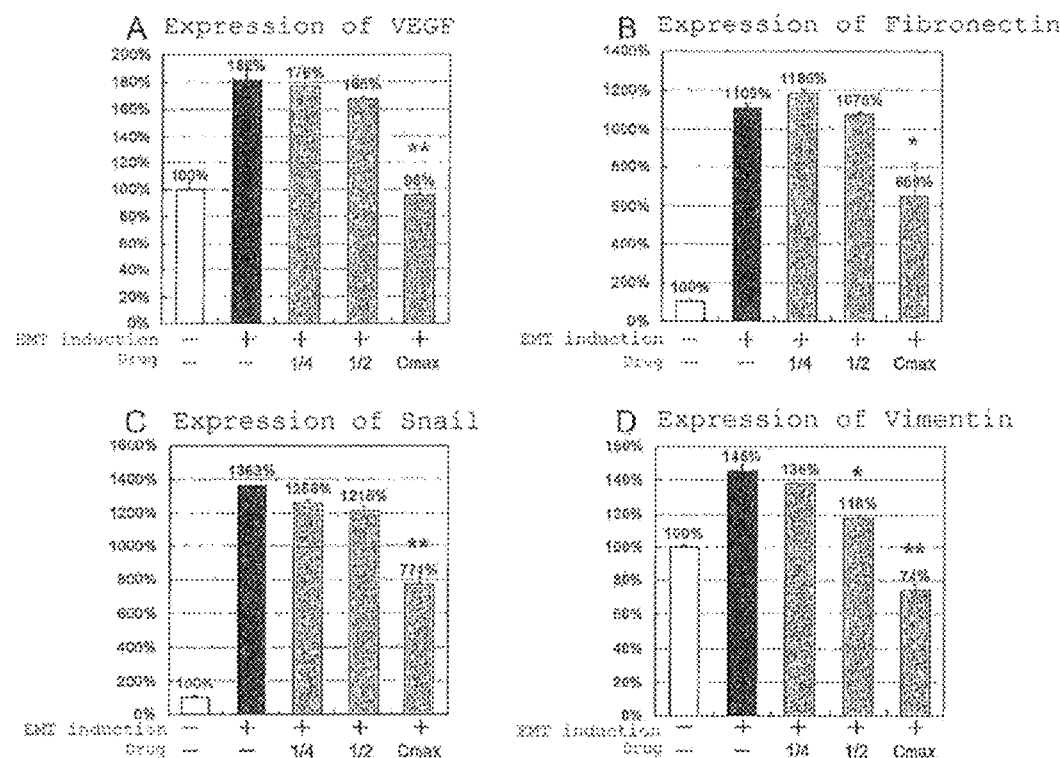
FIG. 14 includes graphs showing the results of verification for influence of epalrestat on expression amounts of VEGF and EMT markers in RPE cells.

As shown in FIG. 14, in RPE cells, VEGF showed enhanced mRNA expression by induction of EMT. Epalrestat suppressed enhancement of VEGF expression in a concentration dependent manner (A). Fibronectin, Snail, and vimentin which are mesenchymal markers showed enhanced expression amount by induction of EMT. Epalrestat suppressed enhancement of expression of these in a concentration dependent manner (B to D, respectively).

Figure 15:
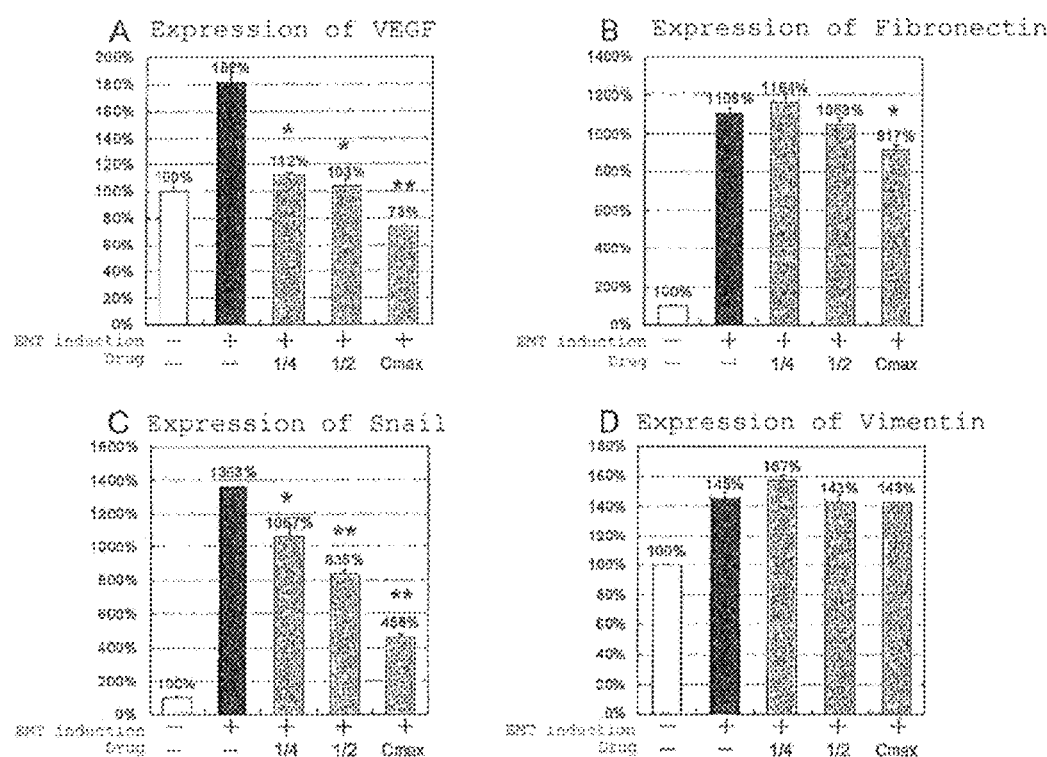
FIG. 15 includes graphs showing the results of verification for influence of zaltoprofen on expression amounts of VEGF and EMT markers in RPE cells.

As shown in FIG. 15, in RPE cells, VEGF showed enhanced mRNA expression by induction of EMT. Zaltoprofen suppressed enhancement of VEGF expression in a concentration dependent manner. Significant VEGF suppressive effect was observed also in a concentration of ¼ of Cmax (A). Fibronectin, Snail, and vimentin which are mesenchymal markers showed enhanced expression amount by induction of EMT. Zaltoprofen suppressed enhancement of expression of these in a concentration dependent manner (B to D, respectively).

FIG. 13 to FIG. 15 revealed that the three compounds (oxaprozin, epalrestat, zaltoprofen) suppress enhancement of mRNA expression of VEGF by significantly suppressing EMT. These compounds are capable of radically preventing and/or treating CNV because these compounds can suppress VEGF showing enhanced expression by EMT. Also, these results infer that zafirlukast and amlexanox capable of significantly suppressing EMT can also suppress VEGF, and are capable of radically preventing and/or treating CNV.

Reference Test Example 2-4

Change in Expression of VEGF 2

Etodolac (Cmax: 42.5 µM) and indomethacin (Cmax: 2.79 µM) which are NSAIDs other than the aforementioned oxaprozin and zaltoprofen were assessed for the VEGF suppressive effect using the cell model as described above in the same manner as in Test example 2-3. The results are shown in FIG. 16 or FIG. 17, respectively.

Figure 16:
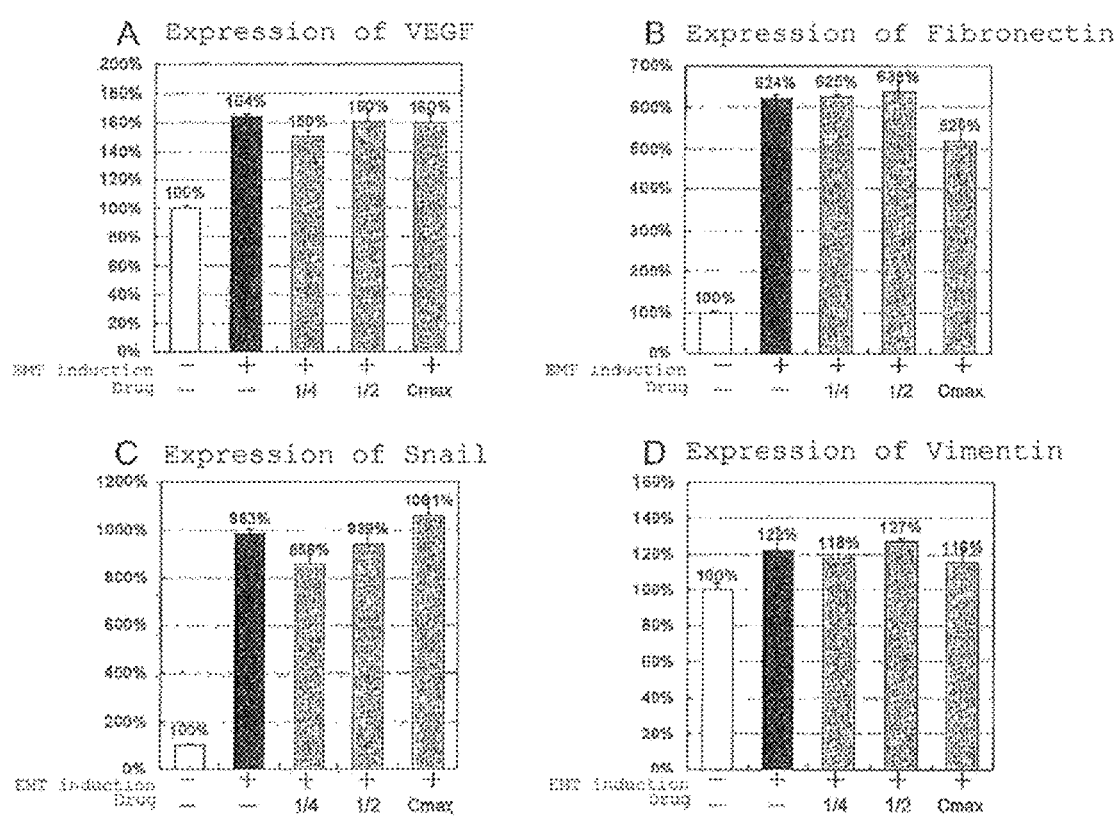
FIG. 16 includes graphs showing the results of verification for influence of etodolac on expression amounts of VEGF and EMT markers in RPE cells.

As shown in FIG. 16, in RPE cells, VEGF showed enhanced mRNA expression by induction of EMT. However, etodolac did not suppress enhancement of VEGF expression (A). Fibronectin, Snail, and vimentin which are mesenchymal markers showed enhanced expression amount by induction of EMT. However, etodolac did not suppress enhancement of expression of these. No significant difference was observed among all the conditions (respectively, B to D).

Figure 17:
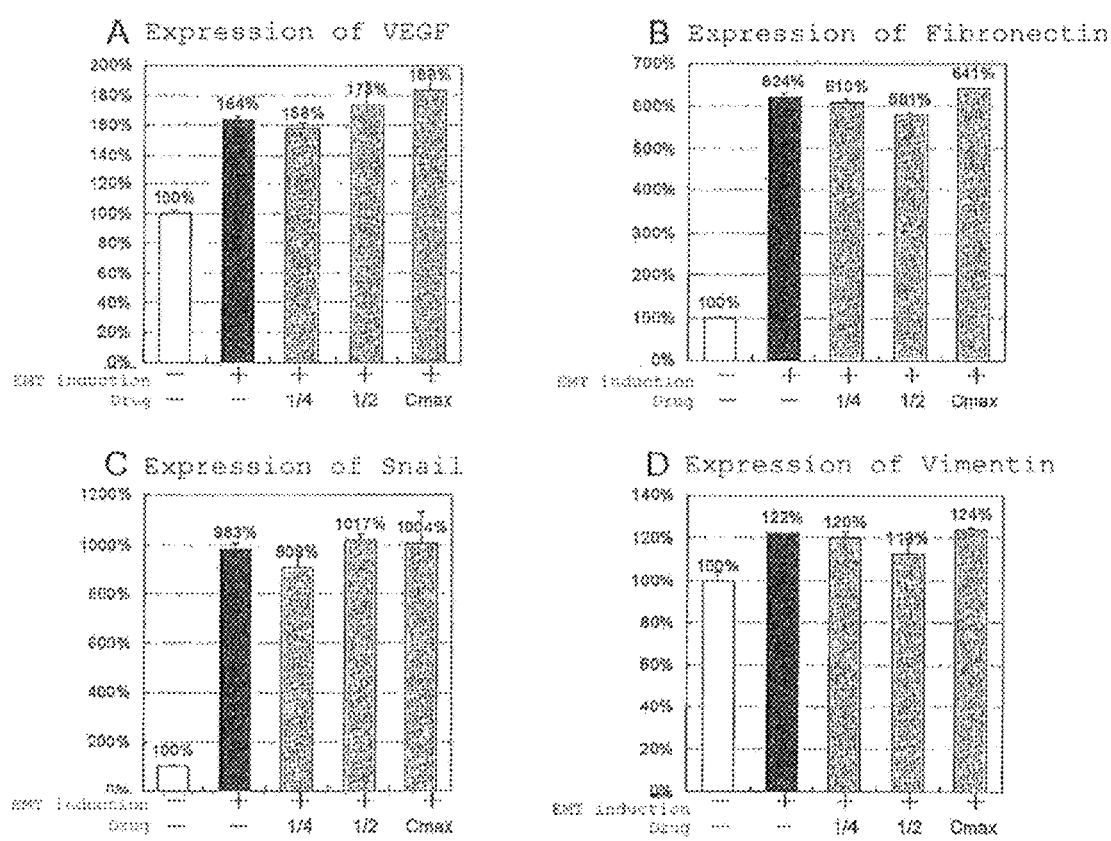
FIG. 17 includes graphs showing the results of verification for influence of indomethacin on expression amounts of VEGF and EMT markers in RPE cells.

As shown in FIG. 17, in RPE cells, VEGF showed enhanced mRNA expression by induction of EMT. However, indomethacin did not suppress enhancement of VEGF expression (A). Fibronectin, Snail, and vimentin which are mesenchymal markers showed enhanced expression amount by induction of EMT. However, indomethacin did not suppress enhancement of expression of these. No significant difference was observed among all the conditions (respectively, B to D).

It was inferred from the results of etodolac and indomethacin that the compounds incapable of suppressing EMT in RPE cells are not effective for prophylaxis and/or therapy of CNV because they are also incapable of suppressing enhancement of VEGF expression.

Test Example 2-5

Change in Expression of VEGF 3

Three compounds (flufenamic acid aluminum (Cmax: 27.91 µM), mefenamic acid (Cmax: 38.54 µM), seratrodast (Cmax: 31.03 µM)) were assessed for the VEGF suppressive effect using the cell model as described above. The VEGF suppressive effect was assessed using the cell model as described above in the same manner as in Test example 2-3. The results are shown in FIG. 18 to FIG. 20, respectively.

Figure 18:
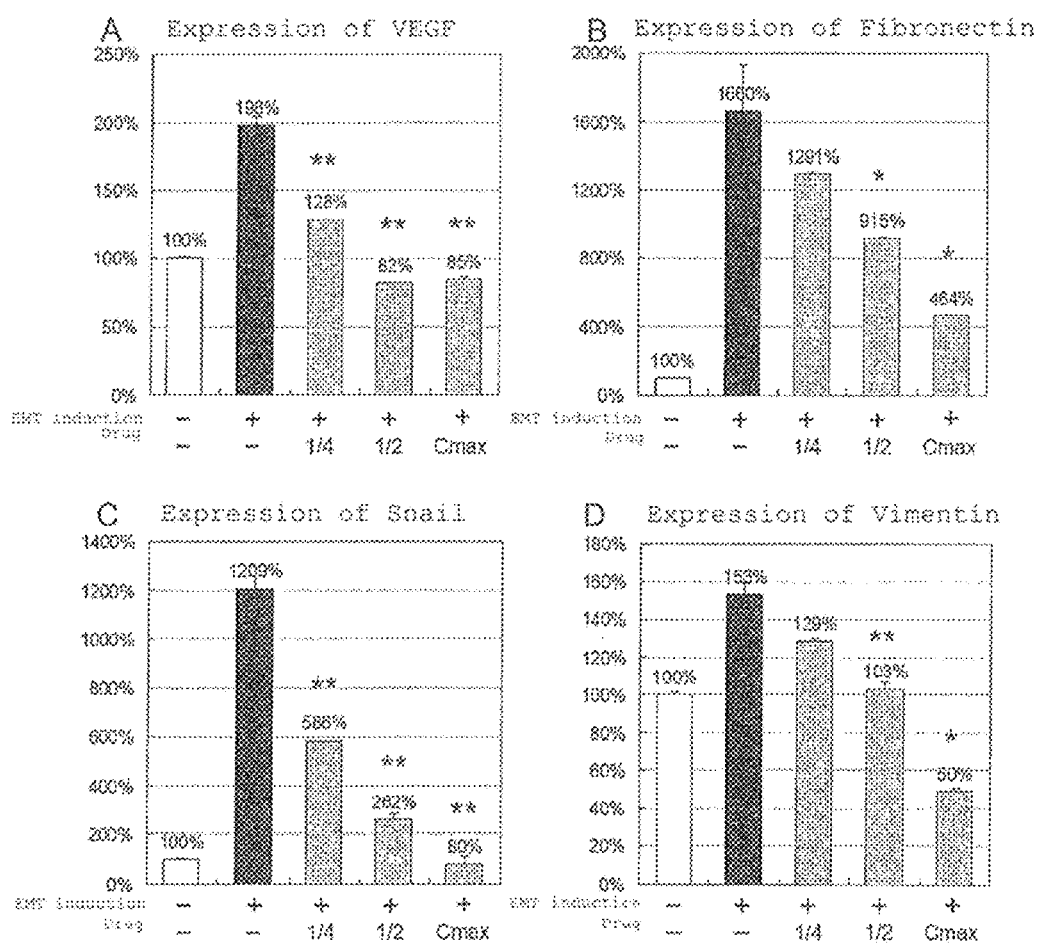
FIG. 18 includes graphs showing the results of verification for influence of flufenamic acid aluminum on expression amounts of VEGF and EMT markers in RPE cells.

As shown in FIG. 18, in RPE cells, VEGF showed enhanced mRNA expression by induction of EMT. Flufenamic acid aluminum suppressed enhancement of VEGF expression in a concentration dependent manner. Significant VEGF suppressive effect was observed also in a concentration of ¼ of Cmax (A). Fibronectin, Snail, and vimentin which are mesenchymal markers showed enhanced expression amount by induction of EMT. Flufenamic acid aluminum suppressed enhancement of expression of these in a concentration dependent manner (B to D, respectively).

Figure 19:
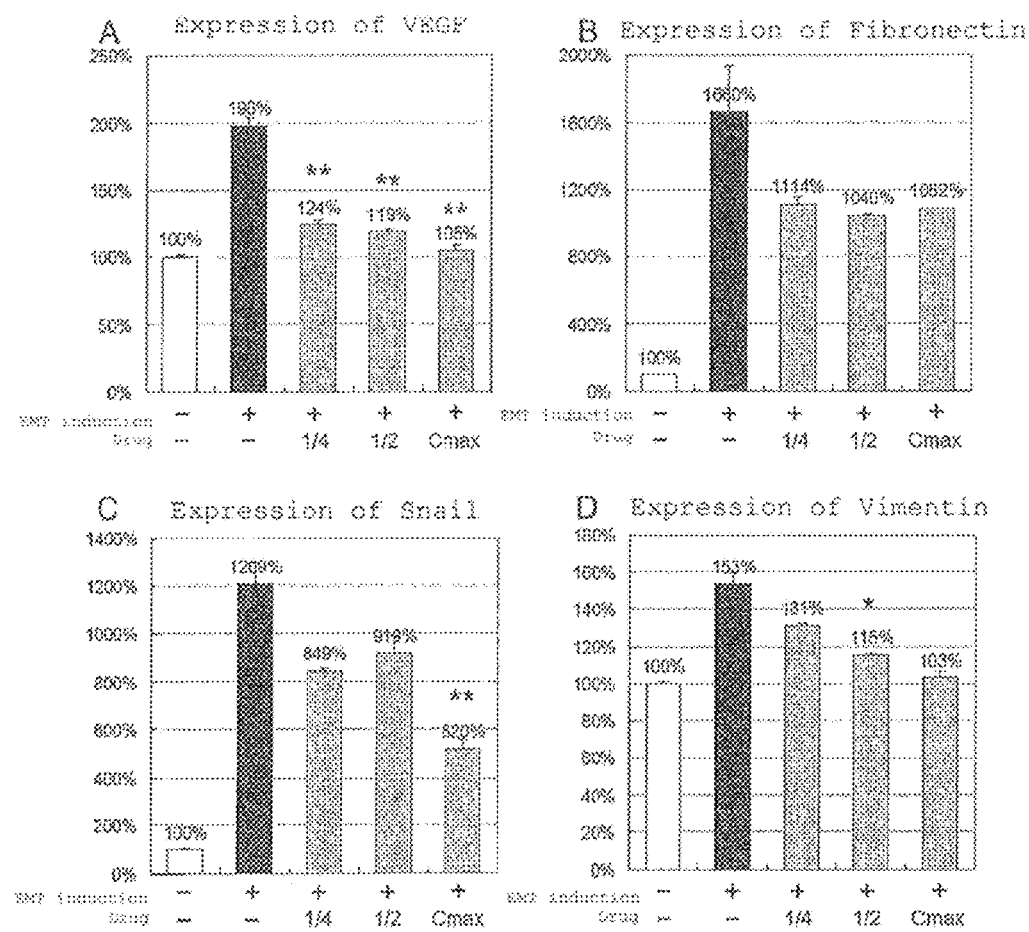
FIG. 19 includes graphs showing the results of verification for influence of mefenamic acid on expression amounts of VEGF and EMT markers in RPE cells.

As shown in FIG. 19, in RPE cells, VEGF showed enhanced mRNA expression by induction of EMT. Mefenamic acid suppressed enhancement of VEGF expression in a concentration dependent manner. Significant VEGF suppressive effect was observed also in a concentration of ¼ of Cmax (A). Fibronectin, Snail, and vimentin which are mesenchymal markers showed enhanced expression amount by induction of EMT. Mefenamic acid suppressed enhancement of expression of these in a concentration dependent manner (B to D, respectively).

Figure 20:
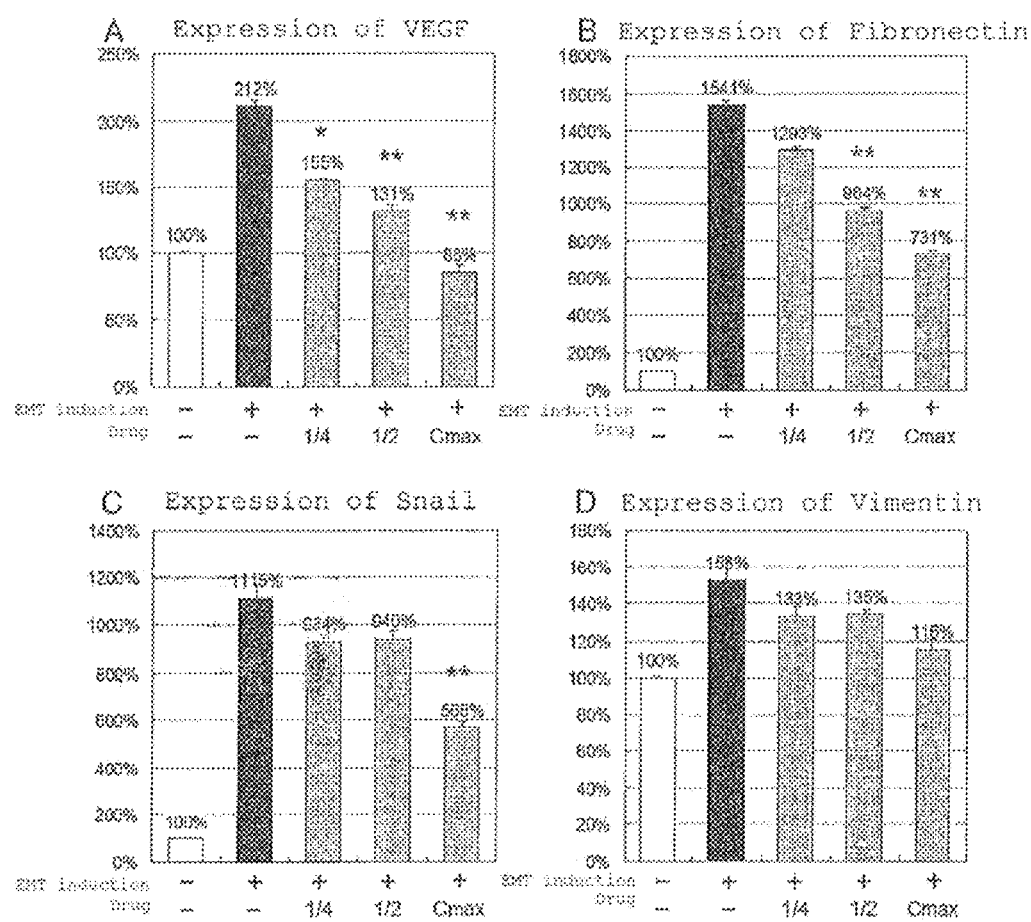
FIG. 20 includes graphs showing the results of verification for influence of seratrodast on expression amounts of VEGF and EMT markers in RPE cells.

As shown in FIG. 20, in RPE cells, VEGF showed enhanced mRNA expression by induction of EMT. Seratrodast suppressed enhancement of VEGF expression in a concentration dependent manner. Significant VEGF suppressive effect was observed also in a concentration of ¼ of Cmax (A). Fibronectin, Snail, and vimentin which are mesenchymal markers showed enhanced expression amount by induction of EMT. Seratrodast suppressed enhancement of expression of these in a concentration dependent manner (B to D, respectively).

FIG. 18 to FIG. 20 revealed that the three compounds (flufenamic acid aluminum, mefenamic acid, seratrodast) suppress enhancement of mRNA expression of VEGF by significantly suppressing EMT. It is inferred that these compounds are capable of radically preventing and/or treating CNV because these compounds can suppress VEGF showing enhanced expression by EMT. These compounds are capable of radically preventing and/or treating CNV because these compounds can suppress VEGF showing enhanced expression by EMT. Also, these results infer that zafirlukast and amlexanox capable of significantly suppressing EMT can also suppress VEGF, and are capable of radically preventing and/or treating CNV.

Test Example 3

In Vivo Model Test for Assessing CNV Suppression

It is known that laser irradiation of a mouse ocular fundus induces choroidal angiogenesis and EMT (Reference document: Ishikawa, et al, Exp Eye Res. 2016 January; 142: 19.25). So, zaltoprofen was assessed for the suppressive effect of CNV and EMT by using a mouse laser irradiation model.

A zaltoprofen suspension was prepared by stirring 0.15 g of zaltoprofen (available from TOKYO CHEMICAL INDUSTRY CO., LTD.) and 0.75 g of gum arabic (available from Wako Pure Chemical Industries, Ltd.) in 60 mL of water. A medium (Vehicle) was prepared by dissolving and stirring 0.75 g of gum arabic in 60 mL of water.

Then, an ocular fundus of a C57BL/6J mouse (8-week old, N=13) was laser-irradiated at four points for each eye under a slit lump using a multi-color laser light coagulator. From directly after irradiation, a vehicle or a zaltoprofen solution (25 mg/kg) was orally administered once a day for three weeks, and the following assessments were conducted. For (1) and (3), the same individual was used.

(1) CNV assessment (N=3)
(2) EMT assessment: Collagen Type 1 (N=10)
(3) EMT assessment: Vimentin (N=3)

Test Example 3-1

Effect of Suppressing Choroidal Angiogenesis (CNV) by Laser Irradiation by Zaltoprofen After two weeks from laser irradiation, Fluorescite Injection 500 mg (Alcon Japan Ltd.) was administered (1 mL/kg) from the caudal vein, after about 1 minute from the administration, and a fluorescent fundus photograph was taken. Four points for each eye from the taken fluorescent fundus photograph were scored on the basis of the following assessment criteria. The results are shown in FIG. 21, and the representative images are shown in FIG. 22.

[Assessment Criteria]

| | |
|---|---|
| No fluorescence | 0 |
| Slight fluorescence observed | 1 |
| Moderate fluorescence observed | 2 |
| Intense fluorescence observed | 3 |

Figure 21:
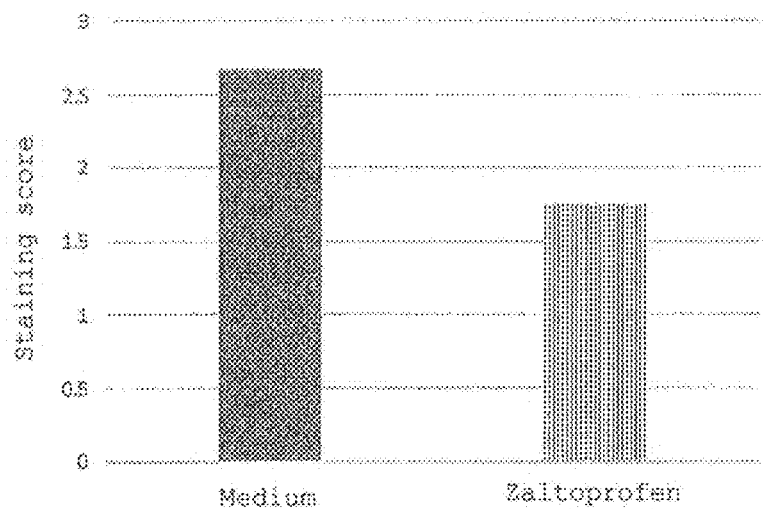
FIG. 21 is a graph showing the result of CNV suppressive effect of zaltoprofen, verified by a laser-induced fibrosis test.
Figure 22:
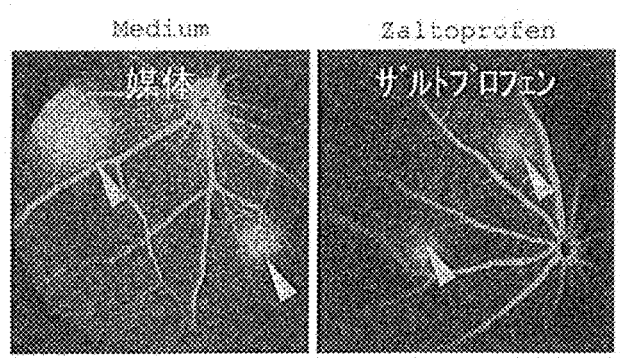
FIG. 22 includes fluorescent fundus photographs showing the result of CNV suppressive effect of zaltoprofen, verified by a laser-induced fibrosis test.

As shown in FIG. 21, the CNV score by laser irradiation was significantly lower in the zaltoprofen administration group than in the Vehicle administration group.

In FIG. 22, Arrow Head is a part in which fluorescence leaks by CNV. As shown in FIG. 22, the CNV by laser irradiation was significantly suppressed in the zaltoprofen administration group (right photograph), compared with the Vehicle administration group (left photograph).

Test Example 3-2

Effect of Suppressing EMT by Laser Irradiation (EMT Assessment: Collagen Type 1) by Zaltoprofen After three weeks from laser irradiation, mice were euthanatized by cervical dislocation, and eyeballs were extracted, and dipped and fixed in 4% paraformaldehyde phosphate buffer (Wako Pure Chemical Industries, Ltd.). Cornea, crystalline lens, and retina were removed from each eyeball to give the state of an optic cup, followed by washing three times with PBST. Then dehydration treatment was conducted using 50% methanol and 100% methanol solution, and incubated for 60 minutes in a blocking solution (1% BSA, 0.5% TritonX-100/PBS). Further, after standing still overnight with a primary antibody (anti-collagen antibody, available from Rockland), reaction with a secondary antibody (Alexa488 antibody, available from Life technologies) was allowed for 1 hour, and then a flat-mounted stained specimen was prepared by mounting on a slide glass. The specimen was subjected to photography of a stained image by the anti-Collagen Type 1 antibody under a microscope, and then quantitatively assessed. The results are shown in FIG. 23.

Figure 23:
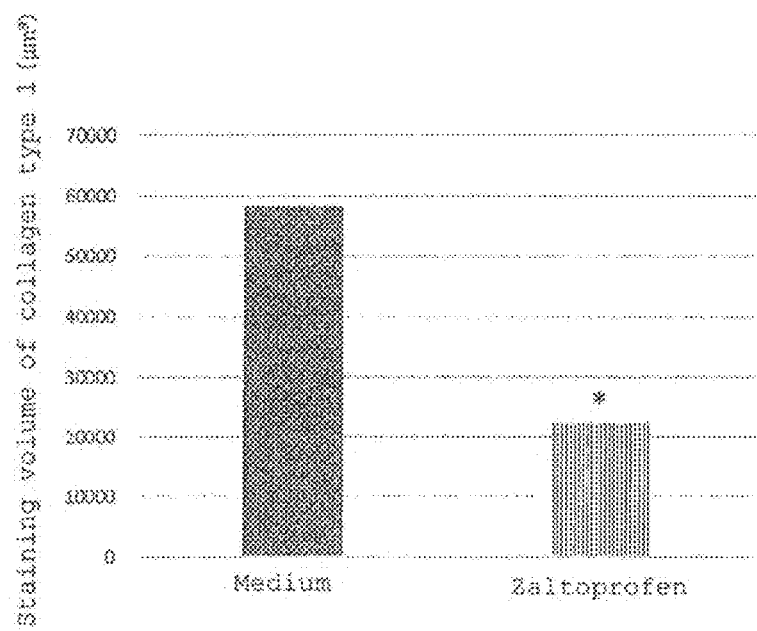
FIG. 23 is a graph showing the result of EMT suppressive effect of zaltoprofen, verified by a laser-induced fibrosis test.

As shown in FIG. 23, it was proved that the stained volume of Collagen Type 1 occurred by laser irradiation significantly decreases in the zaltoprofen administration group, compared with the Vehicle administration group ($p<0.05$). That is, it was revealed that zaltoprofen shows significant suppressive effect for EMT.

Test Example 3-3

Effect of Suppressing EMT by Laser Irradiation (EMT Assessment: Vimentin) by Zaltoprofen After three weeks from laser irradiation, mice were euthanatized by cervical dislocation, and eyeballs were extracted, and dipped and fixed in 4% paraformaldehyde phosphate buffer (available from Wako Pure Chemical Industries, Ltd.). Each of the fixed eyeballs was dipped in 10% sucrose (available from Wako Pure Chemical Industries, Ltd.) and 25% sucrose, for 3 hours, respectively, and then an optic cup was prepared. A frozen section was prepared, and pasted on a slide glass. Microscopic observation was carried out to select those in which the laser irradiation point can be seen were selected. Then a slide glass on which a section was pasted was put into a HistoVT One (available from NAC-ALAI TESQUE, INC.) that was 10-fold diluted with water, and dipped for 15 minutes at 70° C. TrueBlack (available from Biotium) that was 20-fold diluted with 70% ethanol (available from Wako Pure Chemical Industries, Ltd.) was dropped on a section and stood still for several minutes at temperature, and then 5% goat serum (available from DAKO JAPAN CO., LTD.) was dropped on the section, and stood still for 30 minutes at room temperature. Then a primary antibody (Anti-Vimentin antibody, available from abcam) added with Can Get Signal (R) Immunostain Solution B (available from TOYOBO CO., LTD.) was added to the section, and the section was stood still overnight. Further, a secondary antibody (Alexa Fluor546, available from Thermo Fisher Scientific Inc.) and Hoechst 33342 (available from DOJINDO LABORATORIES) added with Can Get Signal (R) Immunostain Solution B were added to the section, and the section was stood still for 30 minutes. Observation and photographing were conducted by a fluorescent microscope in the following conditions.

Vimentin: excitation wavelength 520-550 nm, detection wavelength 580 nm

Nucleus: excitation wavelength 330-385 nm, detection wavelength 420 nm

Figure 24:
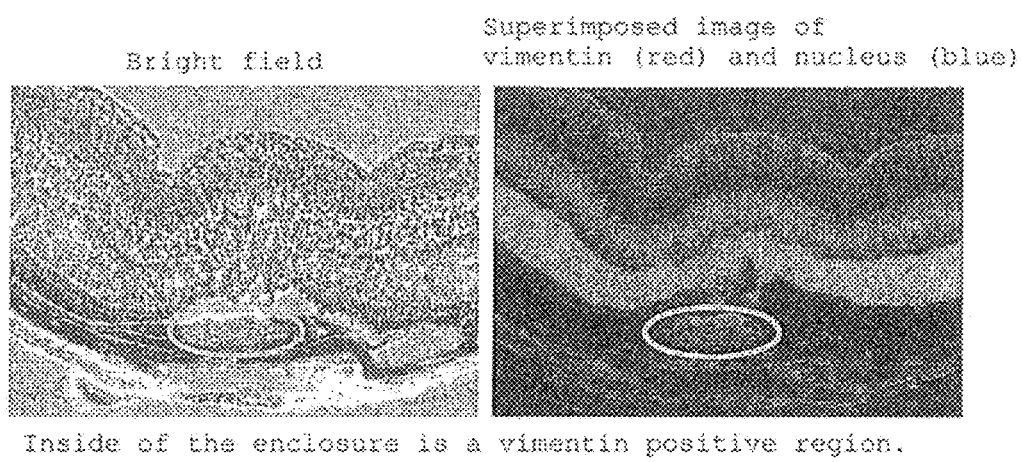
FIG. 24 incudes fluorescent microphotographs showing the result of EMT suppressive effect of zaltoprofen, verified by a laser-induced fibrosis test.
Figure 25:
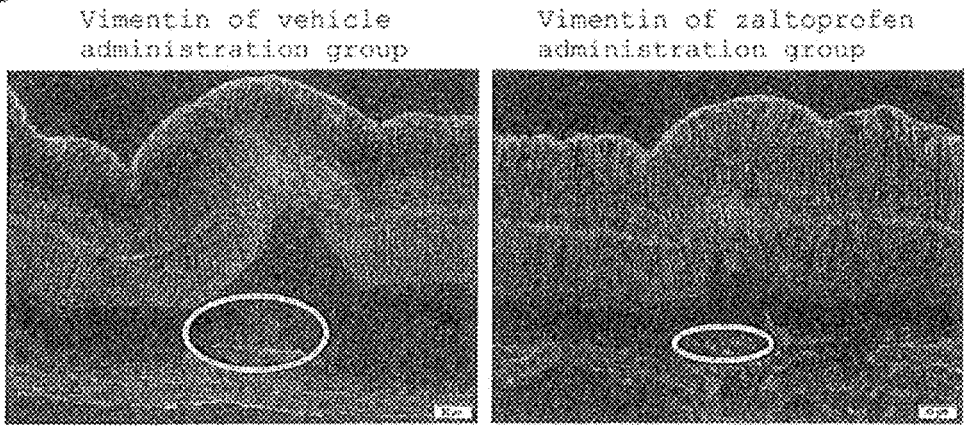
FIG. 25 includes fluorescent microphotographs showing the result of EMT suppressive effect of zaltoprofen, verified by a laser-induced fibrosis test.

The results of photographing are shown in FIG. 24 and FIG. 25. FIG. 24 shows the Vehicle administration group. In FIG. 24, the left photograph shows a bright field image, and the right photograph is a superimposed image of Vimentin (red) and nucleus (blue). In FIG. 25, the left photograph shows Vimentin of the Vehicle administration group, and the right photograph shows Vimentin of the zaltoprofen administration group. In FIG. 24 and FIG. 25, the inside of the enclosure indicates a Vimentin positive region by laser irradiation.

As shown in FIG. 24, a part with less pigment appeared near RPE in the laser irradiation site (left photograph). and staining of Vimentin which is a mesenchymal marker was observed (right photograph). This infers that RPE express Vimentin by laser irradiation, and cause epithelial-mesenchymal transition (EMT). Further, as shown in FIG. 25, RPE in the Vehicle administration group were Vimentin positive (left photograph). On the other hand, in the zaltoprofen administration group, the Vimentin positive area was reduced in comparison with the Vehicle administration group (right photograph).

These revealed that zaltoprofen suppresses EMT in the laser irradiation model. That is, it is considered that zaltoprofen suppresses drusen formation through EMT suppression of RPE. It is also inferred that prophylaxis and/or therapy of CNV can be achieved by any other compounds than zaltoprofen capable of significantly suppressing EMT.

4

Demonstration of EMT in Human Specimen

Test Example 4-1

Morphologic Observation of AMD Patient Drusen

A human healthy subject control (Control) sample and a sample of retinal pigment epithelial cells (RPE cells) of AMD patient were obtained from the National Disease Research Interchange. These tissue samples were deparaffinized by treating three times with xylene for 5 minutes each, twice with 100% ethanol for 1 minute each, with 90% ethanol for 1 minute, with 80% ethanol for 1 minute, with 70% ethanol for 1 minute, and with water for 5 minutes. Staining was conducted with a Mayer's hematoxylin solution for 4 minutes, and with an eosin liquid for 1 minute. After treating for 5 minutes in flowing water, treatments were conducted with 70% ethanol for 1 minute, with 80% ethanol for 1 minute, with 90% ethanol for 1 minute, twice with 100% ethanol for 1 minute each, and three times with xylene for 5 minutes each, followed by mounting with Marinol. After drying for 15 minutes or more at room temperature, the RPE cells of the healthy subject, and the RPE cells of AMD patient were observed. The results of staining by hematoxylin/eosin staining are shown in FIG. 26.

Figure 26:
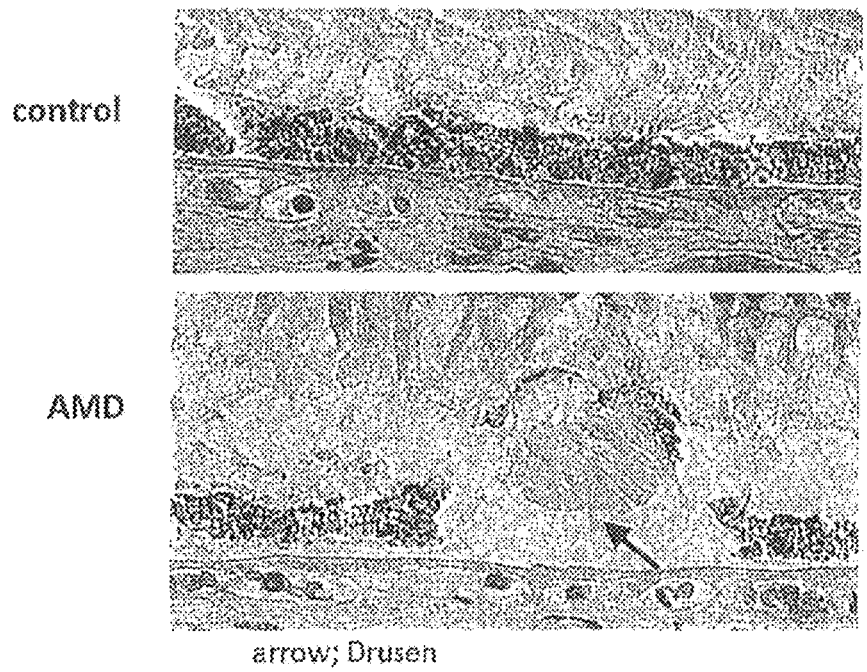
FIG. 26 includes a stained photograph showing the shapes of RPE cells in AMD patient drusen, compared with a stained photograph showing the shapes of RPE cell in a healthy subject.

By reviewing the observation results of FIG. 26 in detail, the present inventors found that in the macula of a healthy subject control, RPE cells have a cubic shape, and regularly align in a single layer by intracellular adhesion, whereas in the macula of an AMD patient where drusen are exist, the shape of the RPE cells changes into a spindle shape, and the RPE cells acquire mobility, and the cells are piled up. From these observation results, the present inventors made a hypothesis that in the macula of an AMD patient, intracellular adhesion of RPE cells is weakened, and the morphologic change occurs, and thus EMT (Epithelial-mesenchymal transition) which is a phenomenon that the epithelial property disappears in the RPE cells. In the following Test examples 4-2 to 4-4, tests for proving occurrence of EMT in RPE cells were conducted on the basis of this hypothesis.

Test Example 4-2

Disappearance of Epithelial Marker in AMD Patient Drusen

Disappearance of the epithelial marker in human healthy subject control (Control) samples and in AMD patient retinal pigment epithelial cell (RPE cell) samples were verified immunohistochemically (IHC). After incubation for 30 minutes in a gas-phase incubator at 56° C., the tissue sample was deparaffinized by treating three times with xylene for 5 minutes each, twice with 100% ethanol for 1 minute each, with 90% ethanol for 1 minute, with 80% ethanol for 1 minute, with 70% ethanol for 1 minute, and with water for 5 minutes. After removing a melanin pigment in tissues using Delicate Melanin Bleach Kit for Special Stains and IHC (Polysciences, #24909-1) according to the manufacturer's protocol, a microwave treatment using a citrate buffer pH 6.0 was conducted for 10 minutes to activate the antigen. After standing still for 30 minutes at room temperature, treatments were conducted with PBS for 5 minutes, with a 3% hydrogen peroxide/PBS solution for 5 minutes, and with PBS for 5 minutes to inactivate an endogenous peroxidase. The sample was stood still in a 3% BSA/PBS solution for 30 minutes at room temperature to block the tissues. As primary antibodies, an anti-E-Cadherin antibody (BD Biosciences, #610181) that was 500-fold diluted with a 1.5% BSA/PBS solution, and an anti-Cytokeratin 18 antibody (Cell signaling Technology, #4548) that was 1000-fold diluted were added in an amount of 200 μL per one tissue, and caused to react with the tissues for 17 hours at 4° C. The tissues reacted with the primary antibodies were washed three times with PBS for 5 minutes each, and then caused to react with a secondary antibody for 30 minutes at room temperature using a Mouse on Mouse (M.O.M.) Elite Peroxidase Kit (Vector Laboratories, # PK- 2200), and washed three times with PBS for 5 minutes each, and then subjected to an ABC reaction for 30 minutes at room temperature according to the manufacturer's protocol. After washing the tissues three times with PBS for 5 minutes each, color development was caused for 3 minutes at room temperature using an ImmPACT DAB Peroxidase (HRP) Substrate (Vector Laboratories, # SK-4105). The color-developed tissues were stained by using a New hematoxylin Type M (MUTO PURE CHEMICALS CO., LTD., # 30141), and then stood still in flowing water for 3 minutes, and treated with 70% ethanol for 1 minute, with 80% ethanol for 1 minute, with 90% ethanol for 1 minute, twice with 100% ethanol for 1 minute each, and three times with xylene for 5 minutes each, and mounted with the use of Marinol. After drying for 15 minutes or more at room temperature, the RPE cells of the healthy subject, and the RPE cells of AMD patient were observed. The results are shown in FIG. 27.

Figure 27:
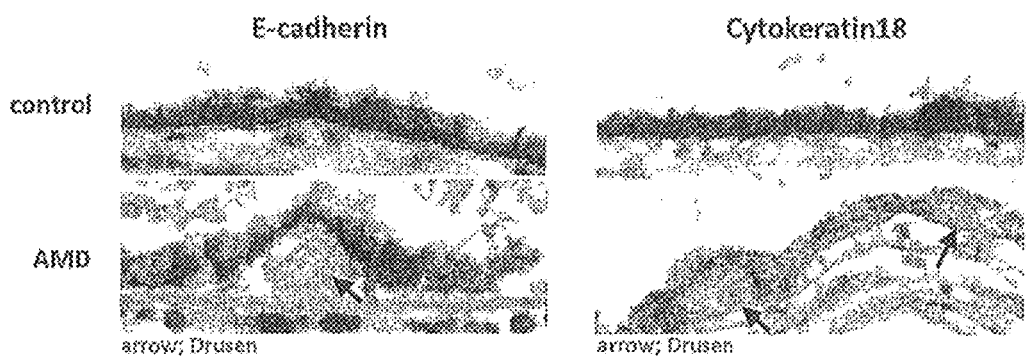
FIG. 27 includes an immunostained photograph indicating the stainability of an epithelial marker in RPE cells in AMD patient drusen, compared with an immunostained photograph indicating the stainability of an epithelial marker in RPE cells in a healthy subject.

As shown in FIG. 27, in a healthy subject control (Control), staining of E-cadherin which is an epithelial marker (E-Cadherin) was observed in an intracellular adhesion site, whereas in the vicinity of AMD patient drusen, staining of E-Cadherin was not observed between cells (the left staining photograph). Also, in the healthy subject control, intense staining of cytokeratin 18 which is an epithelial marker (Cytokeratin 18) was observed in the entire RPE cells, whereas in the vicinity of AMD patient drusen, the signal was reduced comparatively (right staining photograph).

These confirmed that in RPE cells of AMD patients, the epithelial character is lost or decreased.

Test Example 4-3

Enhancement of Mesenchymal Marker in AMD Patient Drusen

Enhancement of the mesenchymal marker in human healthy subject control (Control) samples and in AMD patient retinal pigment epithelial cell (RPE cell) samples were verified immunohistochemically (IHC). After incubation for 30 minutes in a gas-phase incubator at 56° C., the tissue sample was deparaffinized by treating three times with xylene for 5 minutes each, twice with 100% ethanol for 1 minute each, with 90% ethanol for 1 minute, with 80% ethanol for 1 minute, with 70% ethanol for 1 minute, and with water for 5 minutes. A microwave treatment using a citrate buffer pH 6.0 was conducted for 10 minutes to activate the antigen. After standing still for 30 minutes at room temperature, treatments were conducted with PBS for 5 minutes, with a 3% hydrogen peroxide/PBS solution for 5 minutes, and with PBS for 5 minutes to inactivate an endogenous peroxidase. The sample was stood still with a 3% BSA/PBS solution for 30 minutes at room temperature to block the tissues. As primary antibodies, an anti-Fibronectin antibody (abcam, # 45688) that was 100-fold diluted with a 1.5% BSA/PBS solution, and an anti-Vimentin antibody (Sigma-Aldrich, # 6630) that was 10000-fold diluted were added in an amount of 200 μL per one tissue, and caused to react with the tissues for 17 hours at 4° C. The tissues reacted with the primary antibodies were washed three times with PBS for 5 minutes each, and then caused to react with a secondary antibody for 30 minutes at room temperature using a VECTASTAIN Elite ABC Rabbit IgG Kit (Vector Laboratories, # PK-6101) for the anti-Fibronectin antibody, and a Mouse on Mouse (M.O.M.) Elite Peroxidase Kit (Vector Laboratories, # PK-2200) for the anti-Vimentin antibody. After washing three times with PBS for 5 minutes each, the tissues were subjected to an ABC reaction for 30 minutes at room temperature according to the manufacturer's protocol. After washing the tissues three times with PBS for 5 minutes each, color development was caused for 3 minutes at room temperature using an ImmPACT AMEC Red Peroxidase (HRP) Substrate (Vector Laboratories, # SK-4285), and the tissues were washed with distilled water for 5 minutes. The color-developed tissues were stained by using a New hematoxylin Type M (MUTO PURE CHEMICALS CO., LTD., # 30141), and then stood still in flowing water for 3 minutes, and mounted with the use of a Vecta-Mount AQ Aqueous Mounting Medium (Vector Laboratories, # H-5501). After drying for 15 minutes or more at room temperature, the RPE cells of the healthy subject, and the RPE cells of AMD patient were observed. The results are shown in FIG. 28.

Figure 28:
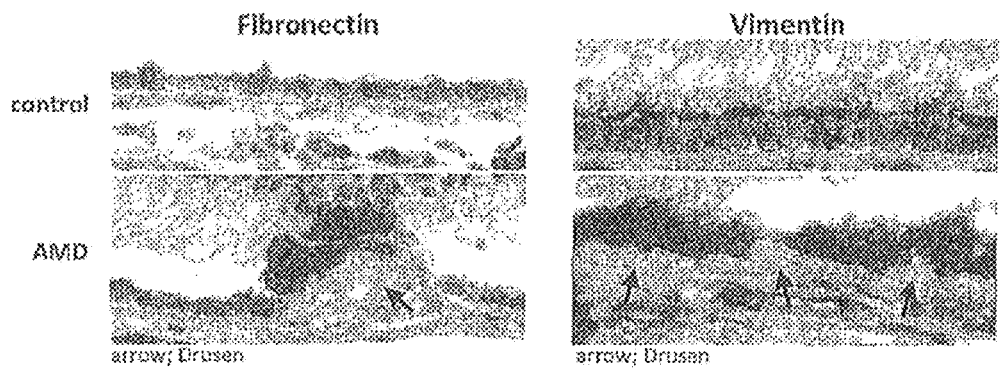
FIG. 28 includes an immunostained photograph indicating the stainability of a mesenchymal marker in RPE cells in AMD patient drusen, compared with an immunostained photograph indicating the stainability of a mesenchymal marker in RPE cells in a healthy subject.

As shown in FIG. 28, in normal RPE cells of the healthy subject control (Control), staining of fibronectin which is a mesenchymal marker was not observed. On the other hand, fibronectin was positive in drusen and RPE cells of AMD patients. Also in RPE cells of the healthy subject control, staining of vimentin which is a mesenchymal marker was not observed. RPE cells of AMD patient drusen were vimentin positive.

These analytical results revealed that in RPE cells of AMD patients, the epithelial character that is seen in the healthy condition is lost or attenuated, and the mesenchymal character is acquired and enhanced in AMD. That is, it was revealed that in AMD, in RPE cells, transition from the epithelial character to the mesenchymal character, epithelial-mesenchymal transition EMT occurs.

Test Example 4-4

Verification in Crab-Eating Monkey Model

From a healthy crab-eating monkey control (Control) sample and a retinal pigment epithelial cell (RPE cell) sample of a AMD crab-eating monkey model, sections were prepared, and disappearance of the epithelial marker and enhancement of the mesenchymal marker were verified immunohistochemically (IHC). The tissue samples were deparaffinized by treating three times with xylene for 5 minutes each, twice with 100% ethanol for 1 minute each, with 90% ethanol for 1 minute, with 80% ethanol for 1 minute, with 70% ethanol for 1 minute, and with distilled water for 10 minutes. A microwave treatment using a citrate buffer pH 6.0 was conducted for 10 minutes to activate the antigen. After standing still for 30 minutes at room temperature, treatments were conducted with PBS for 5 minutes, with a 3% hydrogen peroxide/PBS solution for 5 minutes, and with PBS for 5 minutes to inactivate an endogenous peroxidase. The sample was stood still with a 3% BSA/PBS solution for 20 minutes at room temperature to block the tissues. As primary antibodies, an anti-E-Cadherin antibody (BD Biosciences, # 610181) that was 500-fold diluted with a 1.5% BSA/PBS solution, an anti-Cytokeratin 18 antibody (abcam, # ab668) that was 2000-fold diluted, and an anti-Fibronectin antibody (Epitomics, # 1574-1) that was 600-fold diluted were added in an amount of 200 µL per one tissue, and caused to react with the tissues for 17 hours at 4° C. The tissues reacted with the primary antibodies were washed three times with PBS for 5 minutes each, then caused to react with a secondary antibody for 30 minutes at room temperature using a VECTASTAIN Elite ABC Mouse IgG Kit (Vector Laboratories, # PK-6102) for the anti-E-Cadherin antibody and the anti-Cytokeratin 18 antibody, and using a VECTASTAIN Elite ABC Rabbit IgG Kit (Vector Laboratories, # PK-6101) for the anti-Fibronectin antibody, then washed three times with PBS for 5 minutes each, and then subjected to an ABC reaction for 30 minutes at room temperature according to the attached protocol. After washing the tissues three times with PBS for 5 minutes each, color development was caused for 3 minutes at room temperature using an ImmPACT DAB Peroxidase (HRP) Substrate (Vector Laboratories, # SK-4105) for the anti-E-Cadherin antibody, and using a TMB Peroxidase Substrate Kit (Vector Laboratories, # SK-4400) for the anti-Cytokeratin 18 antibody and the anti-Fibronectin antibody, and the tissues were washed with distilled water for 5 minutes. The color-developed tissues were stained by using a New hematoxylin Type M (MUTO PURE CHEMICALS CO., LTD., # 30141) for the anti-E-Cadherin antibody, and using a VECTOR Nuclear Fast Red (Vector Laboratories, # H-3403) for the anti-Cytokeratin 18 antibody and the anti-Fibronectin antibody. After standing still for 10 minutes in flowing water, treatments were conducted with 70% ethanol for 1 minute, with 80% ethanol for 1 minute, with 90% ethanol for 1 minute, twice with 100% ethanol for 1 minute each, and three times with xylene for 5 minutes each, followed by mounting with Marinol. After drying for 15 minutes or more at room temperature, RPE cells of the crab-eating monkey control and RPE cells of the AMD crab-eating monkey model were observed. The results are shown in FIG. 29.

The macula exists only in higher primates among other primates, and macular degeneration also exists in specific primates. For verifying the clinical state of macular degeneration, the clinical state in a crab-eating monkey which is recognized as a model animal for macular degeneration was analyzed.

Figure 29:
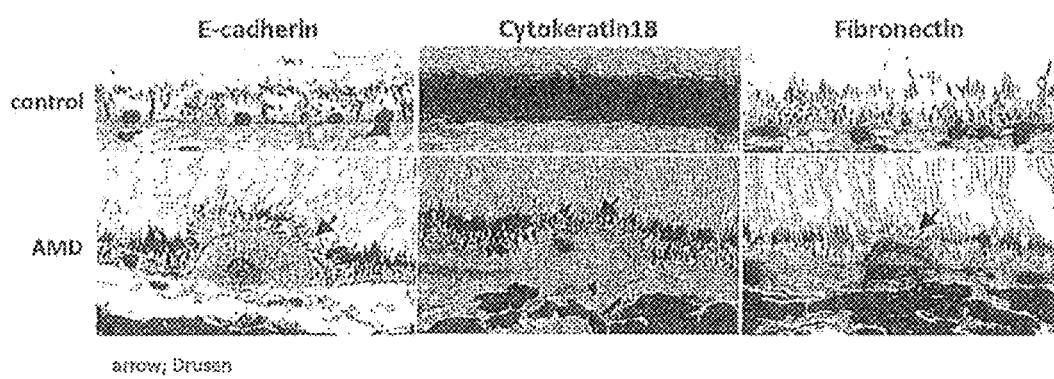
FIG. 29 includes an immunostained photograph indicating the stainability of an epithelial marker and a mesenchymal marker in RPE cells in an AMD model animal, compared with an immunostained photograph indicating the stainability of an epithelial marker and a mesenchymal marker in RPE cells in a healthy model animal.

As shown in FIG. 29, regarding the shape of RPE cells, it was confirmed that in the healthy crab-eating monkey control (Control), RPE cells have a cubic shape, and regularly align in a single layer by intracellular adhesion. On the other hand, it was confirmed that in RPE cells of AMD crab-eating monkey, the shape changes into a spindle shape, and the cells are piled up in the vicinity of drusen.

Regarding the epithelial marker, staining of E-Cadherin was observed in an intracellular adhesion site in RPE cells in the macula of the healthy crab-eating monkey control (Control), whereas staining of E-Cadherin was not observed between cells in RPE cells of AMD crab-eating monkey where drusen exist. Also, intense staining of Cytokeratin 18 was observed in the entire RPE cells in the healthy crab-eating monkey control, whereas the signal was reduced in drusen of AMD crab-eating monkey, as compared with Control.

Regarding the mesenchymal marker, accumulation in RPE cells and drusen was confirmed in drusen of AMD crab-eating monkey, as evidenced by staining of Fibronectin.

The results in the above Test examples confirmed that EMT occurs in RPE cells of drusen. Therefore, the present inventors inferred that the capability of suppressing EMT in RPE cells leads to suppression of formation of drusen. In the following Test example 5-1, a cell model capable of inducing EMT in RPE cells in vitro was examined for searching for a compound that suppresses EMT in RPE cells or for assessing the influence of a candidate drug on EMT in RPE cells.

5. Construction of EMT Cell Model

Test Example 5-1

Consideration of Induction Condition of EMT in RPE Cells

The present inventors made experiments of testing for stimulation in ten different conditions on RPE cells (retinal pigment epithelial cells strain: ARPE-19, the same applies hereinafter) using a cytokine or a growth factor (TNF-α/IL-1β/TGF-β), and found that significant EMT induction is caused. It is considered that a EMT induction cell model using a cytokine or a growth factor reflects an estimated EMT induction mechanism in an AMD patient.

The ten different conditions are as follows.
(1) TNF-α 100 ng/mL
(2) IL-1β 100 ng/mL
(3) IL-1β 20 ng/mL
(4) TNF-α 500 ng/mL+TGF-β 5 ng/mL
(5) TNF-α 200 ng/mL+TGF-β 5 ng/mL
(6) TNF-α 100 ng/mL+TGF-β 5 ng/mL
(7) TNF-α 100 ng/mL+TGF-β10 ng/mL
(8) TNF-α 100 ng/mL+TGF-β 25 ng/mL
(9) IL-1β 100 ng/mL+TGF-β5 ng/mL
(10) IL-1β 20 ng/mL+TGF-β 5 ng/mL Test Example 5-2

Verification of EMT by Change in Expression of EMT Marker Molecule

RNA was extracted from RPE cells after stimulation, and change in expression was verified.

RPE cells (ARPE-19) were seeded on a plate, and incubated for 5 days at 37° C. For the RPE cells, EMT was induced by the conditions described in Test example 5-1, and the cells were collected after 48 hours from the EMT induction. The collected cells were washed with PBS, and 350 μL of an RLT buffer (available from QIAGEN) was added to prepare a lysate for RNA extraction. Total RNA was extracted from the lysate using an RNeasy Micro kit (QIAGEN, # 74004), and from 2 μg of the obtained RNA, cDNA was prepared using a SuperScript III First-Strand Synthesis SuperMix for qRT-PCR (Invitrogen, # 11752-250). Using 50 ng of the obtained cDNA as a template, a real-time PCR (ABI Prism 7500 Sequence Detection System) was conducted according to the manufacturer's protocol, and expression of mRNA of each gene was quantified. Specific primers for respective genes were purchased from Invitrogen. Ct (Threshold Cycle) value of each gene was calculated as a percentage to a non-treated sample after normalization by endogenous control.

The results are shown in FIG. 1.

As shown in FIGS. 1A and B, in the RPE cells after stimulation, expression of E-Cadherin which is an epithelial marker was decreased (FIG. 1A), and expression of N-cadherin which is a mesenchymal marker was enhanced (FIG. 1B). Such cadherin switching is a representative phenomenon of EMT. Also enhancement in a mesenchymal marker represented by fibronectin (FIG. 1C) and a EMT-related transcription factor group (Snail, Slug, ZEB1) (FIG. 1E to G), and enhancement in expression of ECM represented by type I collagen (COL1A1) were observed (FIG. 1D), and it was confirmed that EMT is induced by stimulation in RPE cells.

Test Example 5-3

Verification of Time-Varying Change in Expression of EMT Marker by Microarray

Formation of a drusen-like structure, and the EMT induction state at a time in the EMT induction time were analyzed.

RPE cells (ARPE-19) were seeded on a plate, and incubated for 5 days at 37° C. For RPE cells, EMT was induced in the conditions as described in Test example 5-1, and cells were collected after 1 hour, after 4 hours, 12 hours, 24 hours, 48 hours and 72 hours from induction of EMT. The collected cells were washed with PBS, and 350 μL of an RLT buffer was added to prepare a lysate for RNA extraction. Total RNA was extracted from the lysate using an RNeasy Micro kit (QIAGEN, # 74004), and fluorescent-labeled with a Low Input QuickAmp Labeling kit (Agilent Technologies, # 5190-2305). The labeled cRNA was hybridized with a Whole Human Genome Oligo-DNA Microarray Kit (Agilent Technologies, # G4112F) according to the protocol prescribed by the manufacturer. The hybridized slide was washed with a Gene Expression Wash Pack (Agilent Technologies, # 5188-5327), and scanned with an Agilent Microarray Scanner (Agilent Technologies, # G2505B). The scanned image was digitized by using a Feature Extraction software version 9.5.1 (available from Agilent Technologies). The numerical data was normalized by a Grobal Normalization method. The results are shown in FIG. 2.

As shown in FIG. 2, the peaks of decrease or increase of the EMT markers occurred variably depending on the particular gene, as observed after 12 hours or 72 hours from induction of EMT, and decreased epithelial markers and enhanced mesenchymal markers and ECMs are as follows.

As epithelial markers decreased by induction of EMT, ID1, ID2, MUC1, Cytokeratin 18 (KRT18), THBS1, VIL2, E-Cadherin (CDH1), and TGFB2 were confirmed.

As the mesenchymal markers and ECMs that were enhanced by induction of EMT, FGF2, TWIST1, VIM, CD44, ZEB1, RDX, MMP9, FN1, TGFB1, RHOA, ZEB2, MMP2, TJP1, CTNNB1, MMP3, ETS1, SNAI1, SNAI2, HAS2, FGF1, SERPINE1, CDH2, MSN, TCF3, SDC1, ITGAV, COL1A1, and SPARC were confirmed.

After 24 hours from EMT induction, a drusen-like structure was formed in the plate seeded with the RPE cells. Decrease in expression of the epithelial marker group represented by E-cadherin and cytokeratin 18, and increase in expression of the mesenchymal marker represented by fibronectin/vimentin and the ECM group were observed, and a clear correlation was observed between formation of a drusen-like structure and the EMT induction state.

Therefore, it was confirmed that formation of the drusen-like structure occurs due to EMT in RPE cells.

Test Example 5-4

Verification of EMT Induction by Enhanced Mobility

Enhancement of mobility of RPE cells by EMT was assessed by using an Invasion Assay method (cell invasion assay) which is a method for assessing the mobility and the invasive ability of cells.

Figure 30:
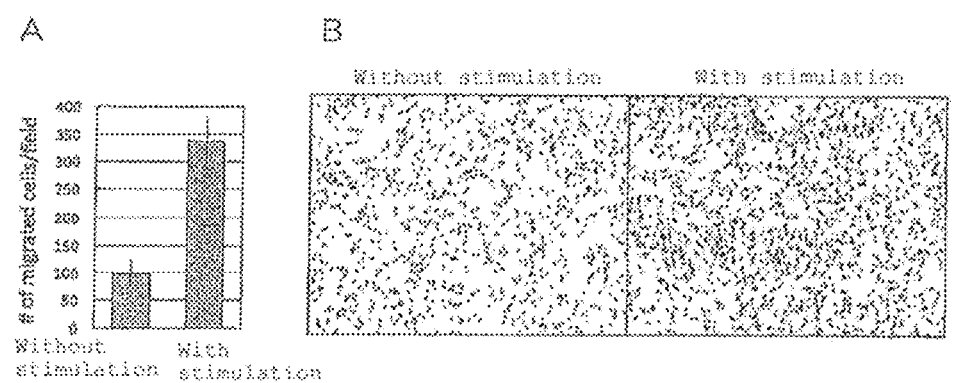
FIG. 30 includes a graph and photographs showing the result of EMT induction in RPE cells, verified by enhancement of the mobility.

RPE cells (ARPE-19) were seeded on a plate, and incubated for 5 days at 37° C. For the RPE cells, EMT was induced by the conditions described in Test example 5-1, and the cells were collected after 24 hours from the EMT induction. The collected cells were seeded in a BD Biocoat Matrigel invasion chamber (BD Bioscience, # 354480), and incubated for another 24 hours at 37° C. After incubation, non-invasive cells were removed according to the manufacturer's protocol, and then 100% methanol was added to fix the cells for 15 minutes at room temperature. A Giemsa staining liquid (NACALAI TESQUE, # 37114-35) was added, and stained for 30 minutes at room temperature, followed by washing twice with PBS for 5 minutes each. After washing, the membrane on which the invasive cells remained was collected, and mounted on a slide glass. After drying for 15 minutes or more, microscopic observation and photographing image were conducted, and the cells on the image was counted. The results are shown in FIG. 30.

As shown in FIGS. 30A and B, it was confirmed that the number of invasive cells in the RPE cells increased, and the mobility of the RPE cells are enhanced by stimulation. RPE cells that are epithelial cells normally lack the mobility. Thus, the acquisition of the mobility by the epithelial cells that inherently lack the mobility is also a representative phenomenon in EMT.

Test Example 5-5

Morphologic Observation of RPE Cells in which EMT Occurs

Figure 31:
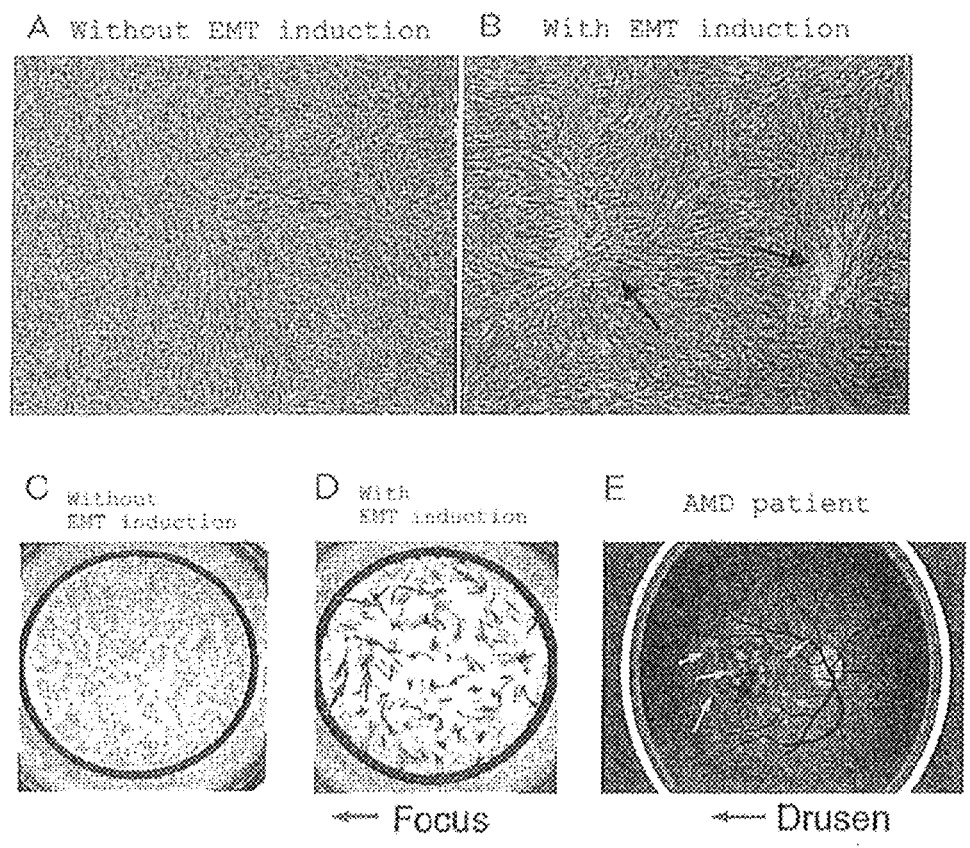
FIG. 31 includes photographs showing the results of EMT induction in RPE cells, verified by formation of a drusen-like structure.

RPE cells (ARPE-19) were seeded on a plate, and incubated for 5 days at 37° C. For the RPE cells, EMT was induced by the conditions described in Test example 5-1, and the cells were observed after 48 hours from the EMT induction. Further, for observing the overview of the plate by low power, the cells after observation were fixed by treating with a 4% paraformaldehyde solution for 30 minutes at room temperature, and then washed three times with PBS. After treating twice with 100% methanol for 10 minutes each at room temperature, a Giemsa staining liquid (NACALAI TESQUE, # 37114-35) was added, and stained for 15 minutes at room temperature. After washing three times with methanol, the cells were dried for 3 hours at room temperature. The dried cells were observed under a microscope. The results are shown in FIG. 31.

When EMT was induced in the RPE cells by the conditions described in Test example 5-1, Focus occurred as indicated by the arrow in FIG. 22B, and formation of a drusen-like structure was observed. On the other hand, when EMT was not induced, the PRE cells kept a confluent state without formation of Focus as shown in FIG. 31A. In FIGS. 31C and D, presence or absence of EMT induction is observed by low power. As shown in FIG. 31D, it was confirmed that when EMT is induced in RPE cells, the drusen-like structure (Focus) morphologically resembles drusen in the fundus fluorescence photograph of AMD patient (FIG. 31E). This demonstrated that in RPE cells, a drusen-like structure is formed by enhancement of mesenchymation by EMT induction. The drusen-like structure in RPE cells can be effectively used as a model that reproduces drusen in an AMD patient in vitro.

6

Assessment and/or Screening of EMT Suppressive Compound

Test Example 6-1

Change in Expression of EMT Marker 1

As described above, it was confirmed that by giving stimulation to RPE cells, change in EMT marker and enhancement of mobility occur, and a drusen-like structure is formed, and a cell model capable of inducing EMT could be constructed. Using the cell model, compounds that suppress EMT were selected. Also, by using the cell model, it is possible to assess an EMT suppressive compound.

RPE cells (ARPE-19) were seeded on a plate, and incubated for 5 days at 37° C. For RPE cells, EMT was induced by the conditions described in Test example 5-1, and a compound to be assessed (also referred to as test drug) was added simultaneously. As a control of EMT induction, a sample to which a compound to be assessed (test drug) is not added was used. After 48 hours from EMT induction, the cells were fixed by treating with a 4% paraformaldehyde solution for 30 minutes at room temperature, and then washed three times with PBS. The cells were treated with a 0.2% Triton-X/PBS solution for 5 minutes, and washed three times with PBS. The cells were stained with a fluorescent staining solution (0.2% Phalloidin-Alexa 568 (Molecular Probes, # A12380)/0.05% Hochest 33342 (Invitrogen, # H3570)/3% BSA-PBS) for 1 hour at room temperature, and then washed three times with PBS for 5 minutes each. The fluorescent-stained cells were imaged by using an Image Express Micro (available from Molecular Devices), and digitized by using a MetaXpress2.0 (available from Molecular Devices). By analyzing the degree of formation of Focus (Focus level) from the numerical data, a Focus formation suppressing rate was calculated according to the following Formula 1 on the basis of the numerical value at the time of no addition of a compound, and the EMT suppressive effect in each compound was verified. The degree of formation of Focus (Focus level) was determined according to the number and the volume of Focus as indexes.

$$\text{Focus formation suppressing rate \%} = \frac{\text{Focus level at EMT induction} - \text{Focus level at drug addition}}{\text{Focus level at EMT induction}} \times 100 \quad \text{(Formula 1)}$$

IC50 in the table was calculated using the following Formula 2.

$$IC50 = 10^{\wedge}(LOG(A/B)*(0.5-C)/(D-C)+LOG(B)) \quad \text{(Formula 2)}$$

A: Higher concentration sandwiching 50%
B: Lower concentration sandwiching 50%
C: Inhibition rate at lower concentration sandwiching 50%
D: Inhibition rate at higher concentration sandwiching 50%

As a result, EMT suppressive effect was observed in the following compounds.

TABLE 1

|  | Generic name | Trade name | IC50 (µM) |
| --- | --- | --- | --- |
| NSAIDs | Zaltoprofen | Peon, Soleton | 16.5 |
|  | Ibuprofen | BRUFEN | 18.0 |
|  | Oxaprozin | Alvo | 61.0 |
|  | Flurbiprofen | ROPION | 32.6 |
| Leukotriene antagonist | Pranlukast | ONON | 1.1 |
|  | Zafirlukast | ACCOLATE | 3.8 |
|  | Montelukast | KIPRES | 3.4 |
| Chemical mediator release suppressor | Amlexanox | SOLFA | 32.5 |
| Aldose reductase inhibitor | Epalrestat | KINEDAK | 16.9 |

Representative five compounds (oxaprozin, epalrestat, zafirlukast, amlexanox, zaltoprofen) among the EMT suppressive compounds listed in the above Table 1 were assessed for an EMT suppressive effect using the cell model as described above.

RPE cells (ARPE-19) were seeded on a plate, and incubated for 5 days at 37° C. For the RPE cells, EMT was induced in the conditions described in Test example 5-1, and the five representative compounds (oxaprozin, epalrestat, zafirlukast, amlexanox, zaltoprofen) were added simultaneously, and the cells were collected after 48 hours from induction of EMT. As a control, a sample to which a compound to be assessed (test drug) is not added was used. The collected cells were washed with PBS, and 350 μL of an RLT buffer was added to prepare a lysate for RNA extraction. Total RNA was extracted from the lysate using an RNeasy Micro kit (QIAGEN, # 74004), and from 2 μg of the obtained RNA, cDNA was prepared using a SuperScript III First-Strand Synthesis SuperMix for qRT-PCR (Invitrogen, # 11752-250). Using 50 ng of the obtained cDNA as a template, a real-time PCR (ABI Prism 7500 Sequence Detection System) was conducted according to the manufacturer's protocol, and expression of mRNA of each gene was quantified. Specific primers for respective genes were purchased from Invitrogen. Ct (Threshold Cycle) value of each gene was calculated as a percentage to a non-treated sample after normalization by endogenous control. The results are shown in FIG. 3 to FIG. 7.

In each graph of FIG. 3 to FIG. 7, the left bar graph indicates an expression amount of each gene when EMT is not induced. The center bar graph indicates an expression amount of each gene when EMT is induced. The right bar graph indicates an expression amount of each gene when an EMT suppressive compound is administered. Also, FIG. 3 to FIG. 7 indicate the results using oxaprozin, epalrestat, zafirlukast, amlexanox, and zaltoprofen, respectively as an EMT suppressive compound.

In the present description, the EMT markers are also described respectively by the following abbreviated names.
Cadherin: CDH (CDH2, CDH3, etc.)
Matrix metalloproteinase: MMP (MMP1, MMP3, MMP7, etc.)
Fibronectin: FN (FN1, etc.)
Vimentin: VIM
Collagen type 1α1: COL1A1
Collagen type 1α2: COL1A2
Collagen type 5α2: COL5A2
Collagen type 5α3: COL5A3
Collagen type 6α3: COL6A3
Collagen type 13π1: COL13A1
Laminin β3: LAMB3
Laminin γ2: LAMC2
Hyaluronan-Mediated Motility Receptor: HMMR
Tenascin C: TNC
Zinc Finger E-Box Binding Homeobox 2: ZEB2
Serglycin: SRGN
chondroitin sulfate proteoglycan 4: CSPG4

As shown in FIG. 3 to FIG. 7, among the EMT markers, Snail, Slug, CDH3, MMP1, and MMP7 which are mesenchymal markers, and COL5A3, COL6A3, LAMC2, HMMR, and TNC which are ECMs exhibited suppressed expression regardless of the applied EMT suppressive compound. As a result, these ten EMT markers were confirmed to be indexes that are commonly suppressed by the EMT suppressive compounds. Even with EMT markers other than these ten markers, decrease in expression was observed in ZEB2, MMP3, COL1A1, COL1A2, CSPG4, and SRGN in the case of oxaprozin as shown in FIG. 3. As shown in FIG. 4, decrease in expression was observed in ZEB2, CDH2, FN1, VIM, COL1A1, COL1A2, COL5A2, COL13A1, CSPG4, and SRGN in the case of epalrestat. As shown in FIG. 5, decrease in expression was observed in MMP3, COL13A1, LAMB3, or CSPG4 in the case of zafirlukast. As shown in FIG. 6, decrease in expression was observed in ZEB2, CDH2, MMP3, COL1A1, and COL13A1 in the case of amlexanox. As shown in FIG. 7, decrease in expression was observed in ZEB2, FN1, COL13A1, and CSPG4 in the case of zaltoprofen. It was confirmed that these EMT markers can be indexes that are suppressed by EMT suppressive compounds.

Test Example 6-2

Change in Expression of EMT Marker 2

For the five compounds (flufenamic acid aluminum, mefenamic acid, sulindac, tiaprofenic acid, seratrodast), IC50 was determined in the same manner as in Test example 6-1. The results are shown in Table 2.

TABLE 2

| | Generic name | Trade name | IC50 (μM) |
|---|---|---|---|
| NSAIDs | Flufenamic acid | OPYRIN | 4.4 |
| | Mefenamic acid | PONTAL | 12.4 |
| | Sulindac | Clinoril | 35.3 |
| | Tiaprofenic acid | Surgam | 373.9 |
| Thromboxane A2 receptor antagonist | Seratrodast | Bronica | 54.6 |

As shown in Table 2, five compounds confirmed to have an EMT suppressive effect (flufenamic acid aluminum (addition concentration: 28 μM (Cmax)), mefenamic acid (addition concentration: 39 μm (Cmax)), sulindac (addition concentration: 100 μM), tiaprofenic acid (addition concentration: 1000 μM), and seratrodast (addition concentration: 31 μM (Cmax))) were assessed for change in expression of EMT markers in the same manner as in Test example 6-1. The results are shown in FIG. 8 to FIG. 12, respectively.

As shown in FIG. 8 to FIG. 12, it was confirmed the five EMT suppressive compounds (flufenamic acid aluminum, mefenamic acid, sulindac, tiaprofenic acid, seratrodast) also lower expression of EMT markers at the time of EMT induction.

Test Example 6-3

Suppressing Test of Enhancement of Mobility

Using the Invasion Assay method described in the foregoing Test example 5-4, influence of EMT suppressive compounds in RPE cells having enhanced mobility by EMT was examined.

RPE cells (ARPE-19) were seeded on a plate, and incubated for 5 days at 37° C. For the RPE cells, EMT was induced in the conditions described in Test example 5-1, and five compounds (oxaprozin, epalrestat, zafirlukast, amlexanox, zaltoprofen) were added, and the cells were collected after 24 hours from induction of EMT. The collected cells were seeded in a BD Biocoat Matrigel invasion chamber (BD Bioscience, # 354480), and incubated for another 24 hours at 37° C. After incubation, non-invasive cells were removed according to the manufacturer's protocol, and then 100% methanol was added to fix the cells for 15 minutes at room temperature. A Giemsa staining liquid (NACALAI TESQUE, # 37114-35) was added, and stained for 30 minutes at room temperature, followed by washing twice with PBS for 5 minutes each. After washing, the membrane on which the invasive cells remained was collected, and mounted on a slide glass. After drying for 15 minutes or more, microscopic observation and photographing image were conducted, and the invasive cells were counted. The results are shown in FIG. 32 to FIG. 34.

Figure 32:
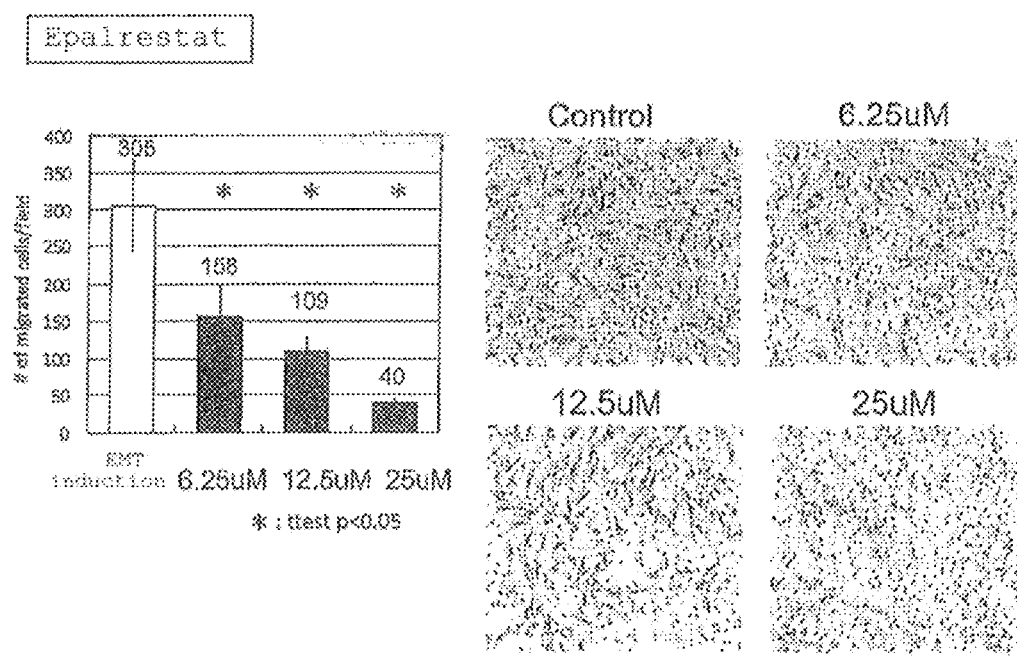
FIG. 32 is a graph showing that enhancement of mobility is suppressed by an EMT suppressive compound in an EMT induction model of RPE cells.
Figure 33:
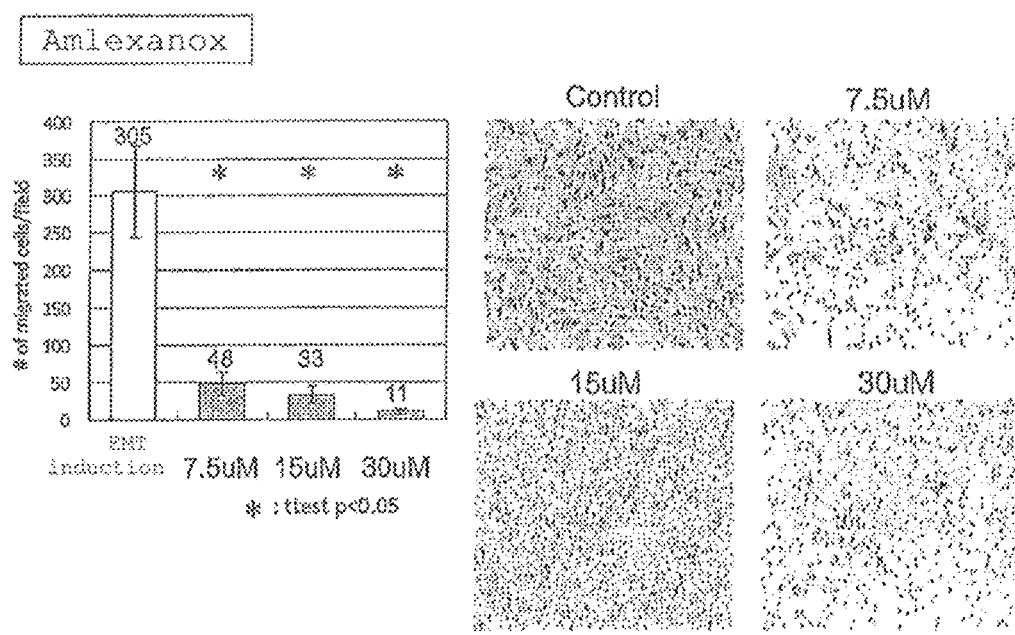
FIG. 33 is a graph showing that enhancement of mobility is suppressed by an EMT suppressive compound in an EMT induction model of RPE cells.
Figure 34:
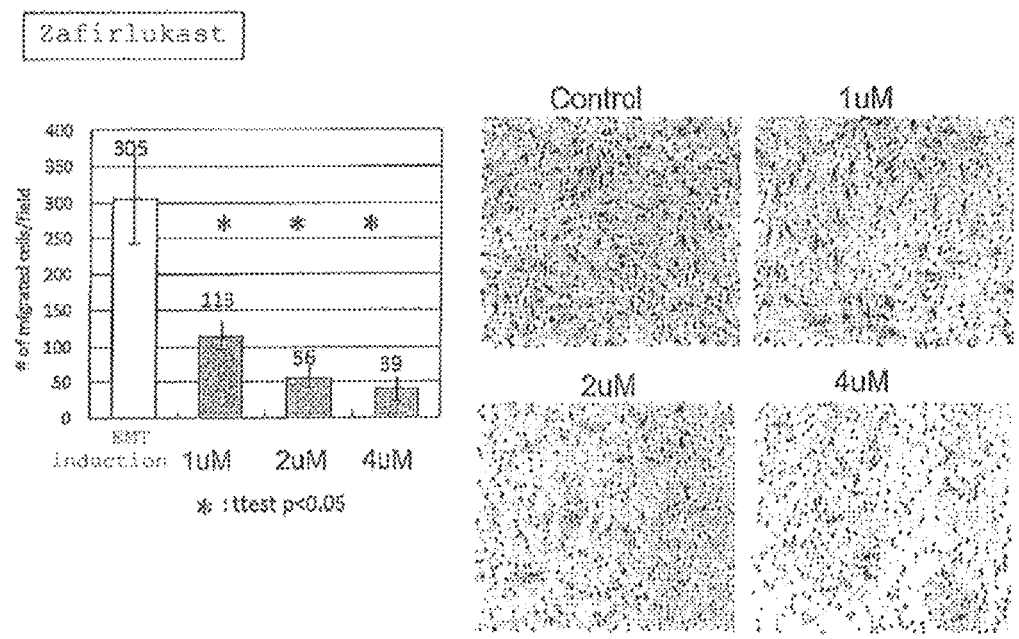
FIG. 34 is a graph showing that enhancement of mobility is suppressed by an EMT suppressive compound in an EMT induction model of RPE cells.
Figure 35:
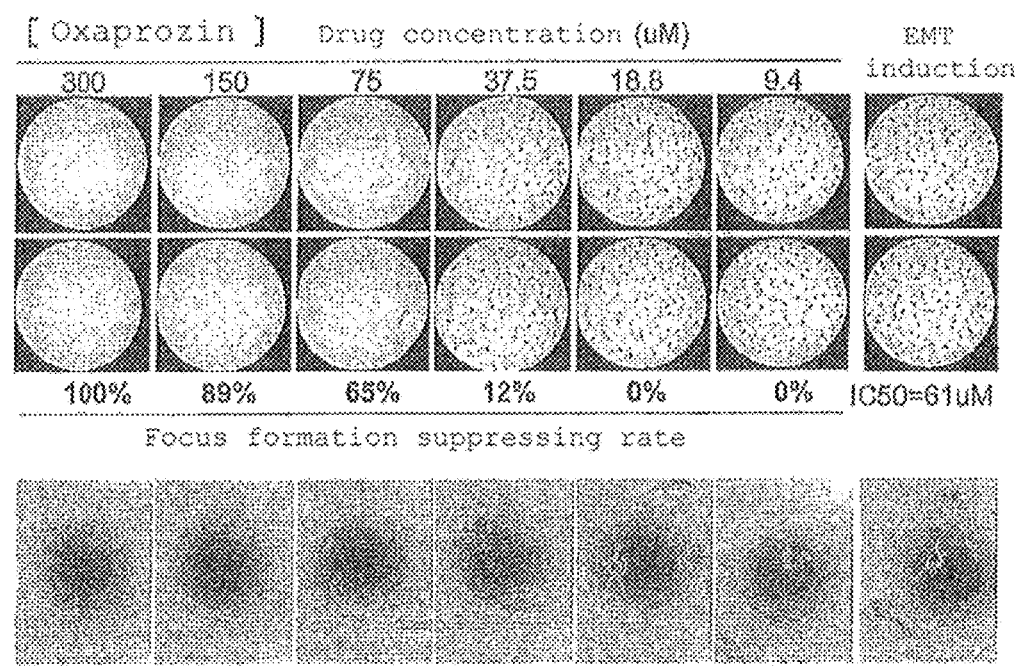
FIG. 35 includes photographs showing that an EMT suppressive compound suppresses a drusen-like structure in an EMT induction model of RPE cells.
Figure 36:
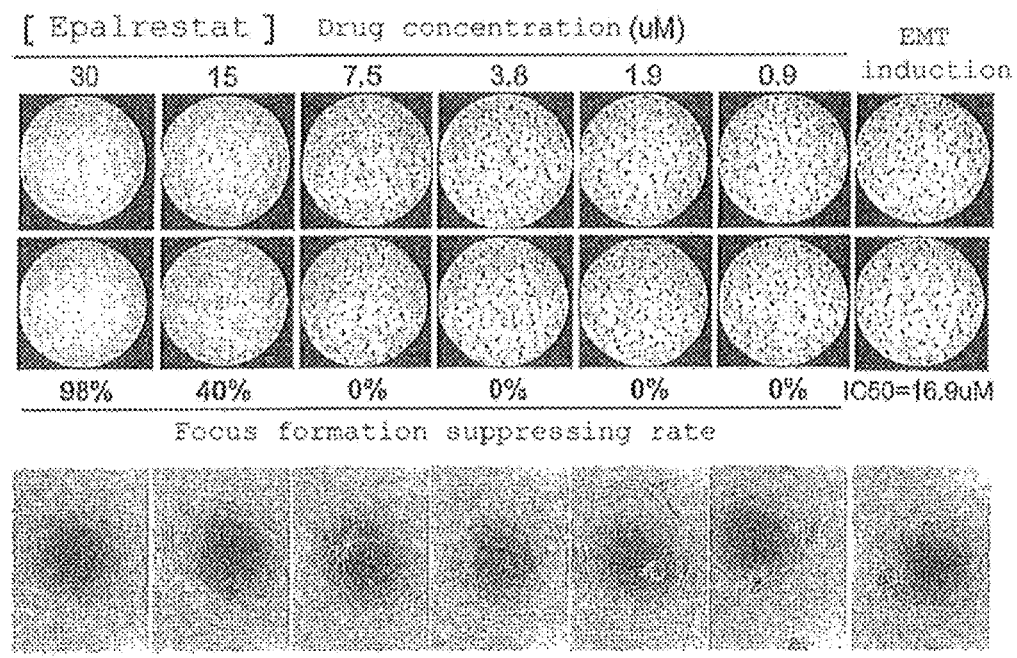
FIG. 36 includes photographs showing that an EMT suppressive compound suppresses a drusen-like structure in an EMT induction model of RPE cells.
Figure 37:
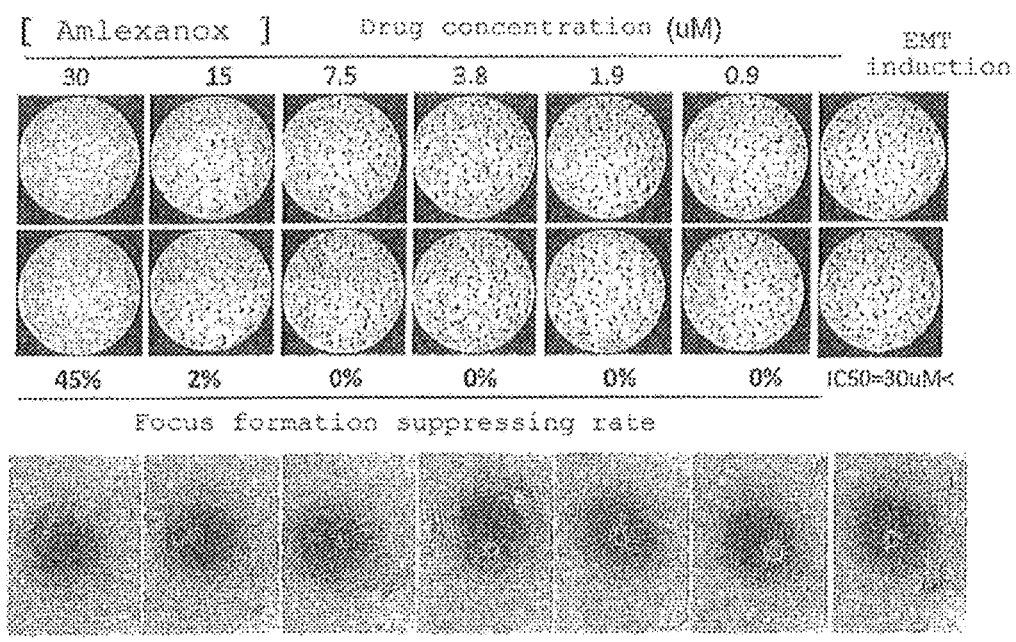
FIG. 37 includes photographs showing that an EMT suppressive compound suppresses a drusen-like structure in an EMT induction model of RPE cells.
Figure 38:
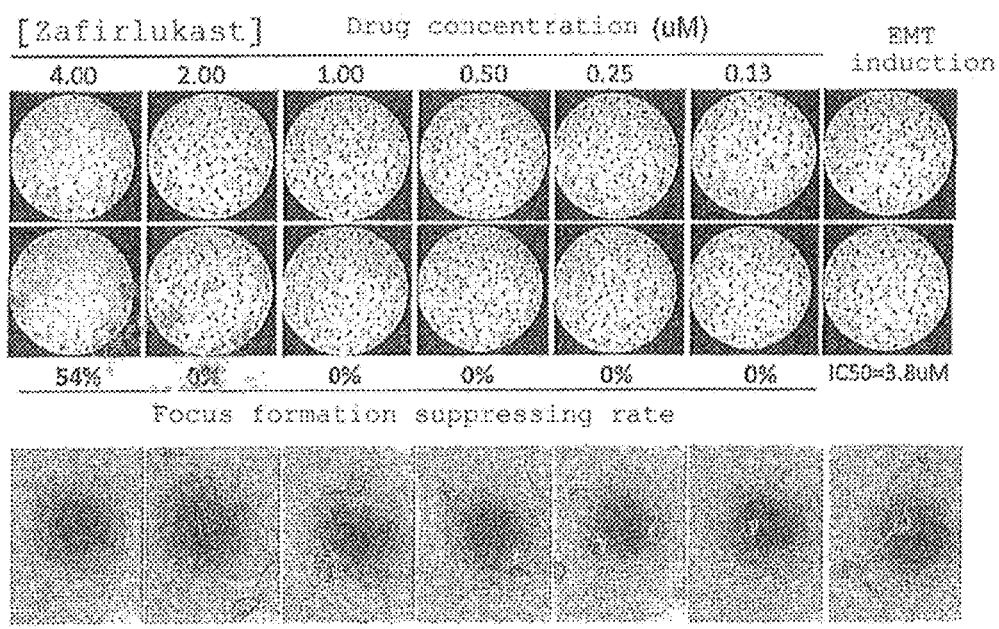
FIG. 38 includes photographs showing that an EMT suppressive compound suppresses a drusen-like structure in an EMT induction model of RPE cells.
Figure 39:
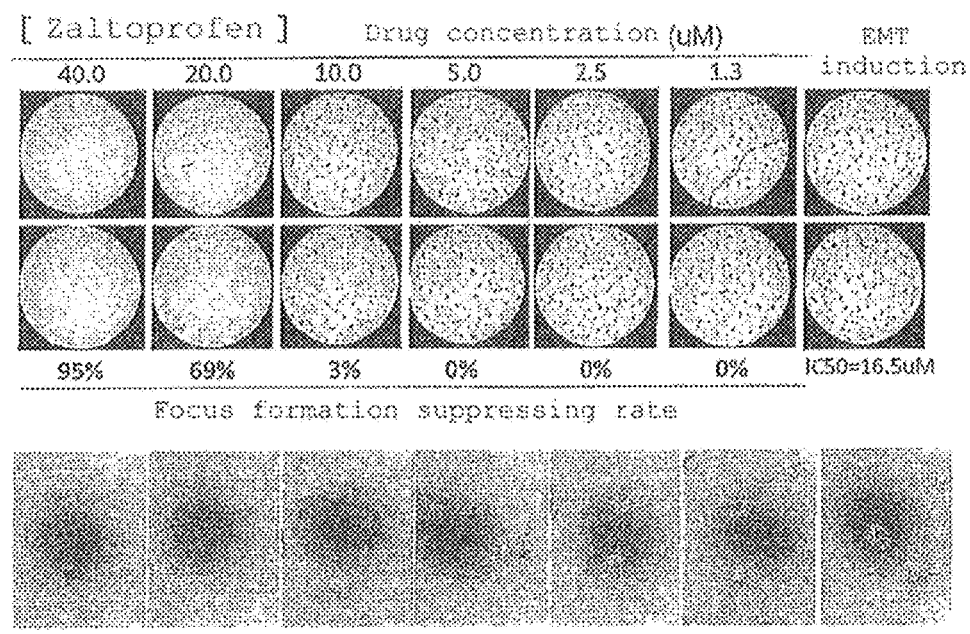
FIG. 39 includes photographs showing that an EMT suppressive compound suppresses a drusen-like structure in an EMT induction model of RPE cells.

FIG. 32 to FIG. 34 indicate the results using epalrestat, amlexanox, and zafirlukast, respectively as an EMT suppressive compound. Also in bar graphs of FIG. 32 to FIG. 34, the left open bar graph indicates the number of invasive cells in RPE cells at the time of EMT induction, the right solid bar graphs indicate the numbers of invasive cells in RPE cells when EMT suppressive compounds are added in concentrations sequentially rising from the left.

As shown in FIG. 32 to FIG. 34, it was confirmed that in RPE cells, the mobility induced by EMT is suppressed significantly in a concentration-dependent manner of the EMT suppressive compound.

7

Assessment of Drug Efficacy by Drusen-Like Structure Suppressing Test

RPE cells (ARPE-19) were seeded on a plate, and incubated for 5 days at 37° C. For the RPE cells, EMT was induced in the conditions described in Test example 5-1, and five compounds (oxaprozin, epalrestat, zafirlukast, amlexanox, zaltoprofen) were simultaneously added, and the cells were observed after 48 hours from induction of EMT. As a control of EMT induction, a sample to which a compound to be assessed (test drug) is not added was used. The cells after observation were fixed by treating with a 4% paraformaldehyde solution for 30 minutes at room temperature, and then washed three times with PBS. The cells were treated with a 0.2% Triton-X/PBS solution for 5 minutes, and washed three times with PBS. The cells were stained with a fluorescent staining solution (0.2% Phalloidin-Alexa 568 (Molecular Probes, # A12380)/0.05% Hochest-33342 (Invitrogen, # H3570)/3% BSA-PBS) for 1 hour at room temperature, and then washed three times with PBS for 5 minutes each. The fluorescent-stained cells were imaged by using an Image Express Micro (available from Molecular Devices), and digitized by using a MetaXpress2.0 (available from Molecular Devices). By analyzing the degree of formation of Focus from the numerical data, a Focus formation suppressing rate was calculated on the basis of the case without addition of a compound and the case without EMT induction, and the EMT suppressive effect in each compound was verified. For observing the overview by low power, the cells after acquisition of the fluorescent image were treated twice with 100% methanol for 10 minutes each at room temperature, and a Giemsa staining liquid (NACALAI TESQUE, # 37114-35) was added, and stained for 15 minutes at room temperature. After washing three times with methanol, the cells were dried for 3 hours at room temperature. The dried cells were observed under a microscope. The results are shown in FIG. 35 to FIG. 39. The Focus formation suppressing rate was calculated according to Formula 1 shown in the foregoing Test example 6-1.

FIG. 35 to FIG. 39 indicate the results using oxaprozin, epalrestat, amlexanox, zafirlukast, and zaltoprofen, respectively as an EMT suppressive compound. As shown in FIG. 35 to FIG. 39, it was confirmed that every EMT suppressive compound suppresses a drusen-like structure formed in the RPE cell model in a concentration-dependent manner. Specifically, IC50 values in the drusen-like structure suppressing tests were 61.0 μM in oxaprozin, 16.9 μM in epalrestat, 32.5 μM in amlexanox, 3.8 μM in zafirlukast, and 16.5 μM in zaltoprofen.

On the basis of the new finding that drusen are structures caused by EMT occurring in RPE cells, it was demonstrated that drusen are suppressed by applying an EMT suppressive compound for drusen. These results infer that even a known EMT suppressive compound exerts a similar effect on drusen.

By the following method, maximum drug plasma concentration (Cmax) was determined for the five EMT suppressive compounds from the interview form and the package insert of each drug.

The results are shown in Table 3.

TABLE 3

|  | Generic name | Cmax (μM) |
|---|---|---|
| NSAIDs | Oxaprozin | 340.9 |
|  | Zaltoprofen | 20.4 |
| Leukotriene antagonist | Zafirlukast | 0.8 |
| Chemical mediator release suppressor | Amlexanox | 16.0 |
| Aldose reductase inhibitor | Epalrestat | 12.2 |

As shown in Table 3, the five EMT suppressive compounds showed blood concentrations that are sufficient for expectation for the effect on AMD.

Test Example 8

In Vivo Model Test for Assessment of Drusen Suppression

Test Example 8-1

Induction of Drusen-Like Structure Formation in Posterior Segment of Eyeball (Retinal Region)

(1) Method for Inducing Drusen-Like Structure in Posterior Segment of Eyeball (Retinal Region) by Inducing Inflammation In the vicinity of the retina in the posterior segment of eyeball of mouse, 400 ng of Recombinant Mouse TNF-a (R&D Systems, # 410-MT) was administered.

The administration method is as follows.

1) Prepare 2.5 μL of TNF-a dissolved in PBS (160 ng/μL).
2) Spread out the eyelid to get a better view of the mouse eyeball.
3) Insert a needle to the point where slight resistance is felt, and inject the drug liquid (400 ng/eye).

(2) Method for Preparing Eyeball Tissue Sample

After two weeks from administration, an eye ball was extracted, and a formalin-fixed, paraffin-embedded block was prepared.

(3) Morphologic Observation of RPE Cells

The tissue sample was deparaffinized by treating three times with xylene for 5 minutes each, twice with 100% ethanol for 1 minute each, with 90% ethanol for 1 minute, with 80% ethanol for 1 minute, with 70% ethanol for 1 minute, and with water for 5 minutes. Staining was conducted with a Mayer's hematoxylin solution for 4 minutes, and with an eosin liquid for 1 minute. After treating for 5 minutes in flowing water, treatments were conducted with 70% ethanol for 1 minute, with 80% ethanol for 1 minute, with 90% ethanol for 1 minute, twice with 100% ethanol for 1 minute each, and three times with xylene for 5 minutes each, followed by mounting with Marinol. After drying for 15 minutes or more at room temperature, the untreated RPE cells, and the RPE cells in which inflammation is induced were observed. The results are shown in FIG. 40.

Figure 40:
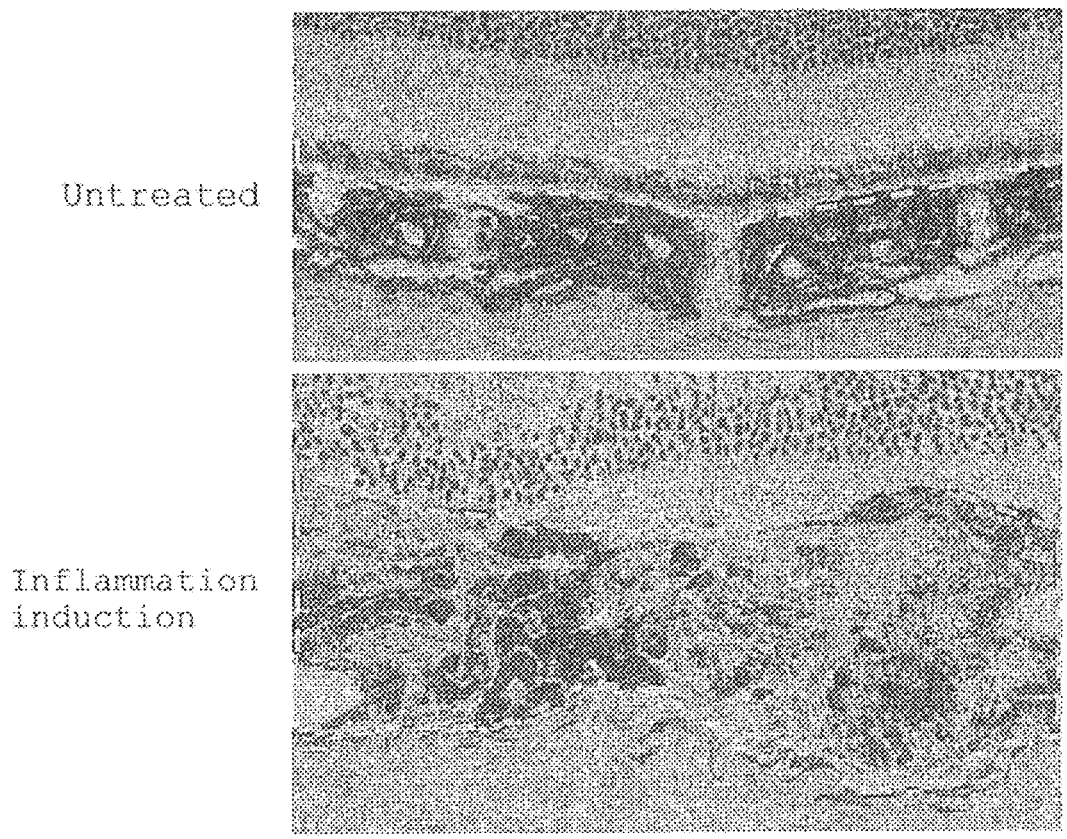
FIG. 40 includes photographs showing the result of induction of a drusen-like structure in an in vivo model test for assessing drusen suppression.

As shown in FIG. 40, a drusen-like structure (the part surrounded by the dotted line) was formed in the retinal region by induction of inflammation. It was confirmed that the retinal pigment epithelial cells of the untreated group assume a cubic shape, and are in close contact with the neighboring cells, and align in a single layer (upper photograph). On the other hand, it was confirmed that after induction of inflammation, the retinal pigment epithelial cells aligning in a single layer are not observed, but exist inside or around the drusen-like structure, and close binding with the neighboring cells disappear, and the shape changes into a spindle shape from the cubic shape (lower photograph).

(4) Method for Assessing Each Marker by Immunohistochemistry

Figure 41:
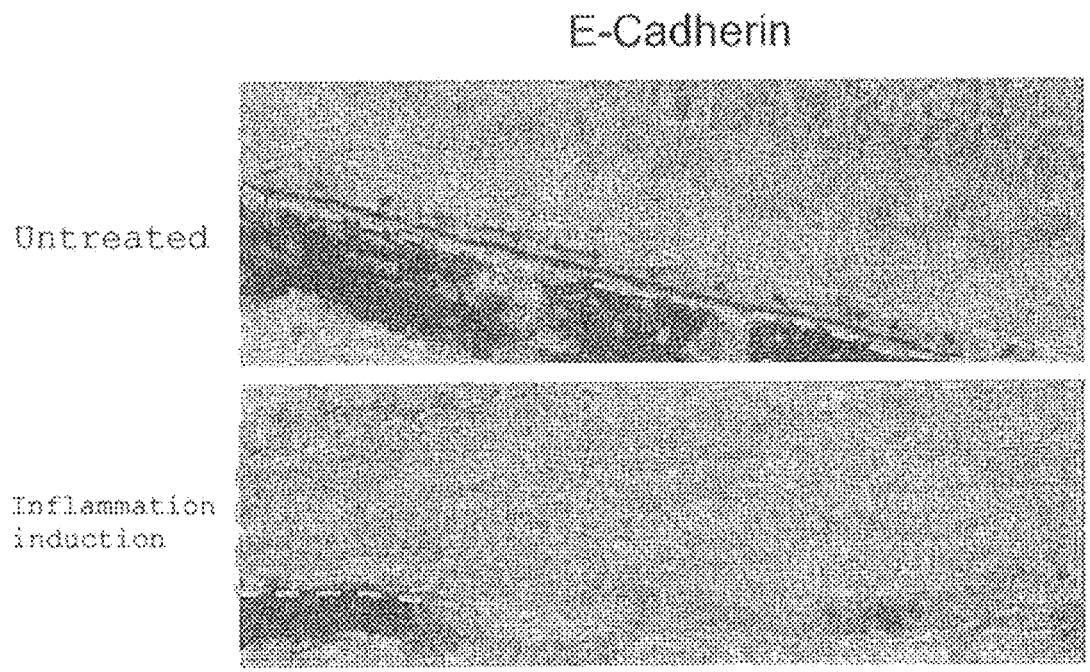
FIG. 41 includes photographs showing the result of staining of E-Cadherin in an induced drusen-like structure.
Figure 42:
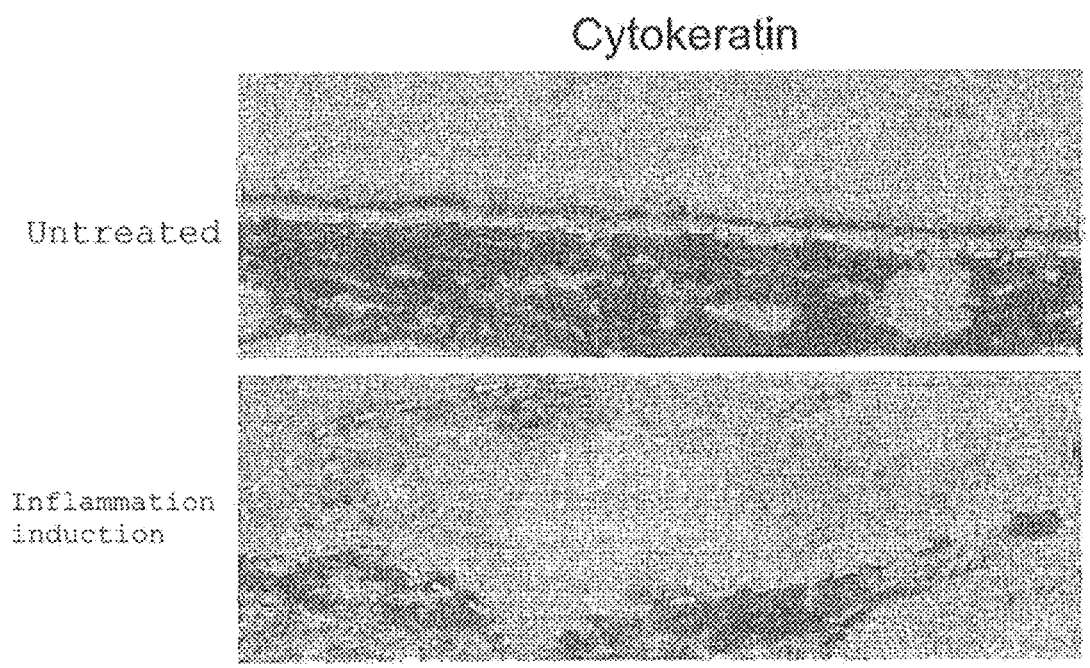
FIG. 42 includes photographs showing the result of staining of Cytokeratin in an induced drusen-like structure.
Figure 43:
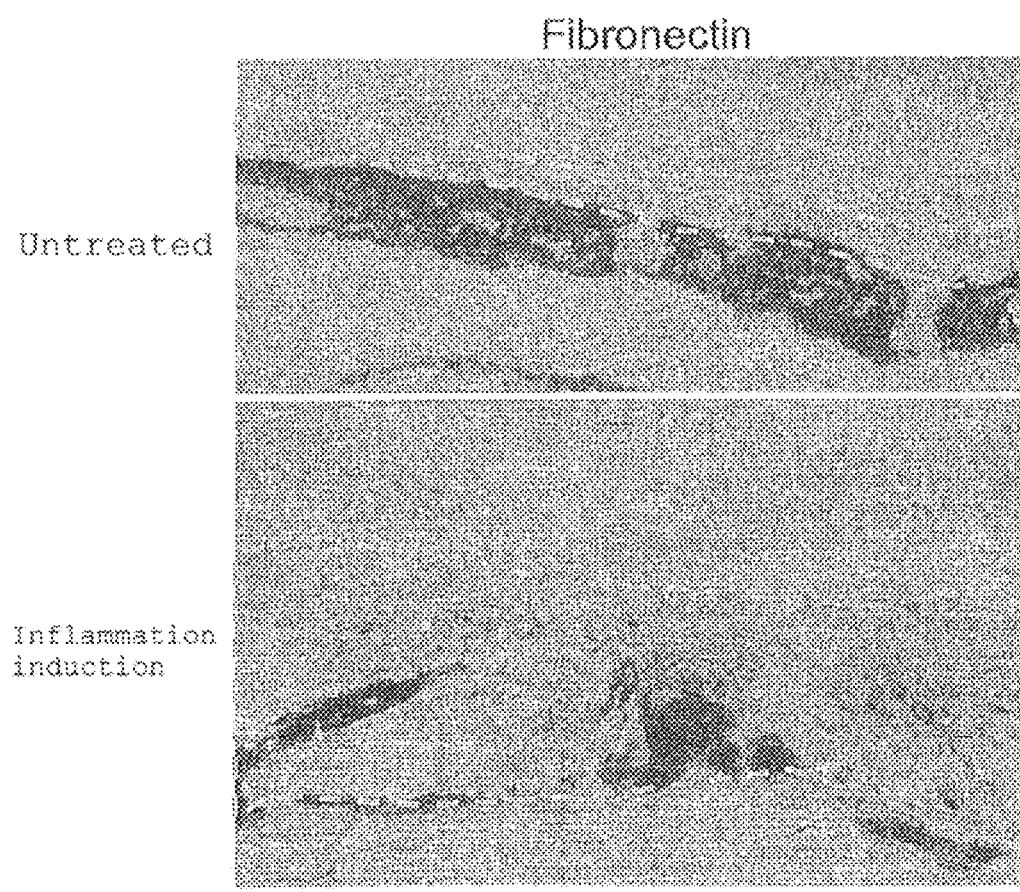
FIG. 43 includes photographs showing the result of staining of Fibronectin in an induced drusen-like structure.
Figure 44:
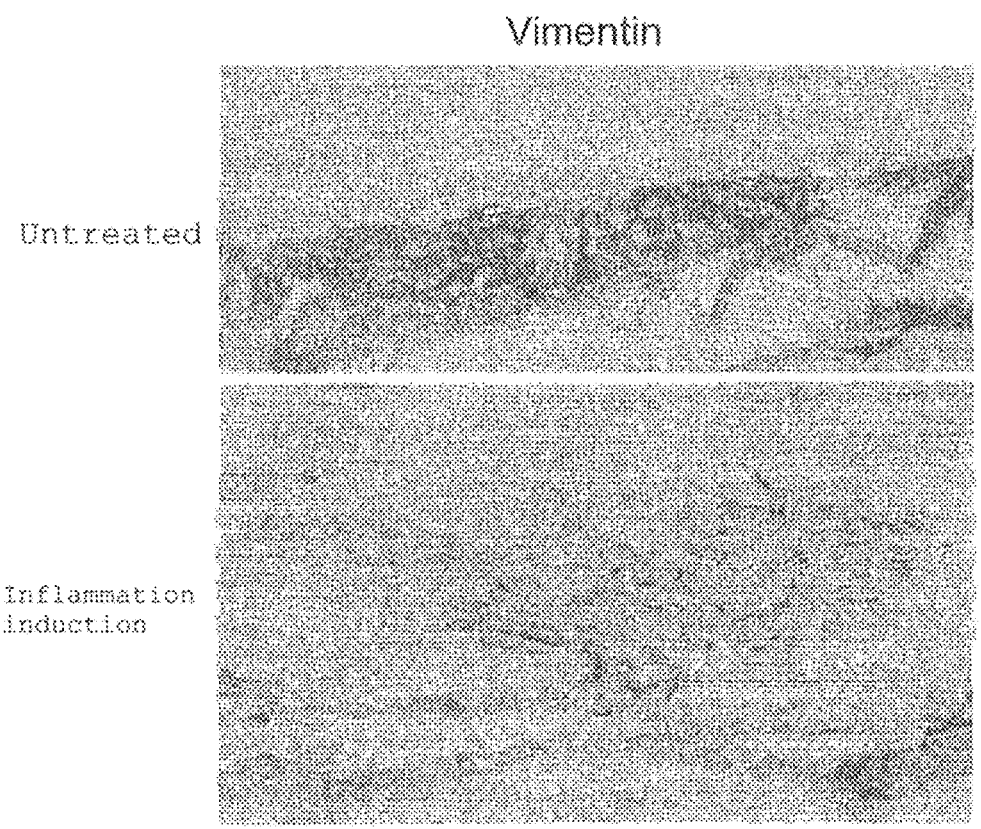
FIG. 44 includes photographs showing the result of staining of Vimentin in an induced drusen-like structure.

An eyeball tissue segment was prepared from a block. After incubation for 30 minutes in a gas-phase incubator at 56° C., the tissue sample was deparaffinized by treating three times with xylene for 5 minutes each, twice with 100% ethanol for 1 minute each, with 90% ethanol for 1 minute, with 80% ethanol for 1 minute, with 70% ethanol for 1 minute, and with water for 5 minutes. After removing a melanin pigment in tissues using Delicate Melanin Bleach Kit for Special Stains and IHC (Polysciences, # 24909-1) according to the manufacturer's protocol, a microwave treatment using a citrate buffer pH 6.0 was conducted for 10 minutes to activate the antigen. After standing still for 30 minutes at room temperature, treatments were conducted with PBS for 5 minutes, with a 3% hydrogen peroxide/PBS solution for 5 minutes, and with PBS for 5 minutes to inactivate an endogenous peroxidase. The sample was stood still in a 3% BSA/PBS solution for 30 minutes at room temperature to block the tissues. As primary antibodies, an anti-E-Cadherin antibody (BD Biosciences, # 610182) that was 500-fold diluted with a 1.5% BSA/PBS solution, and an anti-Cytokeratin antibody (Sigma, # C2931) that was 1000-fold diluted, and an anti-Fibronectin antibody (abcam, # 45688) that was 1000-fold diluted, and an anti-Vimentin antibody (Cell signaling Technology, # 5741) that was 100-fold diluted were added in an amount of 200 µL per one tissue, and caused to react with the tissues for 17 hours at 4° C. The tissues reacted with the primary antibodies were washed three times with PBS for 5 minutes each, then caused to react with a secondary antibody (a Mouse on Mouse (M. O. M.) Elite Peroxidase Kit (Vector Laboratories, # PK-2200) for the anti-E-Cadherin antibody and the anti-Cytokeratin antibody, and a VECTASTAIN Elite ABC Rabbit IgG Kit (Vector Laboratories, # PK-6101) for the anti-Fibronectin antibody and the anti-Vimentin antibody) for 30 minutes at room temperature, then washed three times with PBS for 5 minutes each, and then subjected to an ABC reaction for 30 minutes at room temperature according to the manufacturer's protocol. After washing the tissues three times with PBS for 5 minutes each, color development was caused for 3 minutes at room temperature using an ImmPACT AMEC Red Peroxidase (HRP) Substrate (Vector Laboratories, # SK-4285). The color-developed tissues were stained by using a New hematoxylin Type M (MUTO PURE CHEMICALS CO., LTD., # 30141), and then stood still in flowing water for 3 minutes, and treated with 70% ethanol for 1 minute, with 80% ethanol for 1 minute, with 90% ethanol for 1 minute, twice with 100% ethanol for 1 minute each, and three times with xylene for 5 minutes each, and mounted with the use of Marinol. After drying for 15 minutes or more at room temperature, observation was conducted. The results for E-Cadherin are shown in FIG. 41. The results for Cytokeratin are shown in FIG. 42. The result for Fibronectin are shown in FIG. 43. The result for Vimentin are shown in FIG. 44.

As shown in FIG. 41, in the untreated retinal epithelial cells, strongly positive staining of E-Cadherin was observed between cells, and strong intracellular adhesion was retained (upper photograph). On the other hand, in the retinal pigment epithelial cells inside or around the drusen-like structure formed by induction of inflammation, staining disappeared (lower photograph).

As shown in FIG. 42, in the untreated retinal epithelial cells, strongly positive staining of Cytokeratin was observed between cells (upper photograph). On the other hand, in the retinal pigment epithelial cells especially around the drusen-like structure formed by induction of inflammation, staining disappeared (lower photograph).

As shown in FIG. 43, in the untreated retinal epithelial cells (the part surrounded by the dotted line), the signal was negative, and expression of Fibronectin was not observed (upper photograph). On the other hand, inside and around the drusen-like structure that was formed by induction of inflammation, staining was positive, and expression of Fibronectin was observed (lower photograph).

As shown in FIG. 44, in the untreated retinal epithelial cells (the part surrounded by the dotted line), the signal was negative, and expression of Vimentin was not observed (upper photograph). On the other hand, inside and around the drusen-like structure that was formed by induction of inflammation, staining was positive and expression of Vimentin was observed (lower photograph).

Test Example 8-2

Pharmacological Assessment: Effect of Suppressing Formation of Drusen-Like Structure (1) Method for Inducing Drusen-Like Structure in Posterior Segment of Eyeball (Retinal Region) by Inducing Inflammation In the vicinity of the retina in the posterior segment of eyeball of mouse, 400 ng of Recombinant Mouse TNF-a (R&D Systems, # 410-MT) was administered according to the method described in Test example 8-1.

(2) Administration of Compound to be Assessed

A compound to be assessed was suspended in a 0.5% carboxymethyl cellulose aqueous solution, and orally administered with a sound for 14 days at a dose of 600 mg/kg/day for oxaprozin, 600 mg/kg/day or epalrestat, or 40 mg/kg/day for zaltoprofen.

(3) Morphologic Observation of RPE Cells

According to the method described in Test example 8-1, an eyeball tissue sample was prepared, and the untreated RPE cells and the RPE cells in which inflammation was induced were observed by HE staining, immunostaining of E-Cadherin, or immunostaining of Fibronectin.

Figure 45:
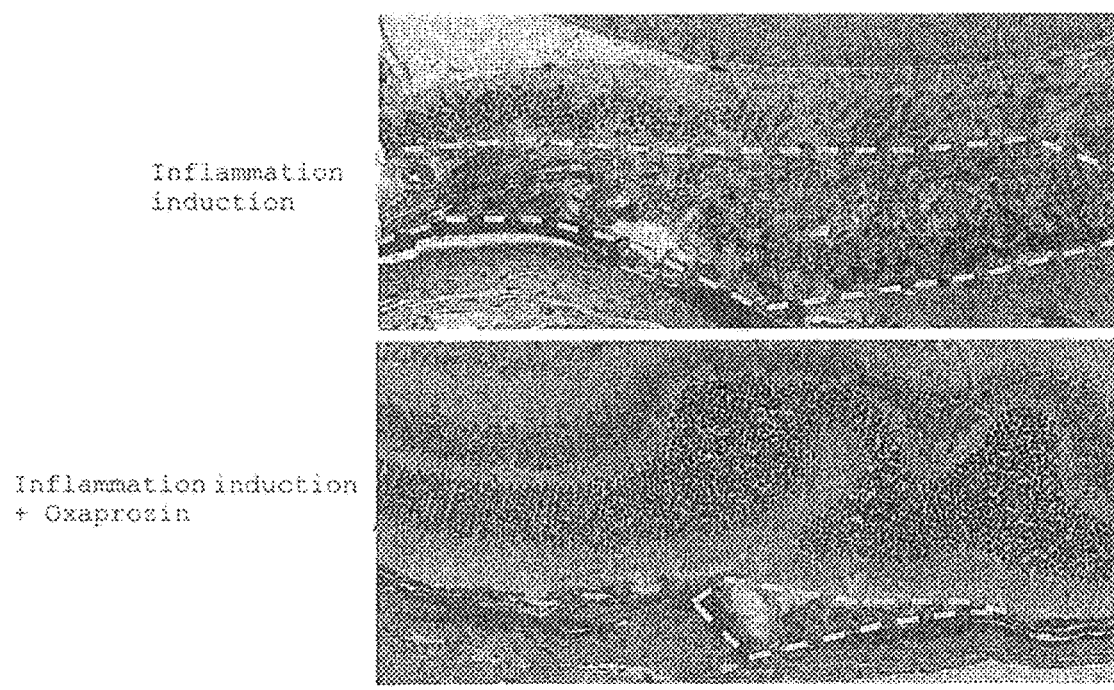
FIG. 45 includes photographs showing the pharmacological assessment of oxaprozin for formation of a drusen-like structure, indicated by HE staining.
Figure 46:
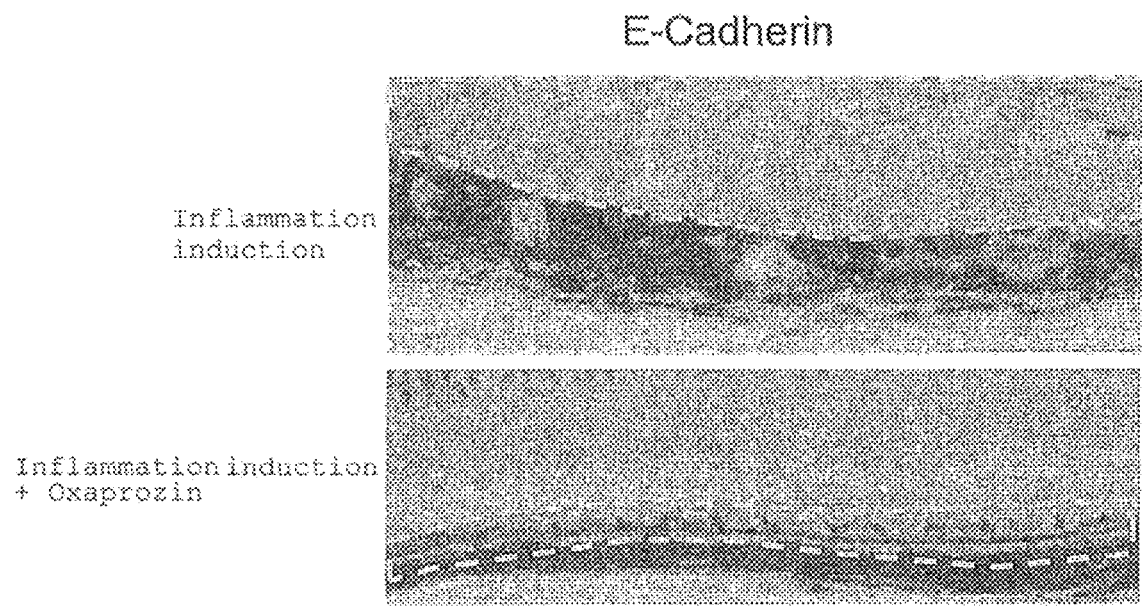
FIG. 46 includes photographs showing the pharmacological assessment of oxaprozin for formation of a drusen-like structure, indicated by immunostaining of E-Cadherin.
Figure 47:
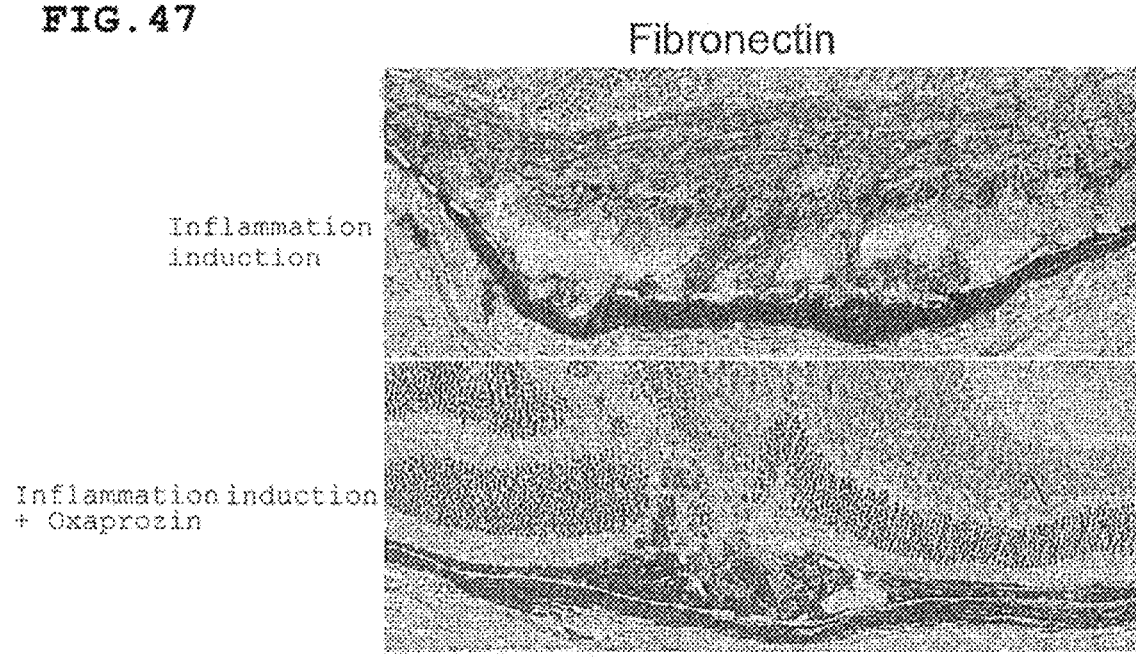
FIG. 47 includes photographs showing the pharmacological assessment of oxaprozin for formation of a drusen-like structure, indicated by immunostaining of Fibronectin.
Figure 48:
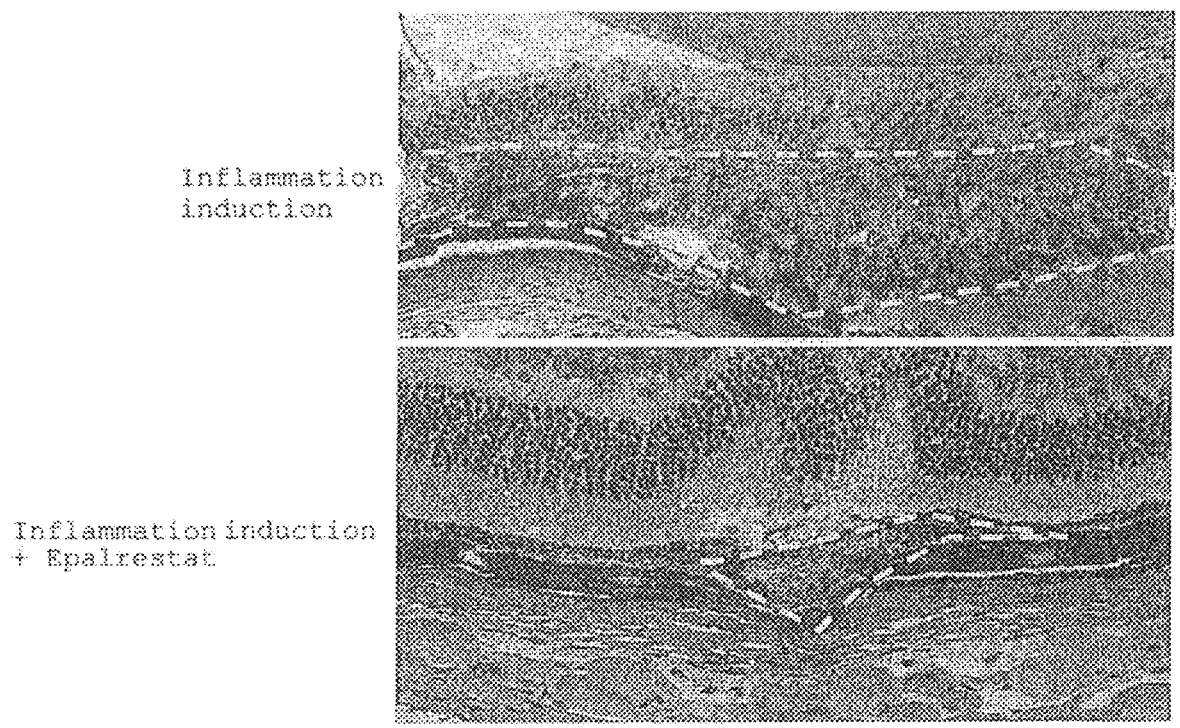
FIG. 48 includes photographs showing the pharmacological assessment of epalrestat for formation of a drusen-like structure, indicated by HE staining.
Figure 49:
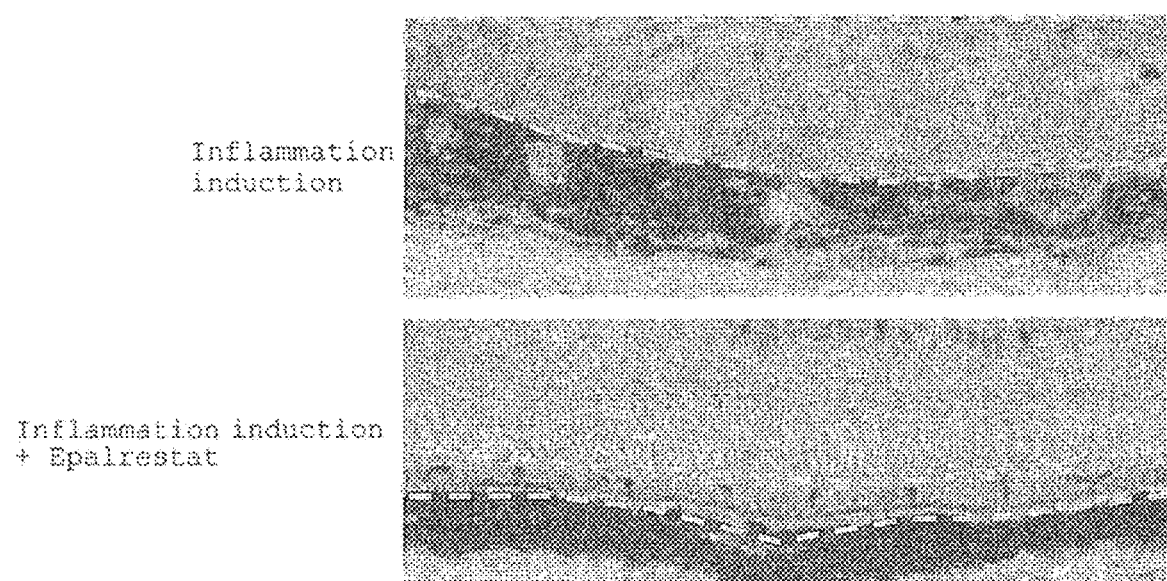
FIG. 49 includes photographs showing the pharmacological assessment of epalrestat for formation of a drusen-like structure, indicated by immunostaining of E-Cadherin.
Figure 50:
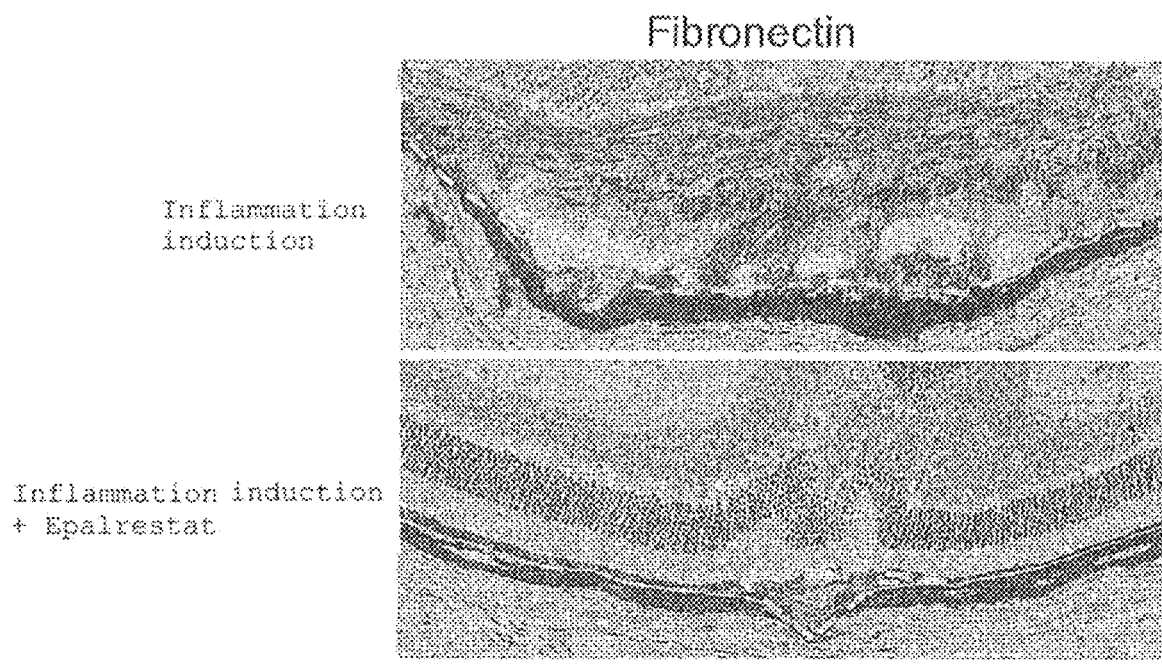
FIG. 50 includes photographs showing the pharmacological assessment of epalrestat for formation of a drusen-like structure, indicated by immunostaining of Fibronectin.
Figure 51:
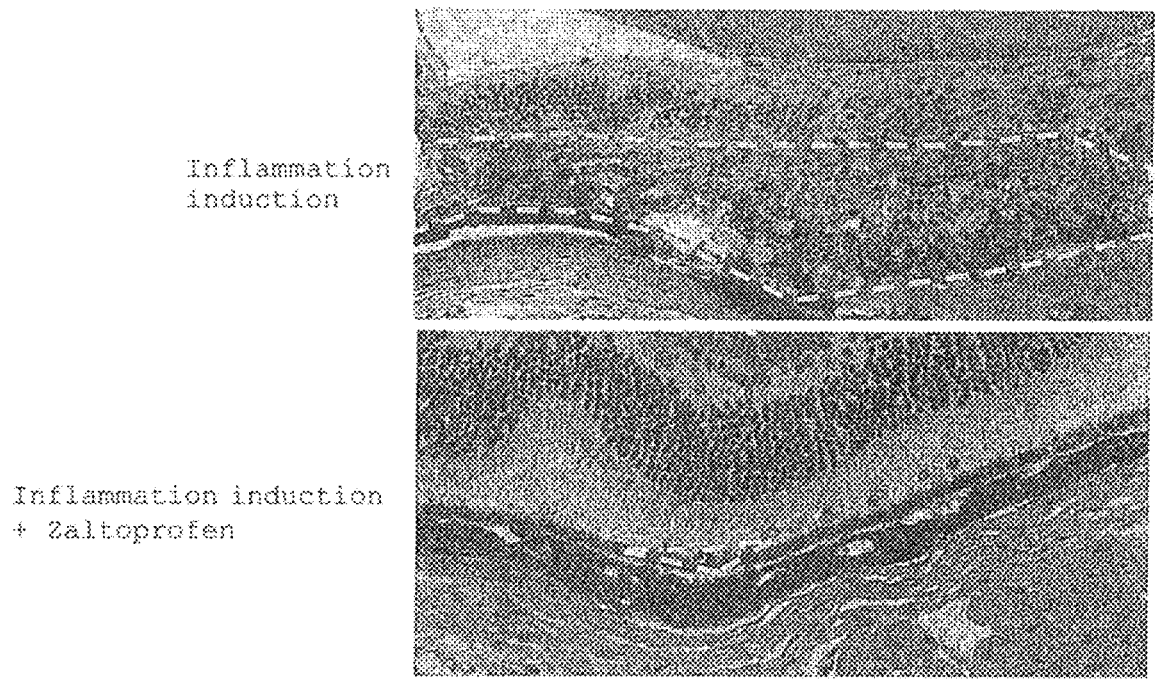
FIG. 51 includes photographs showing the pharmacological assessment of zaltoprofen for formation of a drusen-like structure, indicated by HE staining.
Figure 52:
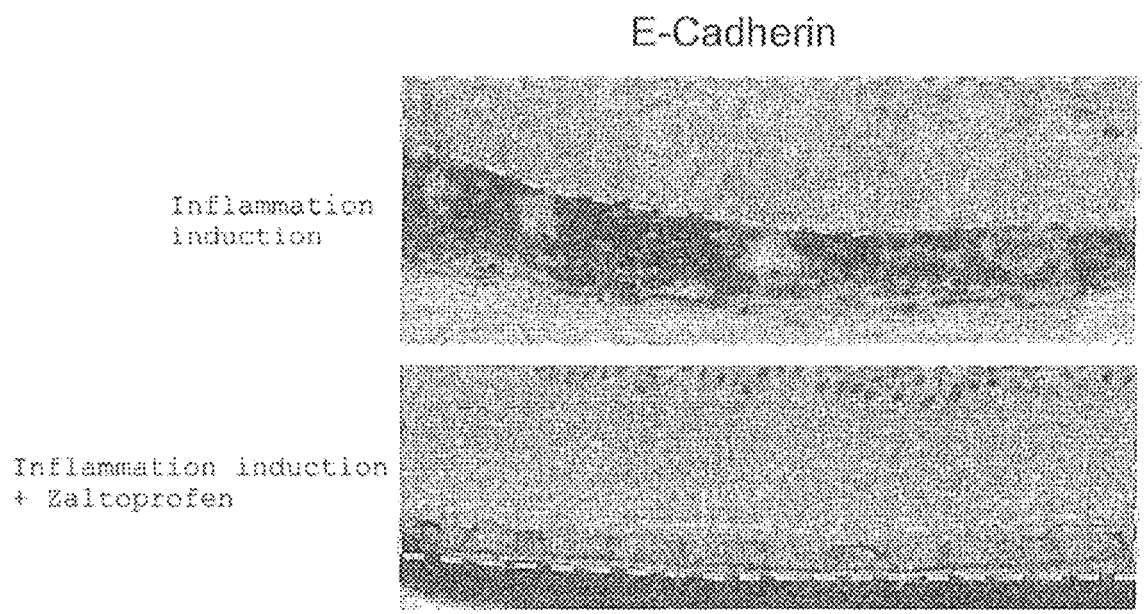
FIG. 52 includes photographs showing the pharmacological assessment of zaltoprofen for formation of a drusen-like structure, indicated by immunostaining of E-Cadherin.
Figure 53:
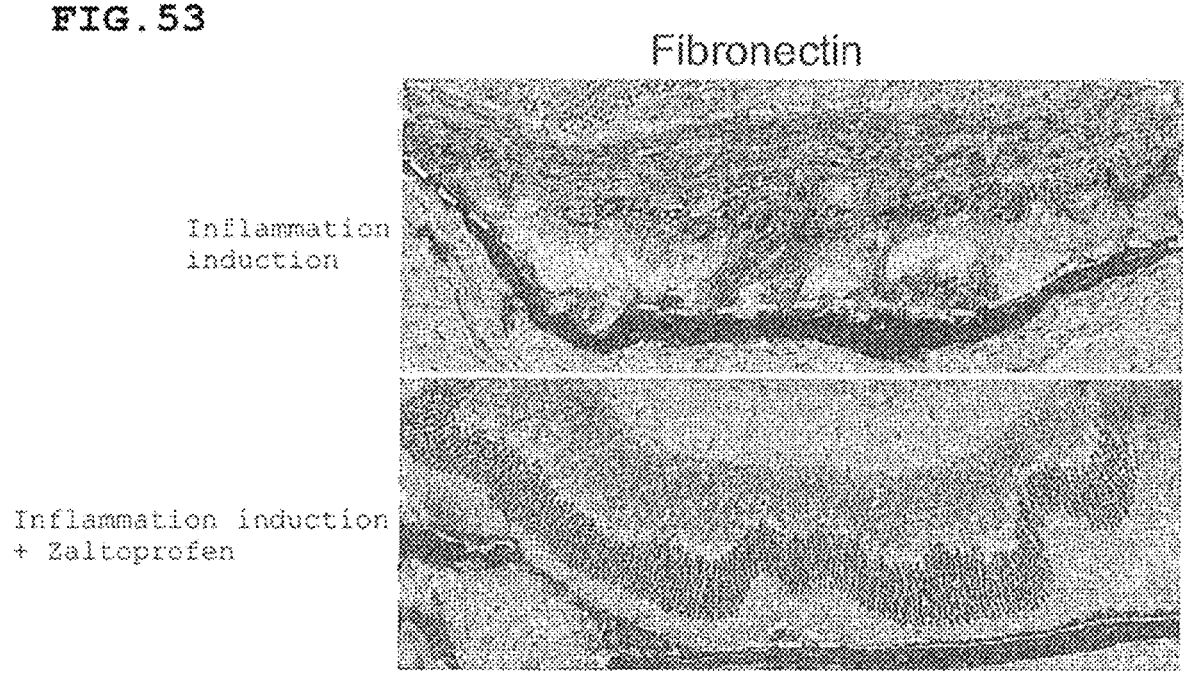
FIG. 53 includes photographs showing the pharmacological assessment of zaltoprofen for formation of a drusen-like structure, indicated by immunostaining of Fibronectin.

Pharmacological assessments of oxaprozin are shown in FIG. 45 to FIG. 47. Pharmacological assessments of epalrestat are shown in FIG. 48 to FIG. 50. Pharmacological assessments of zaltoprofen are shown in FIG. 51 to FIG. 53.

As shown in FIG. 45, a drusen-like structure (the part surrounded by the dotted line) was formed in the retinal region by induction of inflammation (upper photograph). In the oxaprozin administration group, formation of a drusen-like structure was apparently suppressed (lower photograph).

After induction of inflammation, the retinal pigment epithelial cells aligning in a single layer were not observed, but existed inside or around the drusen-like structure, and close binding with the neighboring cells disappeared, and the shape changed into a spindle shape from the cubic shape. On the other hand, in the oxaprozin administration group, cells keeping a cubic shape were abundantly observed.

As shown in FIG. 46, in the retinal pigment epithelial cells inside or around the drusen-like structure formed by induction of inflammation, staining of E-Cadherin disappeared (upper photograph). On the other hand, in the retinal epithelial cells of the oxaprozin administration group, strongly positive staining was observed between cells, and strong intracellular adhesion was retained (lower photograph).

As shown in FIG. 47, inside and around the drusen-like structure that was formed by induction of inflammation, staining was positive, and expression of Fibronectin was observed (upper photograph). On the other hand, in the oxaprozin administration group, formation of a drusen-like structure was suppressed, and the signal strength of staining was small (lower photograph).

As shown in FIG. 48, a drusen-like structure (the part surrounded by the dotted line) was formed in the retinal region by induction of inflammation (upper photograph). In the epalrestat administration group, formation of a drusen-like structure was apparently suppressed (lower photograph).

After induction of inflammation, the retinal pigment epithelial cells aligning in a single layer were not observed, but existed inside or around the drusen-like structure, and close binding with the neighboring cells disappeared, and the shape changed into a spindle shape from the cubic shape. On the other hand, in the epalrestat administration group, cells keeping a cubic shape were abundantly observed.

As shown in FIG. 49, in the retinal pigment epithelial cells inside or around the drusen-like structure formed by induction of inflammation, staining of E-Cadherin disappeared (upper photograph). On the other hand, in the retinal epithelial cells of the epalrestat administration group, strongly positive staining was observed between cells, and strong intracellular adhesion was retained (lower photograph).

As shown in FIG. 50, inside and around the drusen-like structure that was formed by induction of inflammation, staining was positive, and expression of Fibronectin was observed (upper photograph). On the other hand, in the epalrestat administration group, formation of a drusen-like structure was suppressed, and the signal strength of staining was small (lower photograph).

As shown in FIG. 51, a drusen-like structure (the part surrounded by the dotted line) was formed in the retinal region by induction of inflammation (upper photograph). In the zaltoprofen administration group, formation of a drusen-like structure was apparently suppressed (lower photograph).

After induction of inflammation, the retinal pigment epithelial cells aligning in a single layer were not observed, but existed inside or around the drusen-like structure, and close binding with the neighboring cells disappeared, and the shape changed into a spindle shape from the cubic shape. On the other hand, in the zaltoprofen administration group, cells keeping a cubic shape were abundantly observed.

As shown in FIG. 52, in the retinal pigment epithelial cells inside or around the drusen-like structure formed by induction of inflammation, staining of E-Cadherin disappeared (upper photograph). On the other hand, in the retinal epithelial cells of the zaltoprofen administration group, strongly positive staining was observed between cells, and strong intracellular adhesion was retained (lower photograph).

As shown in FIG. 53, inside and around the drusen-like structure that was formed by induction of inflammation, staining was positive, and expression of Fibronectin was observed (upper photograph). On the other hand, in the zaltoprofen administration group, formation of a drusen-like structure was suppressed, and the signal strength of staining was small (lower photograph).

FORMULATION EXAMPLES

Formulation Example 1 Tablet

Tablets are produced by tableting according to an ordinary production method of tablets. The tablets can be produced as an uncoated tablet containing 100 mg or 200 mg of oxaprozin, together with carmellose calcium, hypromellose, crystalline cellulose, magnesium aluminometasilicate, magnesium stearate and so on as additives, and normally can be orally administered in an adult daily dose of 400 mg once or in two batches. The maximum daily dose is 600 mg, although it appropriately increases or decreases depending on the age, symptom and the like.

Formulation Example 2-1 Tablet

Tablets are produced by tableting according to an ordinary production method of tablets. The tablets can be produced as a film-coated tablet containing 80 mg of zaltoprofen, together with carmellose calcium, crystalline cellulose, titanium oxide, magnesium stearate, corn starch, lactose hydrate, hydroxypropylcellulose, hypromellose, and macrogol 6000 as additives, and normally can be orally administered in an adult dose of 80 mg three times a day. In the case of as-needed use, a single dose of 80 mg to 160 mg is orally administered.

Formulation Example 2-2 Tablet

Tablets are produced by tableting according to an ordinary production method of tablets. The tablets can be produced as a film-coated tablet containing 80 mg of zaltoprofen, together with carnauba wax, carmellose calcium, crystalline cellulose, titanium oxide, magnesium stearate, corn starch, lactose hydrate, hydroxypropylcellulose, and hypromellose as additives, and normally can be orally administered in an adult single dose of 80 mg three times a day. In the case of as-needed use, a single dose of 80 mg to 160 mg is orally administered.

Formulation Example 3 Tablet

Tablets are produced by tableting according to an ordinary production method of tablets. The tablets can be produced as a film-coated tablet containing 20 mg of zafirlukast, together with lactose hydrate, crystalline cellulose, povidone, cross carmellose sodium, magnesium stearate, hypromellose, titanium oxide and so on as additives, and normally can be orally administered in an adult daily dose of 40 mg to 80 mg in two batches after breakfast and before bedtime. A daily dose in the elderly is 40 mg, and the maximum. adult (excluding the elderly) daily dose is 80 mg.

Formulation Example 4 Tablet

Tablets are produced by tableting according to an ordinary production method of tablets. The tablets can be produced as an uncoated tablet containing 25 mg or 50 mg of amlexanox, together with corn starch, hydroxypropylcellulose, carmellose calcium, magnesium stearate, lactose hydrate and so on as additives, and normally can be orally administered in an adult single dose of 25 to 50 mg depending on the symptom three times a day, in the morning, in the evening, and before bedtime, or in the morning, in the daytime and in the evening.

Formulation Example 5 Tablet

Tablets are produced by tableting according to an ordinary production method of tablets. The tablets can be produced as a film-coated tablet containing 50 mg of epalrestat, together with D-mannitol, hydroxypropylcellulose, carmellose calcium, magnesium stearate, hypromellose, titanium oxide, polyoxyethylene (105) polyoxypropylene (5) glycol and so on as additives, normally can be orally administered in an adult single dose of 50 mg three times a day before every meal. The dose can be appropriately increased or decreased depending on the age, symptom and the like.

Formulation Example 6 Tablet

Tablets are produced by tableting according to an ordinary production method of tablets. The tablets can be produced as a film-coated tablet containing 100 mg or 200 mg of tiaprofenic acid, together with corn starch, magnesium stearate, talc, hypromellose, titanium oxide, hydroxypropylcellulose, propylene glycol, polyoxyethylene[160]polyoxypropylene[30]glycol and so on as additives, and normally can be orally administered in an adult single dose of 200 mg three times a day. The dose can be appropriately increased or decreased depending on the age, symptom and the like.

Formulation Example 7 Tablet

Tablets are produced by tableting according to an ordinary production method of tablets. The tablets can be produced as an uncoated tablet containing 125 mg or 250 mg of flufenamic acid aluminum, together with carmellose calcium, hypromellose, crystalline cellulose, magnesium aluminometasilicate, magnesium stearate and so on as additives, and normally can be orally administered in an adult dose of 125 to 250 mg in three batches a day. The maximum daily dose is 750 mg, although it appropriately increases or decreases depending on the age, symptom and the like.

Formulation Example 8 Tablet

Tablets are produced by tableting according to an ordinary production method of tablets. The tablets can be produced as an uncoated tablet containing 250 mg of mefenamic acid, together with corn starch, hypromellose, magnesium aluminometasilicate, talc, titanium oxide and so on as additives, and normally can be orally administered in an adult single dose of 500 mg, followed by administration every 6 hours in a single dose of 250 mg. The maximum daily dose is 1500 mg, although it appropriately increases or decreases depending on the age, symptom and the like.

Formulation Example 9 Tablet

Tablets are produced by tableting according to an ordinary production method of tablets. The tablets can be produced as an uncoated tablet containing 50 mg or 100 mg of sulindac, together with cellulose, pregelatinized starch, magnesium stearate and so on as additives, normally can be orally administered in an adult daily dose of 300 mg in two batches a day. The dose is appropriately increased or decreased depending on the age, symptom and the like.

Formulation Example 10 Tablet

Tablets are produced by tableting according to an ordinary production method of tablets. The tablets can be produced as an uncoated tablet containing 40 mg or 80 mg of seratrodast, together with hydroxypropylcellulose, magnesium stearate, corn starch, lactose hydrate and so on as additives, and normally can be orally administered in an adult dose of 80 mg once a day.

The invention claimed is:

1. A method of preventing and/or treating age-related macular degeneration in a patient, said method comprising administering a propionic acid-based nonsteroidal anti-inflammatory drug, an aminoaryl carboxylic acid-based nonsteroidal anti-inflammatory drug, an aldose reductase inhibitor, a leukotriene receptor antagonist, a chemical mediator release suppressor, or a thromboxane A2 receptor antagonist as an active ingredient, wherein the active ingredient is formulated as an oral agent, an ophthalmic solution, an ophthalmic ointment, or an injection provided it is not an ophthalmic injection, wherein the aldose reductase inhibitor is epalrestat and/or a pharmaceutically acceptable salt thereof to the patient, wherein said propionic acid-based nonsteroidal anti-inflammatory drug is at least one selected from the group consisting of zaltoprofen, oxaprozin, tiaprofenic acid, and pharmaceutically acceptable salts thereof wherein said aminoaryl carboxylic acid-based nonsteroidal anti-inflammatory drug is at least one selected from the group consisting of flufenamic acid, mefenamic acid, and pharmaceutically acceptable salts thereof, wherein said leukotriene receptor antagonist is at least one selected from the group consisting of zafirlukast, montelukast, pranlukast, and pharmaceutically acceptable salts thereof, wherein said chemical mediator release suppressor is amlexanox and/or a pharmaceutically acceptable salt thereof, and/or wherein said thromboxane A2 receptor antagonist is seratrodast and/or a pharmaceutically acceptable salt thereof.

2. The method according to claim 1, wherein the age-related macular degeneration is exudative age-related macular degeneration (Wet AMD), atrophic age-related macular degeneration (Dry AMD) or retinal angiomatous proliferation (RAP).

3. The method according to claim 1, wherein the age-related macular degeneration is non-progressive AMD, early AMD, intermediate AMD or late AMD.

4. The method according to claim 1, wherein zaltoprofen or a salt thereof is administered in an administration amount that achieves a Cmax of greater than or equal to 16.8μM.

5. The method according to claim 1, wherein oxaprozin or a salt thereof is administered in an administration amount that achieves a Cmax of greater than or equal to 340.9μM.

6. The method according to claim 1, wherein tiaprofenic acid or a salt thereof is administered in an administration amount that achieves a Cmax of greater than or equal to 69.15μM.

* * * * *